United States Patent
Velema et al.

(10) Patent No.: US 11,572,557 B2
(45) Date of Patent: Feb. 7, 2023

(54) PHOTOREVERSIBLE ACYLATION REAGENTS

(71) Applicant: The Board of Trustees of the Leland Stanford Junior University, Stanford, CA (US)

(72) Inventors: Willem Arend Velema, Stanford, CA (US); Eric T. Kool, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 970 days.

(21) Appl. No.: 16/261,422

(22) Filed: Jan. 29, 2019

(65) Prior Publication Data

US 2019/0264205 A1 Aug. 29, 2019

Related U.S. Application Data

(60) Provisional application No. 62/623,424, filed on Jan. 29, 2018.

(51) Int. Cl.

| | |
|---|---|
| *C12N 15/113* | (2010.01) |
| *C12Q 1/6876* | (2018.01) |
| *A61K 41/00* | (2020.01) |
| *A61K 47/54* | (2017.01) |
| *C07H 21/00* | (2006.01) |

(52) U.S. Cl.
CPC ........ *C12N 15/113* (2013.01); *A61K 41/0042* (2013.01); *A61K 47/54* (2017.08); *C07H 21/00* (2013.01); *C12Q 1/6876* (2013.01); *C12N 2310/128* (2013.01); *C12N 2310/16* (2013.01); *C12N 2310/351* (2013.01)

(58) Field of Classification Search
None
See application file for complete search history.

(56) References Cited

PUBLICATIONS

Shestopalov et al., "Light-controlled gene silencing in zebrafish embryos", Nature Chemical Biology, vol. 3, No. 10, Aug. 23, 2007, pp. 650-651.
Spitale et al., "RNA Shape analysis in living cells", Nature Chemical Biology, vol. 9, No. 1, Nov. 25, 2012, pp. 18-20.
Spitale et al., "Structural imprints in vivo decode RNA regulatory mechanisms", Nature, vol. 519, No. 7544, Mar. 18, 2015, pp. 486-490.
Tang et al., "Regulating Gene Expression in Zebrafish Embryos Using Light-Activated, Negatively Charged Peptide Nucleic Acids", Journal of the American Chemical Society, vol. 129, No. 36, Aug. 21, 2007, pp. 11000-11001.
Velema et al., "Fluorogenic Templated Reaction Cascades for RNA Detection", Journal of the American Chemical Society, vol. 139, No. 15, Mar. 27, 2017, pp. 5405-5411.
Velema et al., "RNA Control by Photoreversible Acylation", Journal of the American Chemical Society, vol. 140, No. 10, Feb. 23, 2018, pp. 3491-3495.
Wenter et al., "Kinetics of Photoinduced RNA Refolding by Real-Time NMR Spectroscopy", Angewandte Chemie International Edition, vol. 44, No. 17, Apr. 22, 2005, pp. 2600-2603.
Wilson et al., "Molecular Mechanisms of RNA Interference", Annual Review of Biophysics, vol. 42, May 2013, pp. 217-239.
Wu et al., "Caged circular antisense oligonucleotides for photomodulation of RNA digestion and gene expression in cells", Nucleic Acids Research, vol. 41, No. 1, Jan. 1, 2013, pp. 677-686.
Young et al., "Photochemical hammerhead ribozyme activation", Bioorganic & Medicinal Chemistry Letters, vol. 16, No. 10, May 15, 2006, pp. 2658-2661.
Zheng et al., "Temporal and Spatial Regulation of MicroRNA Activity with Photoactivatable Cantimirs", ACS Chemical Biology, vol. 6, No. 12, Oct. 6, 2011, pp. 1332-1338.
Acharya et al., "The pKa of the Internucleotidic 2'-Hydroxyl Group in Diribonucleoside (3'→5') Monophosphates," The Journal of Organic Chemistry, vol. 68, No. 5, Feb. 4, 2003, pp. 1906-1910.
Ando et al., "Photo-mediated gene activation using caged RNA/DNA in zebrafish embryos," Nature Genetics, vol. 28, No. 4, Jul. 23, 2001, pp. 317-325.
Ankenbruck et al., "Optochemical Control of Biological Processes in Cells and Animals," Angewandte Chemie International Edition, vol. 57, No. 11, May 18, 2017, pp. 2768-2798.
Appella, "Non-natural nucleic acids for synthetic biology," Current Opinion in Chemical Biology, vol. 13, No. 5-6, Dec. 2009, pp. 687-696.
Blidner et al., "Photoinduced RNA interference using DMNPE-caged 2'-deoxy-2'-fluoro substituted nucleic acids in vitro and in vivo," Molecular BioSystems, vol. 4, No. 5, Mar. 31, 2008, pp. 431-440.
Brieke et al., "Light-Controlled Tools," Angewandte Chemie International Edition, vol. 51, No. 34, Aug. 20, 2012, pp. 8446-8476.
Buff et al., "Dependence of aptamer activity on opposed terminal extensions: improvement of light-regulation efficiency," Nucleic Acids Research, vol. 38, No. 6, Dec. 8, 2009, pp. 2111-2118.
Butcher et al., "Towards understanding the catalytic core structure of the spliceosome," Biochemical Society Transactions, vol. 33, No. 3, Jun. 2005, pp. 447-449.
Cantara et al., "The RNA modification database, RNAMDB: 2011 update," Nucleic Acids Research, vol. 39, Supplement 1, Jan. 1, 2011, pp. D195-D201.
Cech et al., "The Noncoding RNA Revolution—Trashing Old Rules to Forge New Ones," Cell, vol. 157, No. 1, Mar. 27, 2014, pp. 77-94.
Chaulk et al., "Caged RNA: Photo-control of a ribozyme reaction," Nucleic Acids Research, vol. 26, No. 13, Jul. 1, 1998, pp. 3173-3178.
Chaulk et al., "Synthesis of oligo-RNAs with photocaged adenosine 2'-hydroxyls," Nature Protocols, vol. 2, No. 5, Apr. 26, 2007, pp. 1052-1058.

(Continued)

*Primary Examiner* — Sean McGarry
(74) *Attorney, Agent, or Firm* — KPPB LLP

(57) ABSTRACT

Reagents and methods to cloak and uncloak RNA polymers and applications thereof are provided. Photocloaking molecules are used to label RNA polymers. Radiant energy is used to remove photoreleaseable protecting adducts and revert a RNA polymer to its native form.

18 Claims, 44 Drawing Sheets

Specification includes a Sequence Listing.

(56) References Cited

PUBLICATIONS

Deiters et al., "Photocaged Morpholino Oligomers for the Light-Regulation of Gene Function in Zebrafish and Xenopus Embryos," Journal of the American Chemical Society, vol. 132, No. 44, Oct. 20, 2010, pp. 15644-15650.
Delebecque et al., "Organization of Intracellular Reactions with Rationally Designed RNA Assemblies," Science, vol. 333, No. 6041, Jul. 22, 2011, pp. 470-474.
Dieci et al., "Eukaryotic snoRNAs: A paradigm for gene expression flexibility," Genomics, vol. 94, No. 2, Aug. 2009, pp. 83-88.
Filonov et al., "Broccoli: Rapid Selection of an RNA Mimic of Green Fluorescent Protein by Fluorescence-Based Selection and Directed Evolution," Journal of the American Chemical Society, vol. 136, No. 46, Oct. 22, 2014, pp. 16299-16308.
Filonov et al., "In-Gel Imaging of RNA Processing Using Broccoli Reveals Optimal Aptamer Expression Strategies," Chemistry & Biology, vol. 22, No. 5, May 21, 2015, pp. 649-660.
Franzini et al., "Efficient Nucleic Acid Detection by Templated Reductive Quencher Release," Journal of the American Chemical Society, vol. 131, No. 44, Jul. 14, 2009, pp. 16021-16023.
Gautier et al., "How to control proteins with light in living systems," Nature Chemical Biology, vol. 10, No. 7, Jun. 17, 2014, pp. 533-541.
Gilmore et al., "N-Terminal Protein Modification through a Biomimetic Transamination Reaction," Angewandte Chemie International Edition, vol. 45, No. 32, Aug. 11, 2006, pp. 5307-5311.
Govan et al., "Optochemical control of RNA interference in mammalian cells," Nucleic Acids Research, vol. 41, No. 22, Dec. 1, 2013, pp. 10518-10528.
Guo et al., "Four-color DNA sequencing with 3'-O-modified nucleotide reversible terminators and chemically cleavable fluorescent dideoxynucleotides," Proceedings of the National Academy of Sciences of the United States of America, vol. 105, No. 27, Jul. 8, 2008, pp. 9145-9150.
Hansen et al., "Wavelength-selective cleavage of photoprotecting groups strategies and applications in dynamic systems," Chemical Society Reviews, vol. 44, No. 11, Apr. 28, 2015, pp. 3358-3377.
Heckel et al., "Light Regulation of Aptamer Activity: An Anti-Thrombin Aptamer with Caged Thymidine Nucleobases," Journal of the American Chemical Society, vol. 127, No. 3, Dec. 24, 2004, pp. 822-823.
Hobartner et al., "Modulation of RNA Tertiary Folding by Incorporation of Caged Nucleotides," Angewandte Chemie International Edition, vol. 44, No. 44, Nov. 11, 2005, pp. 7305-7309.
Inaki, "Synthetic nucleic acid analogs," Progress in Polymer Science, vol. 17, No. 4, 1992, pp. 515-570.
Keam et al., "tRNA-Derived Fragments (tRFs): Emerging New Roles for an Ancient RNA in the Regulation of Gene Expression," Life, vol. 5, No. 4, Nov. 27, 2015, pp. 1638-1651.
Klan et al., "Photoremovable Protecting Groups in Chemistry and Biology: Reaction Mechanisms and Efficacy," Chemical Reviews, vol. 113, No. 1, Dec. 21, 2012, pp. 119-191.
Knezevic et al., "Light- and pH-Responsive Release of Doxorubicin from a Mesoporous Silica-Based Nanocarrier," Chemistry—A European Journal, vol. 17, No. 12, Mar. 14, 2011, pp. 3338-3342.

Lee et al., "A novel class of small RNAs: tRNA-derived RNA fragments (tRFs)," Genes & Development, vol. 23, 2009, pp. 2639-2649.
Li et al., "A Covalent Approach for Site-Specific RNA Labeling in Mammalian Cells," Angewandte Chemie International Edition, vol. 54, No. 15, Apr. 7, 2015, pp. 4597-4602.
Li et al., "Aptamer photoregulation in vivo," Proceedings of the National Academy of Sciences of the United States of America, vol. 111, No. 48, Nov. 17, 2014, pp. 17099-17103.
Liu et al., "Optochemical Control of Deoxyoligonucleotide Function via a Nucleobase-Caging Approach," Accounts of Chemical Research, vol. 47, No. 1, Aug. 28, 2013, pp. 45-55.
Liu et al., "The structure of a nucleolytic ribozyme that employs a catalytic metal ion," Nature Chemical Biology, vol. 13, No. 5, Mar. 6, 2017, pp. 508-513.
Low et al., "SHAPE-directed RNA secondary structure prediction," Methods, vol. 52, No. 2, Oct. 2010, pp. 150-158.
Lu et al., "Synthesis of 2'-O-Photocaged Ribonucleoside Phosphoramidites," Nucleosides, Nucleotides & Nucleic Acids, vol. 34, No. 2, Jan. 26, 2015, pp. 114-129.
Lubbe et al., "Recent developments in reversible photoregulation of oligonucleotide structure and function," Chemical Society Reviews, vol. 46, No. 4, Feb. 20, 2017, pp. 1052-1079.
Lucas et al., "Light-inducible antimiR-92a as a therapeutic strategy to promote skin repair in healing-impaired diabetic mice," Nature Communications, vol. 8, No. 15162, May 2, 2017, 9 pgs.
Matsuo et al., "One-step construction of caged carbonic anhydrase I using a ligand-directed acyl imidazole-based protein labeling method," Chemical Science, vol. 4, No. 6, Apr. 9, 2013, pp. 2573-2580.
Matsushita-Ishiodori et al., "Photoinduced RNA Interference," Accounts of Chemical Research, vol. 45, No. 7, Feb. 24, 2012, pp. 1039-1047.
Merino et al., "RNA Structure Analysis at Single Nucleotide Resolution by Selective 2'-Hydroxyl Acylation and Primer Extension (SHAPE)," Journal of the American Chemical Society, vol. 127, No. 12, Mar. 4, 2005, pp. 4223-4231.
Meyer et al., "RNA Interference Controlled by Light of Variable Wavelength," Angewandte Chemie International Edition, vol. 53, No. 47, Sep. 22, 2014, pp. 12840-12843.
Mikat et al., "Light-dependent RNA interference with nucleobase-caged siRNAs," RNA, vol. 13, No. 12, Dec. 2007, pp. 2341-2347.
Nierth et al., "Efficient photoactivation of a Diels-Alderase ribozyme," Chemical Communications, vol. 46, No. 42, Sep. 27, 2010, pp. 7975-7977.
Panja et al., "Light-Triggered RNA Annealing by an RNA Chaperone," Angewandte Chemie International Edition, vol. 54, No. 25, Jun. 15, 2015, pp. 7281-7284.
Pinto et al., "Functional Detection of Proteins by Caged Aptamers," ACS Chemical Biology, vol. 7, No. 2, Nov. 9, 2011, pp. 360-366.
Qiu et al., "A Targeted, Self-Delivered, and Photocontrolled Molecular Beacon for mRNA Detection in Living Cells," Journal of the American Chemical Society, vol. 135, No. 35, Aug. 9, 2013, pp. 12952-12955.
Resendiz et al., "Photochemical Control of RNA Structure by Disrupting π-Stacking," Journal of the American Chemical Society, vol. 134, No. 30, Jul. 24, 2012, pp. 12478-12481.
Scott et al., "Chapter One—The Hammerhead Ribozyme: Structure, Catalysis, and Gene Regulation," Progress in Molecular Biology and Translational Science, vol. 120, 2013, pp. 1-23.
Shah et al., "Light-Activated RNA Interference," Angewandte Chemie International Edition, vol. 44, No. 9, Feb. 15, 2005, pp. 1329-1332.

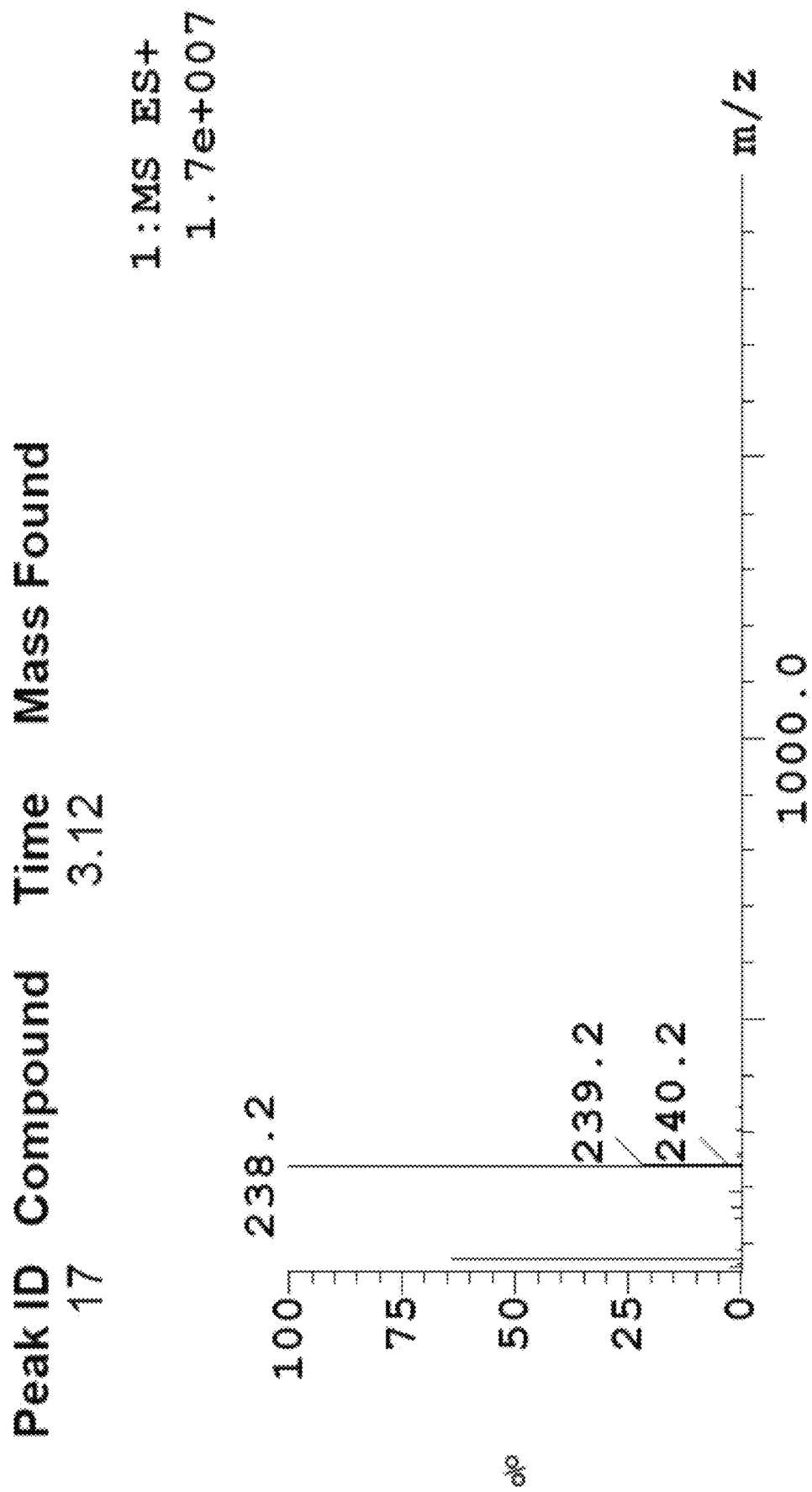

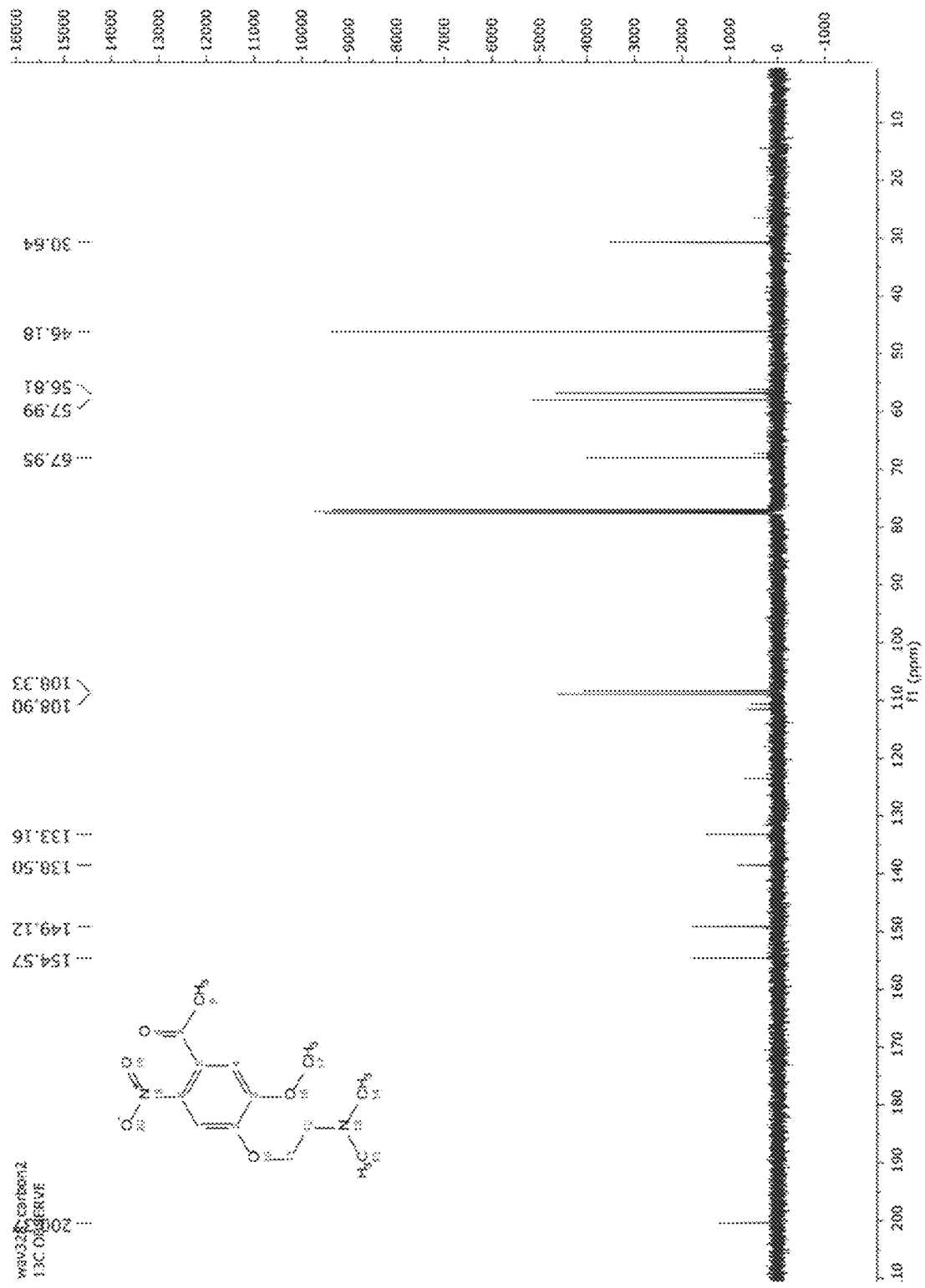

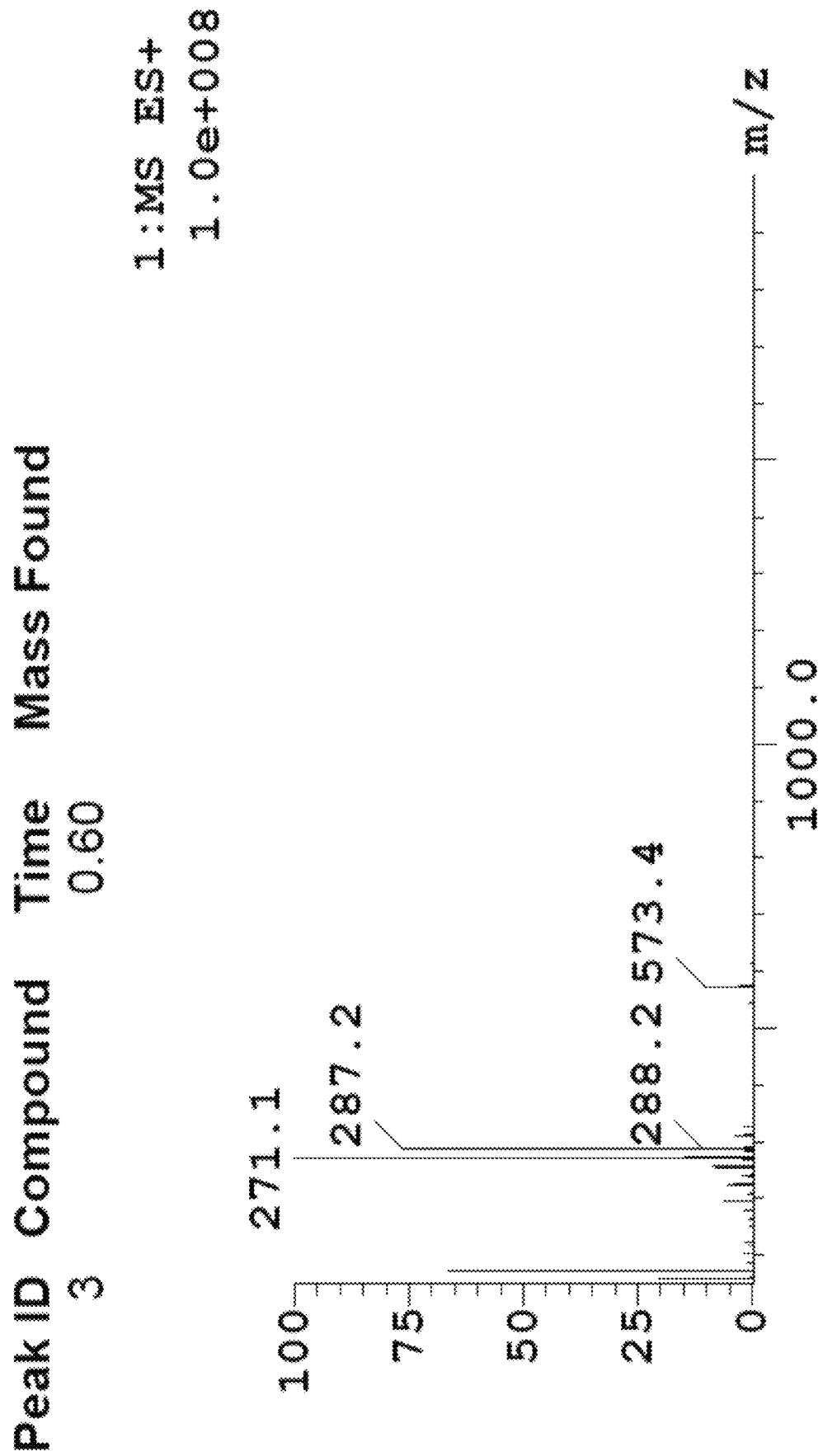

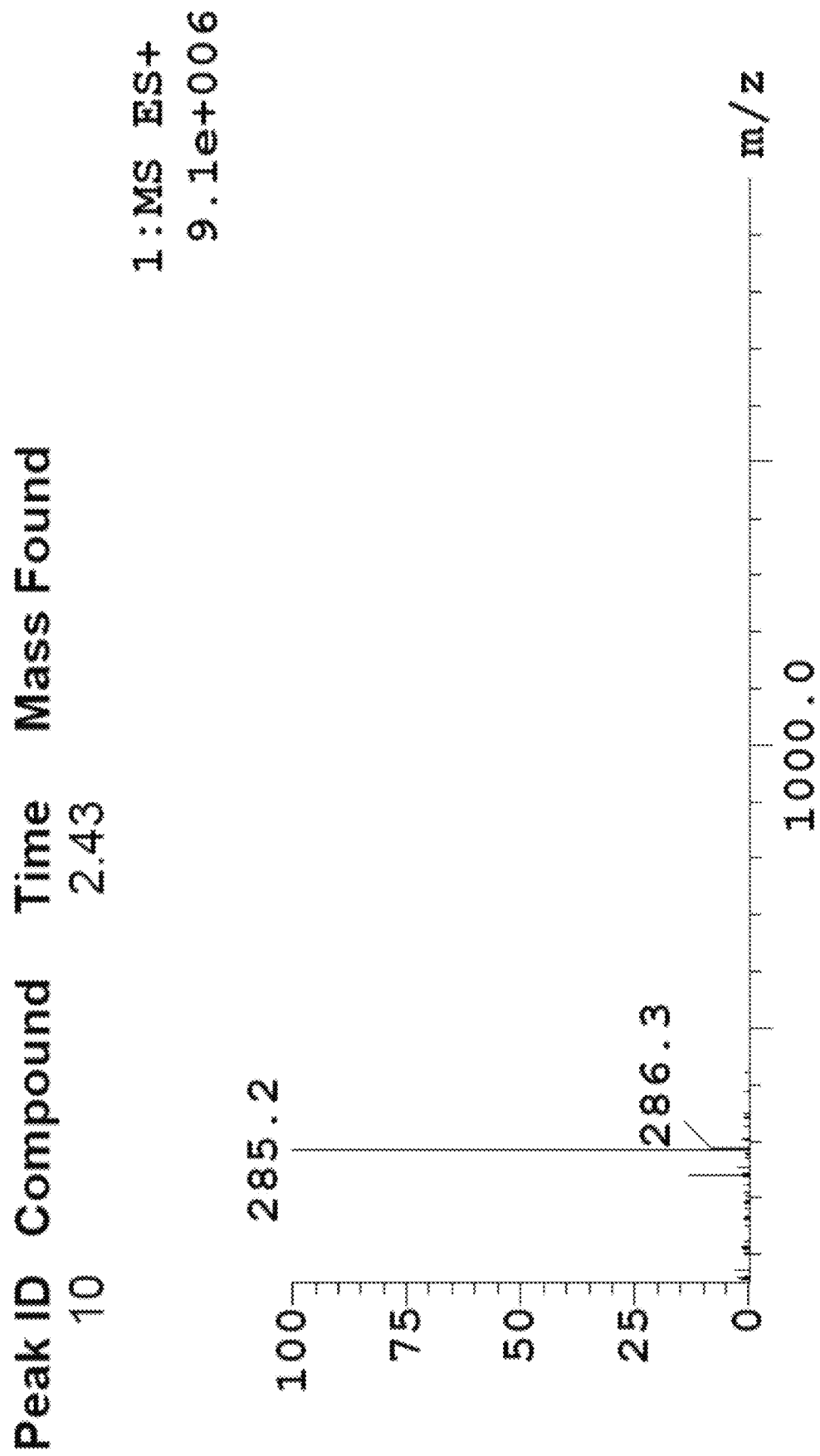

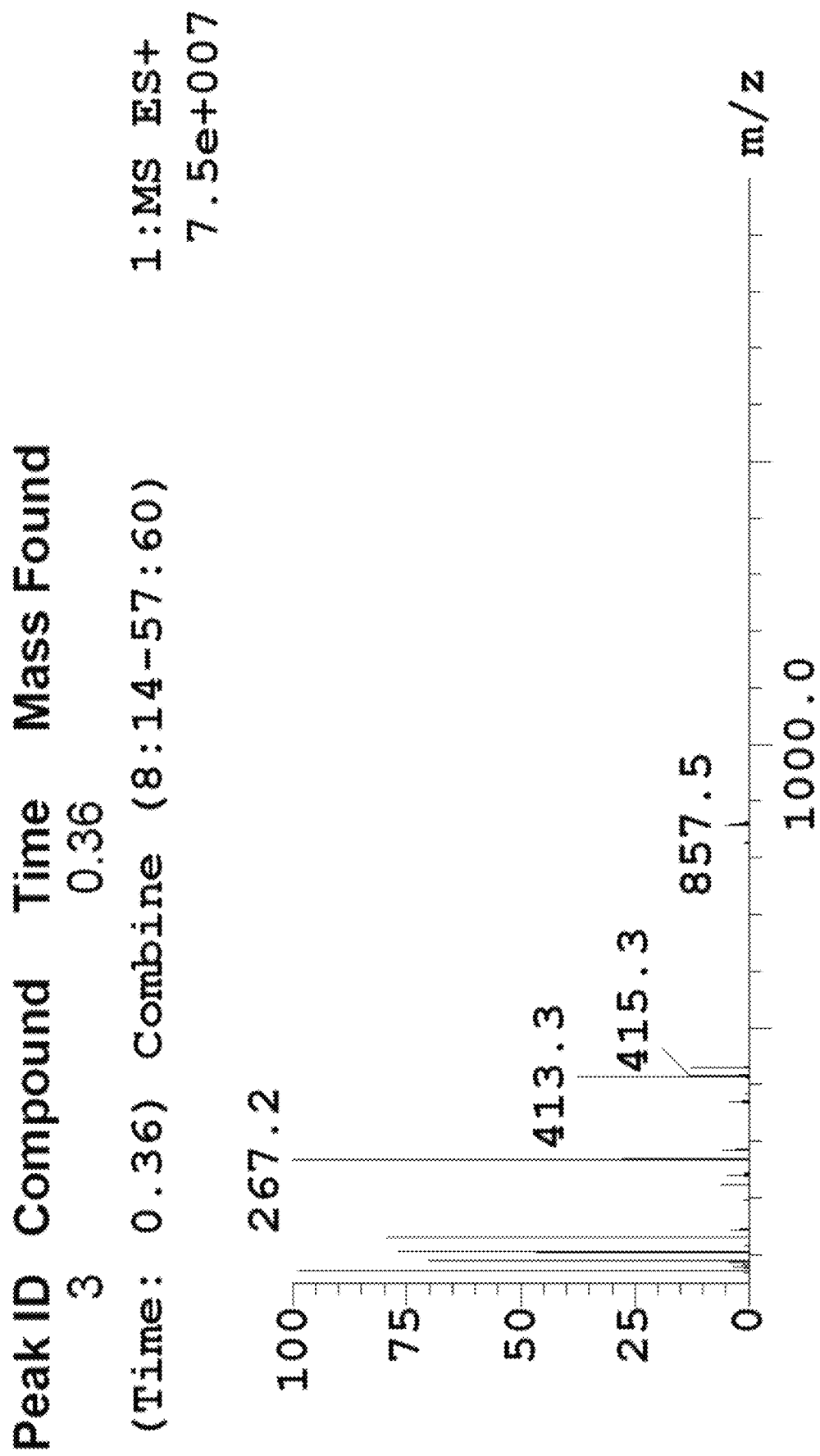

SEQUENCE LISTING

<160> NUMBER OF SEQ ID NOS: 8

<210> SEQ ID NO 1
<211> LENGTH: 12
<212> TYPE: RNA
<213> ORGANISM: Artificial Sequence
<220> FEATURE:
<223> OTHER INFORMATION: 12-mer sequence

<400> SEQUENCE: 1
ggguguaugg uu                          12

<210> SEQ ID NO 2
<211> LENGTH: 16
<212> TYPE: RNA
<213> ORGANISM: Artificial Sequence
<220> FEATURE:
<223> OTHER INFORMATION: RNA template 1

<400> SEQUENCE: 2
gcuccccagc uuucgc                      16

<210> SEQ ID NO 3
<211> LENGTH: 8
<212> TYPE: DNA
<213> ORGANISM: Artificial Sequence
<220> FEATURE:
<223> OTHER INFORMATION: QSTAR Probe

<400> SEQUENCE: 3 tggggagc                               8

<210> SEQ ID NO 4
<211> LENGTH: 8
<212> TYPE: RNA
<213> ORGANISM: Artificial Sequence

```
<220> FEATURE:
<223> OTHER INFORMATION: TPP Probe

<400> SEQUENCE: 4 gcgaaagc                                                                    8

<210> SEQ ID NO 5
<211> LENGTH: 34
<212> TYPE: RNA
<213> ORGANISM: Artificial Sequence
<220> FEATURE:
<223> OTHER INFORMATION: Hammerhead Ribozyme

<400> SEQUENCE: 5
gggaccacug augaggccgu uaggccgaaa cacc                                      34

<210> SEQ ID NO 6
<211> LENGTH: 123
<212> TYPE: RNA
<213> ORGANISM: Artificial Sequence
<220> FEATURE:
<223> OTHER INFORMATION: F30 Broccoli aptamer

<400> SEQUENCE: 6
uaauacgacu cacuauaggg uugccaugug uaugugggag acggucgggu ccagauauuc           60
guaucugucg aguagagugu gggcucccac auacucugau gauccuucgg gaucauucau          120
ggc                                                                       123

<210> SEQ ID NO 7
<211> LENGTH: 136
<212> TYPE: DNA
<213> ORGANISM: Artificial Sequence
<220> FEATURE:
<223> OTHER INFORMATION: F30-2xdB_1

<400> SEQUENCE: 7
taatacgact cactataggg ttgccatgtg tatgtgggag acggtcgggt ccatctgaga           60
cggtcgggtc cagatattcg tatctgtcga gtagagtgtg ggctcagatg tcgagtagag          120
tgtgggctcc cacata                                                         136

<210> SEQ ID NO 8
<211> LENGTH: 118
<212> TYPE: DNA
<213> ORGANISM: Artificial Sequence
<220> FEATURE:
<223> OTHER INFORMATION: F30-2xdB_2

<400> SEQUENCE: 8
ctctgatgat ccagacggtc gggtccatct gagacggtcg ggtccagata ttcgtatctg           60
tcgagtagag tgtgggctca gatgtcgagt agagtgtggg ctggatcatt catggcaa           118
```

PHOTOREVERSIBLE ACYLATION REAGENTS

CROSS REFERENCE TO RELATED APPLICATIONS

This application claims priority to U.S. Provisional Application Ser. No. 62/623,424 entitled "Photoreversible Acylation Reagents," filed Jan. 29, 2018, which is herein incorporated by reference in its entirety.

STATEMENT REGARDING FEDERALLY SPONSORED RESEARCH OR DEVELOPMENT

This invention was made with Government support under contracts GM127295 and GM068122 awarded by the National Institutes of Health. The Government has certain rights in the invention.

FIELD OF THE INVENTION

The invention is generally directed to photoreversible acylation reagents that are capable of acylation and deacylation of ribonucleic acid polymers (RNA), the acylated RNA products, and methods and applications thereof.

BACKGROUND

Ribonucleic acid (RNA) is a polymeric molecule existing in biological cells in several forms and having various functions. Much like deoxyribonucleic acid (DNA), RNA is a chain of nucleotides, which formulate a sequence. Each nucleotide is composed of a nitrogenous base, a 5-carbon sugar (e.g., ribose), and at least one phosphate group. The four canonical bases of RNA are adenine (A), cytosine (C), guanine (G), and uracil (U); however, several other noncanonical bases are often incorporated into the polymer, such as, for example, inosine (I) or methyl-7-guanosine (m7G). Many naturally occurring and designer modified nucleosides are known and can be incorporated into the RNA polymer. (See, e.g., Cantara, W. A., et al., *Nucleic Acids Research*, 2011, 39(Database issue), D195-D201; Inaki, Y., *Prog. Polym. Sci.*, 1992, 17, 515-70; and Appella, D. H., *Curr. Opin. Chem. Biol.*, 2009, 13, 687-96; the disclosures of which are incorporated herein by reference).

The primary structure of RNA is typically in a linear, single-stranded polymer. The nitrogen bases in an RNA polymer allow it form various secondary structures (e.g., helices, loops, bulges, junctions) dependent on complementary regions of the polymer. Complementary regions can be held together by hydrogen bonding creating helical or junctional regions. The complementary regions also form loops and bulges in unpaired regions between the complementation.

The unique primary and secondary structures of various RNA polymers give rise to its various functions. Messenger RNA (mRNA) uses its primary structure to carry genetic information from DNA to the ribosomes to synthesize proteins. Transfer (tRNA) and ribosomal (rRNA) are short polymers that take advantage of their secondary structures to assist the ribosome in the protein synthesis. Ribozymes are polymers that fold into secondary structure that is capable of enzymatic-like activity. Many other classes RNAs exist, including those that are involved in gene expression (e.g., microRNA (miRNA), small interfering RNAs (siRNA), Piwi-interacting RNAs (piRNA), riboswitches)), and RNA processing (e.g., small nuclear RNAs (snRNA), small nucleolar RNAs (snoRNA)).

Beyond the better-studied messenger RNAs, the largest fraction of cellular RNA consists of noncoding species, including not only tRNAs and rRNAs, but also a growing range of other long and short noncoding species, including snRNA, miRNA, snoRNA, long noncoding RNAs (lncRNA), circular RNAs (circRNA), and tRNA fragments (tRF). (See, e.g., Cech, T. and Steitz, J. A. *Cell* 2014, 157, 77-94; Butcher, S. E. and Brow, D. A. *Biochemical Society Transactions*, 2005, 33, 447; Hannon, G. J. *Nature* 2002, 418, 244-51; Wilson, R. C. and Doudna, J. A. *Annu. Rev. Biophys.*, 2013, 42, 217-39; Dieci, G., Preti, M., and Montanini, B. *Genomics* 2009, 94, 83-88; Chen, L. L., *Nat. Rev. Mol. Cell Biol.*, 2016, 17, 205-11; Lee, Y. S. et al. *Genes Dev.*, 2009, 23, 2639-49; and Keam, S. P. and Hutvagner, G. *Life*, 2015, 5, 1638-51; the disclosures of which are each incorporated herein by reference.) The biological functions of a major fraction of these RNA species remain to be characterized, and their interactions with other RNAs, proteins, and small molecules remain elusive. Recent advancements in next-generation RNA sequencing and in structure mapping have been important in characterizing RNAs, but the field will benefit greatly from new methods as well. (See, e.g., Guo, J., et al., *Proc. Natl. Acad. Sci.*, 2008, 105, 9145-50; Spitale, R. C., et al., *Nat. Chem. Biol.*, 2013, 9, 18-20; Spitale, R. C., et al. *Wiley Interdisciplinary Reviews: RNA*, 2014, 5, 867-81; and Merino, E. J., et al., *J. Am. Chem. Soc.*, 2005, 127, 4223-31; the disclosures of which are each incorporated herein by reference.)

SUMMARY OF THE INVENTION

Many embodiments are directed to photoreversible acylation reagents that are capable of cloaking and uncloaking RNA and photoreversible acylated RNA products. Numerous embodiments are directed to methods of using photoreversible acylation reagents including methods to cloak and uncloak RNA and applications related to cloaked RNA.

In an embodiment, a composition includes at least one RNA polymer, such that the RNA polymer is acylated with a first adduct linked to a 2'-hydroxyl group of a first ribose. The at least one acylated adduct has a structure selected from the following group of structures:

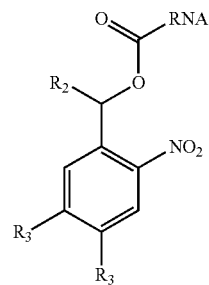

The first adduct is linked to the RNA polymer via a carbonate linkage with the 2'-hydroxyl of ribose; R2 is an alkyl or H; and R3 is an alkoxy or H.

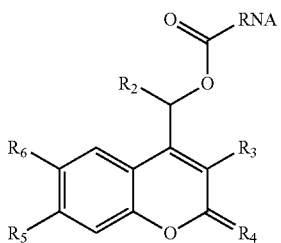

The first adduct is linked to the RNA polymer via a carbonate linkage with the 2'-hydroxyl of ribose; R2 is an alkyl, alkoxy, or H; R3 is an alkyl, aryl, nitro, cyano or H; R4 is (C—R2), O, or S; R5 is an alkoxy, (N—R2), OH, or H; and R6 is a halogen or H.

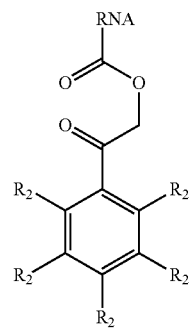

The first adduct is linked to the RNA polymer via a carbonate linkage with the 2'-hydroxyl of ribose; and R2 is an alkyl, alkoxy, nitro, OH, or H.

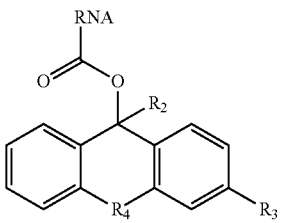

The first adduct is linked to the RNA polymer via a carbonate linkage with the 2'-hydroxyl of ribose; R2 is an aryl or H; R3 is an alkoxy or H; and R4 is O or S.

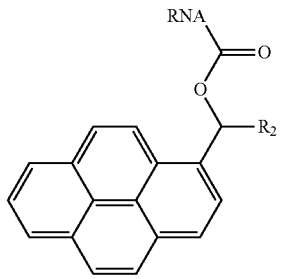

The first adduct is linked to the RNA polymer via a carbonate linkage with the 2'-hydroxyl of ribose; and R2 is an alkyl or H.

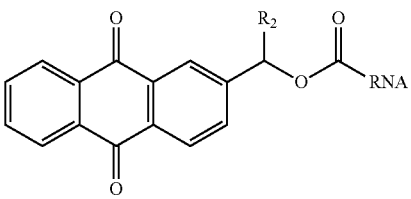

The first adduct is linked to the RNA polymer via a carbonate linkage with the 2'-hydroxyl of ribose; and R2 is an alkyl or H.

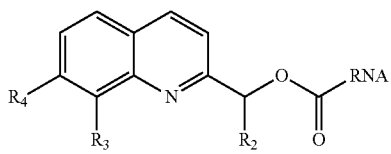

The first adduct is linked to the RNA polymer via a carbonate linkage with the 2'-hydroxyl of ribose; R2 is an alkyl, alkoxy, or H; R3 is a halogen or H; and R4 is an alkoxy, OH, or H.

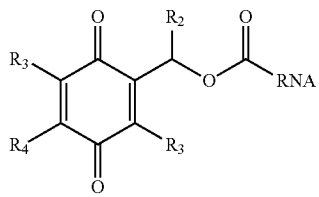

The first adduct is linked to the RNA polymer via a carbonate linkage with the 2'-hydroxyl of ribose; R2 is an alkyl, alkoxy, or H; R3 is an alkyl or H; and R4 is an alkyl, N-alkyl, or H.

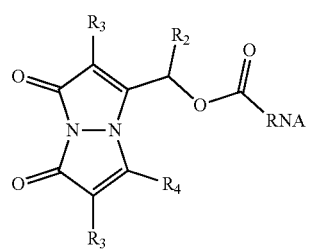

The first adduct is linked to the RNA polymer via a carbonate linkage with the 2'-hydroxyl of ribose; R2 is an alkyl, alkoxy, or H; R3 is an alkyl or H; and R4 is an alkyl, alkoxy, or H.

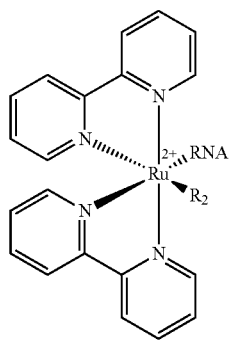

The first adduct is linked to the RNA polymer via a carbonate linkage with the 2'-hydroxyl of ribose; and R2 is an appropriate ligand.

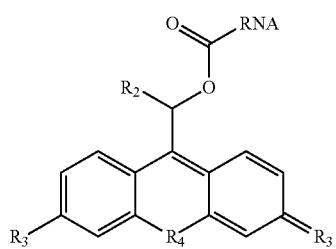

The first adduct is linked to the RNA polymer via a carbonate linkage with the 2'-hydroxyl of ribose; R2 is an alkyl, alkoxy, or H; R3 is an alkoxy, N-alkyl, O, N, or H; and R4 is Si, S, or O. And

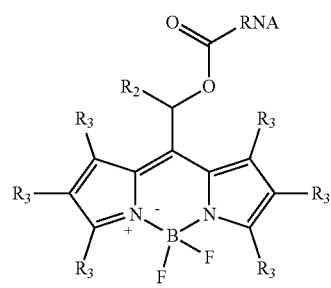

The first adduct is linked to the RNA polymer via a carbonate linkage with the 2'-hydroxyl of ribose; R2 is an alkyl, alkoxy, or H; and R3 is an alkyl, aryl, alkoxy, halogen or H.

In another embodiment, the composition further includes a substituent on the at least one adduct. The substituent is a solubility enhancing group.

In yet another embodiment, the solubility enhancing group is a trialkyl amine.

In a further embodiment, the solubility enhancing group is cationic.

In still yet another embodiment, the solubility enhancing group is anionic.

In yet a further embodiment, the at least one adduct is capable of being removed from the RNA polymer by exposure to radiant energy.

In an even further embodiment, the RNA polymer is polyacylated with at least a second adduct linked to a 2'-hydroxyl group of a second ribose.

In yet an even further embodiment, the linkage of each adduct of the polyacylated RNA polymer was formed by a single cloaking reaction.

In still yet an even further embodiment, the polyacylated RNA polymer has adducts linked to at least a percentage of the ribosyl 2'-hydroxyl groups, wherein the percentage is selected from a group consisting of: 10%, 20%, 30%, 40%, 50%, 60%, 70%, 80%, and 90%.

In still yet an even further embodiment, every accessible ribosyl 2'-hydroxyl group of the RNA polymer is acylated.

In still yet an even further embodiment, the RNA polymer is longer than a length select from a group consisting of: 200 nucleotides (nt), 300 nt, 400 nt, 500 nt, 600 nt, 700 nt, 800 nt, 900 nt, 1000 nt, 2000 nt, and 3000 nt.

In still yet an even further embodiment, the RNA polymer is derived from an in vivo source.

In still yet an even further embodiment, the RNA polymer is derived from an in vitro method.

In still yet an even further embodiment, the in vitro method is one of: RNA polymerase extension and oligomeric synthesis.

In still yet an even further embodiment, the RNA polymer is one of: mRNA, siRNA, miRNA, shRNA, circRNA, antisense RNA, ribozyme, riboswitch, tRNA, rRNA, snRNA, snoRNA, aptamer, and guide RNA for CRISPR/Cas9.

In still yet an even further embodiment, the acylation of the RNA polymer mitigates a function of the polymer.

In still yet an even further embodiment, the function is one of: hybridization, secondary structure formation, mRNA translation, and protein interaction.

In still yet an even further embodiment, the acylated RNA polymer is utilized in a medicament.

In another embodiment, the leaving group is selected from a group consisting of: midazole, triazol, tetrazole, azide, nitryl, N-hydroxysuccinimide and ester.

In yet another embodiment, the leaving group is further substituted.

In a further embodiment, the PPG has an aromatic core.

In still yet another embodiment, the reagent has molecular structure selected from the following structures:

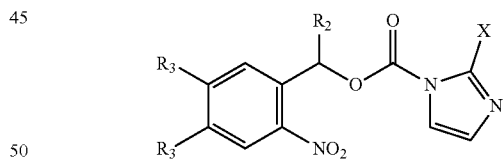

Such that X is a halogen or H; R2 is an alkyl or H; and R3 is an alkoxy or H.

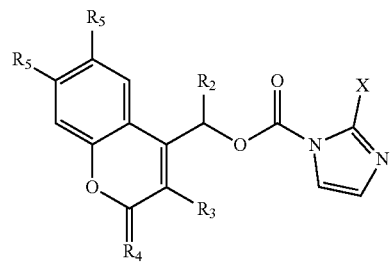

Such that X is a halogen or H; R2 is an alkyl, alkoxy, or H; R3 is an alkyl, aryl, nitro, cyano or H; R4 is (C—R2), O, or S; R5 is an alkoxy, (N—R2), OH, or H; and R6 is a halogen or H.

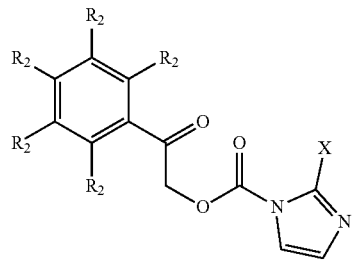

Such that X is a halogen or H; and R2 is an alkyl, alkoxy, nitro, OH, or H.

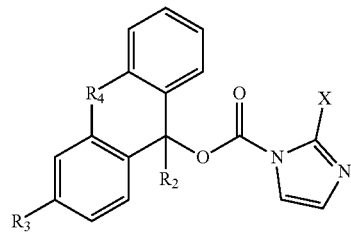

Such that X is a halogen or H; R2 is an aryl or H; R3 is an alkoxy or H; and R4 is O or S.

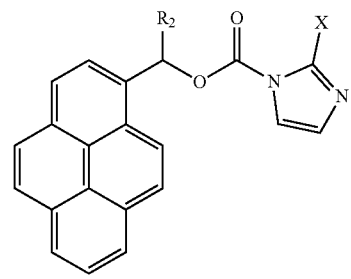

Such that X is a halogen or H; and R2 is an alkyl or H.

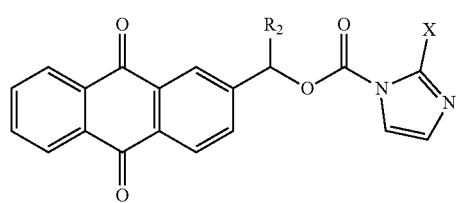

Such that X is a halogen or H; and R2 is an alkyl or H.

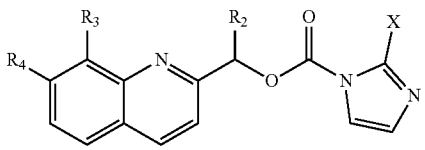

Such that X is a halogen or H; R2 is an alkyl, alkoxy, or H; R3 is a halogen or H; and R4 is an alkoxy, OH, or H.

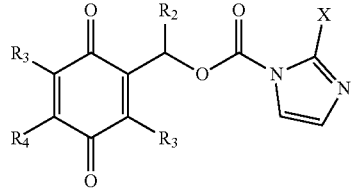

Such that X is a halogen or H R2 is an alkyl, alkoxy, or H; R3 is an alkyl or H; and R4 is an alkyl, N-alkyl, or H.

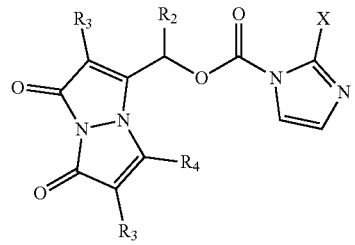

Such that X is a halogen or H; R2 is an alkyl, alkoxy, or H; R3 is an alkyl or H; and R4 is an alkyl, alkoxy, or H.

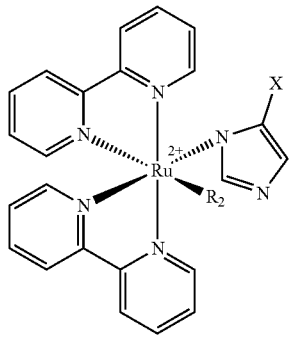

Such that X is a halogen or H; and R2 is an appropriate ligand.

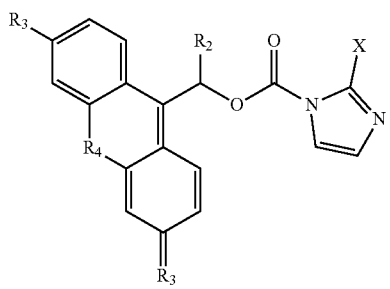

Such that X is a halogen or H; R2 is an alkyl, alkoxy, or H; R3 is an alkoxy, N-alkyl, O, N, or H; and R4 is Si, S, or O. And

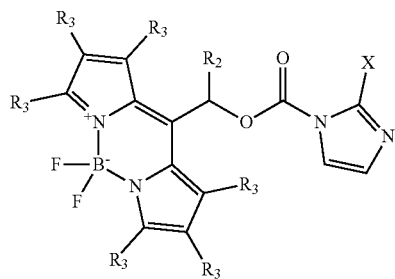

Such that X is a halogen or H; R2 is an alkyl, alkoxy, or H; and R3 is an alkyl, aryl, alkoxy, halogen or H.

In yet a further embodiment, the RNA cloaking reagent further includes a substituent. The substituent is a solubility enhancing group In an even further embodiment, the solubility enhancing group is a trialkyl amine.

In yet an even further embodiment, the solubility enhancing group is cationic.

In still yet an even further embodiment, the solubility enhancing group is anionic.

In still yet an even further embodiment, the molecule is capable of acylating a 2'-hydroxyl group of an RNA polymer resulting in an adduct capable of being removed upon exposure to radiant energy.

In still yet an even further embodiment, the radiant energy is provided by light of approximately 365 nm.

Several embodiments are directed to a method to cloak a RNA polymer. The method includes providing a RNA polymer in a first solution. The method includes adding to the solution a cloaking reagent, wherein the cloaking reagent comprises a leaving group, a photoreleasable protecting group (PPG) and an ester linkage. The PPG is linked to the leaving group via the ester linkage. The addition of the cloaking reagent to the solution results in linking the PPG of the cloaking reagent to a 2'-hydroxyl group of a ribose of the RNA polymer via a carbonate linkage to form a PPG adduct on the RNA polymer.

In another embodiment, the method is performed in a denaturing condition.

In yet another embodiment, the molecular structure of the PPG adduct and carbonate linkage to the RNA polymer is one of:

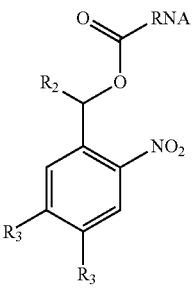

The first adduct is linked to the RNA polymer via a carbonate linkage with the 2'-hydroxyl of ribose; R2 is an alkyl or H; and R3 is an alkoxy or H.

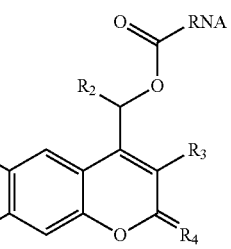

The first adduct is linked to the RNA polymer via a carbonate linkage with the 2'-hydroxyl of ribose; R2 is an alkyl, alkoxy, or H; R3 is an alkyl, aryl, nitro, cyano or H; R4 is (C—R2), O, or S; R5 is an alkoxy, (N—R2), OH, or H; and R6 is a halogen or H.

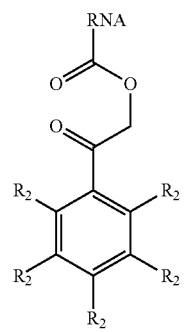

The first adduct is linked to the RNA polymer via a carbonate linkage with the 2'-hydroxyl of ribose; and R2 is an alkyl, alkoxy, nitro, OH, or H.

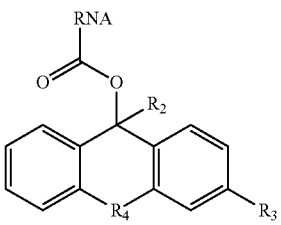

The first adduct is linked to the RNA polymer via a carbonate linkage with the 2'-hydroxyl of ribose; R2 is an aryl or H; R3 is an alkoxy or H; and R4 is O or S.

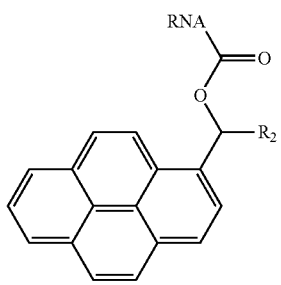

The first adduct is linked to the RNA polymer via a carbonate linkage with the 2'-hydroxyl of ribose; and R2 is an alkyl or H.

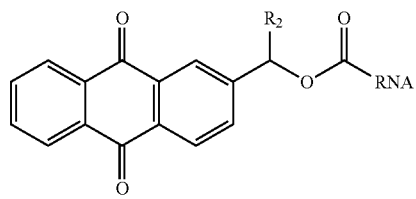

The first adduct is linked to the RNA polymer via a carbonate linkage with the 2'-hydroxyl of ribose; and R2 is an alkyl or H.

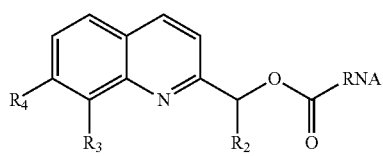

The first adduct is linked to the RNA polymer via a carbonate linkage with the 2'-hydroxyl of ribose; R2 is an alkyl, alkoxy, or H; R3 is a halogen or H; and R4 is an alkoxy, OH, or H.

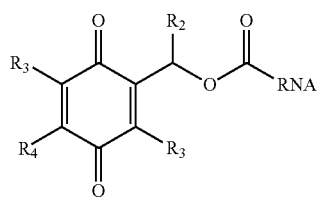

The first adduct is linked to the RNA polymer via a carbonate linkage with the 2'-hydroxyl of ribose; R2 is an alkyl, alkoxy, or H; R3 is an alkyl or H; and R4 is an alkyl, N-alkyl, or H.

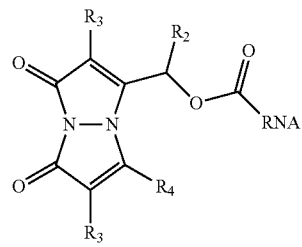

The first adduct is linked to the RNA polymer via a carbonate linkage with the 2'-hydroxyl of ribose; R2 is an alkyl, alkoxy, or H; R3 is an alkyl or H; and R4 is an alkyl, alkoxy, or H.

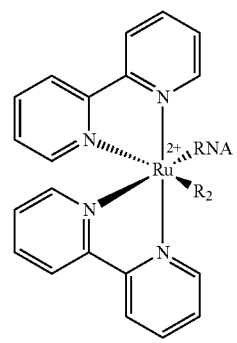

The first adduct is linked to the RNA polymer via a carbonate linkage with the 2'-hydroxyl of ribose; and R2 is an appropriate ligand.

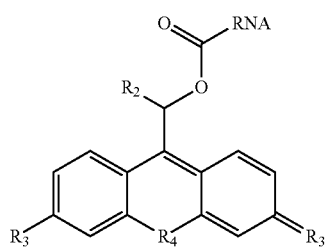

The first adduct is linked to the RNA polymer via a carbonate linkage with the 2'-hydroxyl of ribose; R2 is an alkyl, alkoxy, or H; R3 is an alkoxy, N-alkyl, O, N, or H; and R4 is Si, S, or O. And

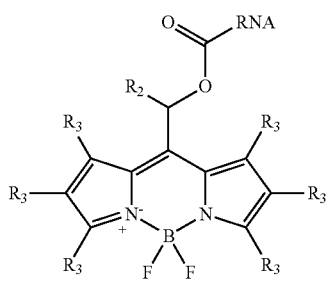

The first adduct is linked to the RNA polymer via a carbonate linkage with the 2'-hydroxyl of ribose; R2 is an alkyl, alkoxy, or H; and R3 is an alkyl, aryl, alkoxy, halogen or H.

In a further embodiment, the PPG adduct further comprises a substituent, and wherein the substituent is a solubility enhancing group.

In still yet another embodiment, the solubility enhancing group is a trialkyl amine.

In yet a further embodiment, the solubility enhancing group is cationic.

In an even further embodiment, the solubility enhancing group is anionic.

In yet an even further embodiment, the addition of the cloaking reagent to the solution results in the RNA polymer being polyacylated with at least a second adduct linked to a 2'-hydroxyl group of a second ribose.

In still yet an even further embodiment, the polyacylated RNA polymer has adducts linked to at least a percentage of the ribosyl 2'-hydroxyl groups, wherein the percentage is selected from a group consisting of: 10%, 20%, 30%, 40%, 50%, 60%, 70%, 80%, and 90%.

In still yet an even further embodiment, the addition of the cloaking reagent to the solution results in every accessible ribosyl 2'-hydroxyl group of the RNA polymer is acylated.

In still yet an even further embodiment, the RNA polymer is longer than a length select from a group consisting of: 200 nucleotides (nt), 300 nt, 400 nt, 500 nt, 600 nt, 700 nt, 800 nt, 900 nt, 1000 nt, 2000 nt, and 3000 nt.

In still yet an even further embodiment, the RNA polymer is derived from an in vivo source.

In still yet an even further embodiment, the RNA polymer is derived from an in vitro method.

In still yet an even further embodiment, the in vitro method is one of: RNA polymerase extension and oligomeric synthesis.

In still yet an even further embodiment, the linking of the PPG to the RNA polymer mitigates a function of the polymer.

In still yet an even further embodiment, the function is one of: hybridization, secondary structure formation, mRNA translation, and protein interaction.

In still yet an even further embodiment, the resulting acylated RNA polymer is utilized in a medicament.

In still yet an even further embodiment, the leaving group is selected from a group consisting of: midazole, triazol, tetrazole, azide, nitryl, N-hydroxysuccinimide and ester.

In still yet an even further embodiment, the leaving group is further substituted.

In still yet an even further embodiment, the PPG has an aromatic core. In still yet an even further embodiment, the cloaking reagent has a molecular structure selected from the following structures:

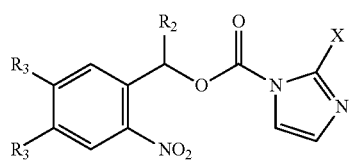

Such that X is a halogen or H; R2 is an alkyl or H; and R3 is an alkoxy or H.

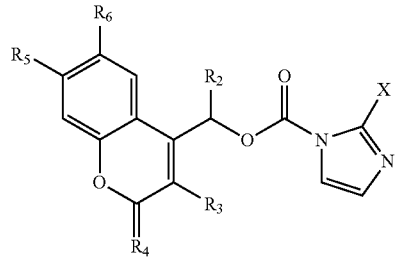

Such that X is a halogen or H; R2 is an alkyl, alkoxy, or H; R3 is an alkyl, aryl, nitro, cyano or H; R4 is (C—R$_2$), O, or S; R5 is an alkoxy, (N—R$_2$), OH, or H; and R6 is a halogen or H.

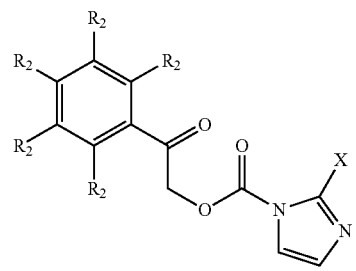

Such that X is a halogen or H; and R2 is an alkyl, alkoxy, nitro, OH, or H.

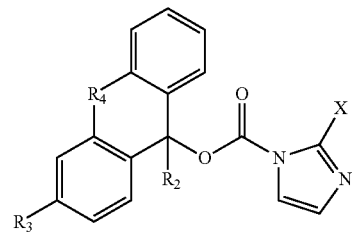

Such that X is a halogen or H; R2 is an aryl or H; R3 is an alkoxy or H; and R4 is O or S.

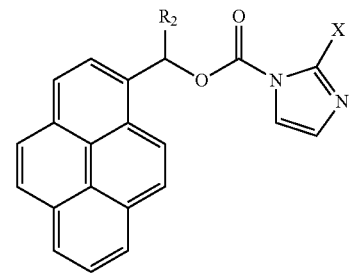

Such that X is a halogen or H; and R2 is an alkyl or H.

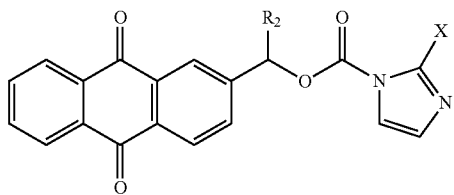

Such that X is a halogen or H; and R2 is an alkyl or H.

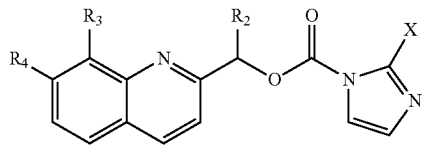

Such that X is a halogen or H; R2 is an alkyl, alkoxy, or H; R3 is a halogen or H; and R4 is an alkoxy, OH, or H.

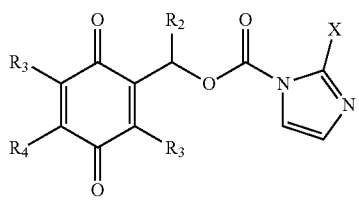

Such that X is a halogen or H R2 is an alkyl, alkoxy, or H; R3 is an alkyl or H; and R4 is an alkyl, N-alkyl, or H.

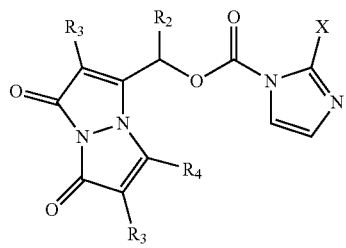

Such that X is a halogen or H; R2 is an alkyl, alkoxy, or H; R3 is an alkyl or H; and R4 is an alkyl, alkoxy, or H.

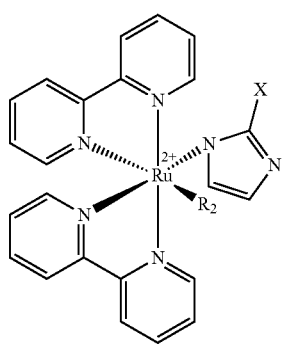

Such that X is a halogen or H; and R2 is an appropriate ligand.

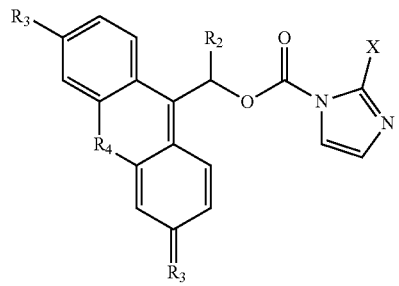

Such that X is a halogen or H; R2 is an alkyl, alkoxy, or H; R3 is an alkoxy, N-alkyl, O, N, or H; and R4 is Si, S, or O. And

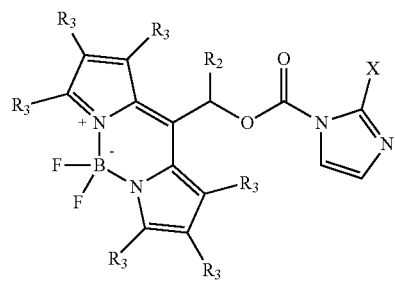

Such that X is a halogen or H; R2 is an alkyl, alkoxy, or H; and R3 is an alkyl, aryl, alkoxy, halogen or H.

In still yet an even further embodiment, the cloaking reagent further comprises a substituent, and wherein the substituent is a solubility enhancing group.

In still yet an even further embodiment, the solubility enhancing group is a trialkyl amine.

In still yet an even further embodiment, the solubility enhancing group is cationic.

In still yet an even further embodiment, the solubility enhancing group is anionic.

In still yet an even further embodiment, the method further applies radiant energy to the solution such that he radiant energy results in removal of the PPG adduct from the RNA polymer.

In still yet an even further embodiment, the radiant energy is provided by a light of approximately 365 nm.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIGS. 5A-5C provide nuclear magnetic resonance and mass spectrometry data of intermediate 3b, generated in accordance with various embodiments of the invention.

FIGS. 7A-7C provide nuclear magnetic resonance and mass spectrometry data of intermediate 4b, generated in accordance with various embodiments of the invention.

FIGS. 8A-8C provide nuclear magnetic resonance and mass spectrometry data of intermediate 5a, generated in accordance with various embodiments of the invention.

FIGS. 9A-9C provide nuclear magnetic resonance and mass spectrometry data of intermediate 5b, generated in accordance with various embodiments of the invention.

FIGS. 11A & 11B provide nuclear magnetic resonance and mass spectrometry data of photocloaking agent 2, generated in accordance with various embodiments of the invention FIG. 12 provides molecular structure diagram various photocloaking reagents with alternative leaving groups in accordance with various embodiments of the invention.

DETAILED DESCRIPTION

Figure 1A:
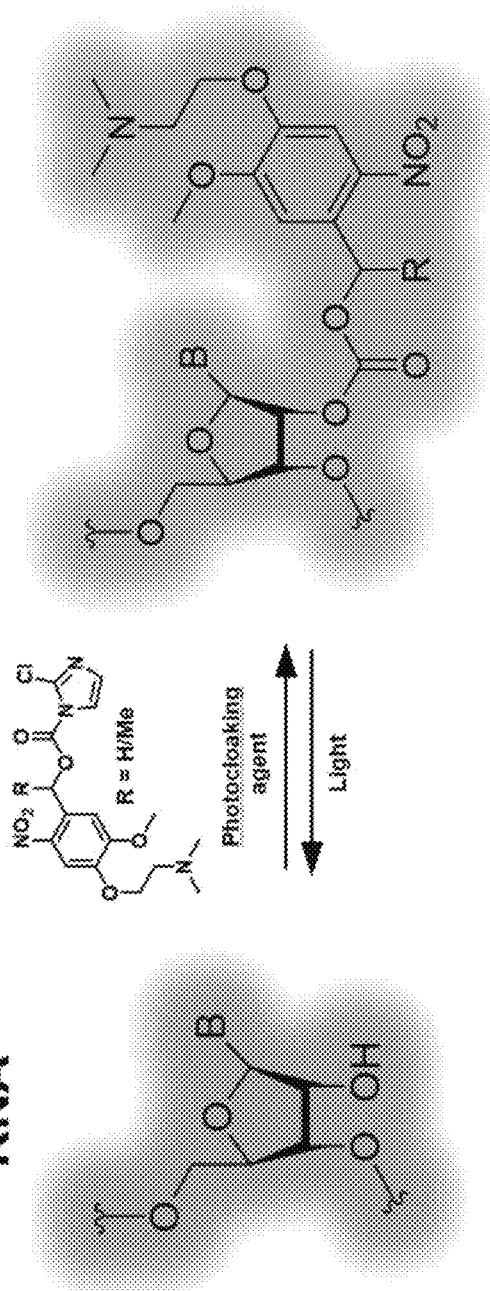
FIGS. 1A and 1B provide diagrams of a photocloaking and uncloaking reaction mechanism, utilized in accordance with various embodiments of the invention.

Turning now to the drawings and data, photoreversible acylation reagents, methods to controllably cloak and uncloak RNA, products thereof and applications thereof are provided. In several embodiments, RNA polymers are cloaked using an acylation reagent. Cloaking of RNA molecule can provide several benefits, including controlling the activity of an RNA molecule. Accordingly, when an RNA polymer is cloaked, the polymer's activity is mitigated, and in some cases, completely inhibited. In several embodiments, cloaked RNA polymers are uncloaked using radiant energy, allowing the RNA polymer to function. By controlling the cloaking and uncloaking steps, the activity of an RNA polymer is manipulated.

Many embodiments are directed to acylated RNA polymers and collections of acylated RNA polymers. In various embodiments, the acylation alters RNA polymer activity, such as, for example, inhibition of secondary structure formation. Some embodiments are directed to cloaking RNA polymers using photolabile reagents that selectively acylate RNA on the ribosyl 2'-hydroxyl (2'-OH) group. Other embodiments are directed to uncloaking cloaked RNA using radiant energy that can selectively deacylate an acylated RNA polymer. In further embodiments, the uncloaking of RNA polymers can activate a function, binding of another molecule, or formation of a secondary structure.

Control of RNA Activity

RNA is a highly versatile biological macromolecule, carrying out a diverse range of cellular functions including gene expression, catalysis, and cell signaling among other functions (B. A. Armitage *Curr. Opin. Chem. Biol.* 2011, 15, 806-12, the disclosure of which is incorporated herein by reference). In recent years, research has uncovered many additional properties and applications of RNA modulation of signaling pathways by circular RNAs, RNA epigenetics and RNA nanobiology (See, e.g., T. R. Cech and J. A. Steitz Cell 2014, 157, 77-94; C. He Nat. Chem. Biol. 2010, 6, 863; L. Chen Nat. Rev. Mol. *Cell Biol.* 2016, 17, 205-11; and C. J. Delebecque, et al. *Science* 2011, 333, 470-74; the disclosures of which are each incorporated herein by reference). Due to the complexity of RNA biology, there is a high demand for chemical tools to study functions and properties of RNA.

One important way to gather insight into RNA's biological role is by exerting external control over its function (A. S. Lubbe, W. Szymanski, and B. L. Feringa *Chem. Soc. Rev.* 2017, 46, 1052-79; and C. Brieke, et al. *Angew Chem. Int. Ed. Engl.* 2012 51, 8446-76; the disclosures of which are each incorporated herein by reference). By turning on the function of an RNA within a complex cellular environment, its role in interacting and exerting downstream effects can be studied in detail. External control can be obtained by introducing labels into RNA that will perturb its natural state and function and that can be removed on demand. This has been achieved in multiple laboratories by introducing photoreleasable protecting groups (PPGs or photocaging groups) into RNA that can be removed after light exposure (See, e.g., N. Ankenbruck, N., et al. *Angew Chemie Int. Ed.* 2017, DOI: 10.1002/anie.201700171; J. M. Govan, J. M., et al. *Nucleic Acids Res.* 2013, 41, 10518-28; V. Mikat, and A. Heckel *RNA* 2007, 13, 2341-47; T. Lucas, et al. *Nat. Commun.* 2017, 8, 15162; S. G. Chaulk, and A. M. MacMillan *Nat. Protoc.* 2007, 2, 1052-58; Y. Matsushita-Ishiodori, and T. Ohtsuki *Acc. Chem. Res.* 2012, 45, 1039-47; S. Shah, S., S. Rangarajan, and S. H. Friedman *Angew. Chem. Int. Ed.* 2005, 117, 1352-56; A. Meyer and A. Mokhir *Angew Chem. Int. Ed.* 2014, 53, 12840-43; J. Lu, et al. *Nucleosides Nucleotides Nucleic Acids* 2015, 3, 114-29; M. J. Resendiz, et al. *J. Am. Chem. Soc.* 2012, 134 (30), 12478-81; S. Panja, et al. *Angew Chem. Int. Ed.* 2015, 54, 7281-84; C. Höbartner and S. K. Silverman *Angew. Chem. Int. Ed.* 2005, 44, 7305-09; and A. Gautier, et al. *Nat. Chem. Biol.* 2014, 10, 533-41; the disclosures of which are each incorporated herein by reference).

A common method for obtaining photocontrolled RNA is by use of photocage-bearing phosphoramidites that are introduced into RNA by solid-phase synthesis (See Q. Liu and A. Deiters *Acc. Chem. Res.* 2014, 47, 45-55, the disclosure of which is incorporated herein by reference). Synthesis of the modified nucleotides is labor intensive and requires DNA synthesizers for their incorporation into RNA. Thus, it may be difficult for biologists to access this technology easily or cheaply. Also important is that limitations of solid-phase RNA synthesis require that the PPGs be applied only in relatively short RNAs, despite the fact that most biological RNAs are commonly hundreds or thousands of nucleotides in length. One approach to overcoming this size limitation was reported by Okamoto and coworkers who developed diazoketones carrying PPGs that react with RNA backbone phosphodiester groups to yield phosphotriesters (H. Ando, et al. *Nat. Genet.* 2001, 28, 317-25). Follow-up studies utilizing this approach, however, revealed that this approach was problematic due to the known instability of the phosphotriester adducts, which hydrolyze to cause RNA strand cleavage (See R. A. Blidner, et al., *Mol. Biosyst.*, 2008, 4, 431-40).

To address these obstacles, embodiments described herein were developed to achieve a facile and more accessible method that can be applied post-synthetically to any RNA molecule, including (but not limited to) synthetic, natural, in vitro, and ex vivo molecules, regardless of strand length. In previous studies, it was discovered that 2'-OH groups of RNA can be selectively reacted in aqueous buffers with activated acyl compounds in structure mapping experiments (R. C. Spitale, et al. *Nature* 2015, 519, 486-90; R. C. Spitale, et al., *Nat. Chem. Biol.* 2013, 9, 18-20; E. J. Merino, et al. *J. Am. Chem. Soc.* 2005, 127, 4223-31; J. T. Low and K. M. Weeks *Methods* 2010, 52, (2), 150-58; the disclosures of which are each incorporated herein by reference). Here, however, and in accordance with several embodiments, novel strategies in which PPGs can be conjugated to 2' hydroxyls of RNA to block structure and interactions, but also render it photoresponsive by including photocleavable bonds (e.g., carbonate), were developed. In many embodiments, addition of several photoresponsive, blocking groups to an RNA molecule covers and protects (i.e., cloaks) the molecule to prevent it from folding and/or interacting with other molecules. In a number of embodiments, subsequently exposing a cloaked RNA molecule to radiant energy switches on functional activity, triggering RNA folding, interactions with other molecules, and ensuing biological activity.

Described herein are embodiments of the invention directed to facile and generally applicable approaches for obtaining photoprotected RNA by a single, short treatment with carefully designed acylating agents. Accordingly, various embodiments described within detail versatile strategies for covalent derivatization and blocking of RNA, by use of multiple acylations at ribose 2'-OH groups of RNA polymers. In many embodiments, the design and synthesis of a number of acylating reagents include a nitroveratryl core with substitutions meant to tune reactivity and solubility. Incubation of photocloaking acylating reagents with RNAs in vitro, in accordance with numerous embodiments, allow selective, high-yield labeling of RNAs in aqueous buffer, to yield various embodiments of acylated ("cloaked") RNA polymers having at least one photocloaking adduct on a RNA molecule. In many embodiments, a photocloaking adduct is attached to the RNA molecule by a carbonate bond, linked to a 2'-OH of RNA. In numerous embodiments, acylation ("cloaking") can block RNA folding, small molecule binding, hybridization, ribozyme activity and/or enzyme recognition. In a number of embodiments, photocloaking reagents do not appreciably react with DNA molecules, as these molecules lack a hydroxyl group on the 2'-carbon of the ribose sugars (i.e., 2'-OH).

Numerous embodiments are also directed to restoring an acylated RNA to its unmodified, native form by bioorthogonal deacylation ("uncloaking") by exposing the cloaked RNA to radiant energy (e.g., light). In a number of embodiments, uncloaking reactions can be utilized as a temporal switch to activate RNA activity. In several embodiments, uncloaking of RNA polymers can be performed in either in vitro or in vivo (e.g., living human cells) conditions. Thus, a number of cloaking embodiments enable temporal control of RNA activity and application (e.g., expression, folding) that is near-completely reversible in either in vitro or in vivo conditions.

Cloaking and Uncloaking Reactions

Several embodiments are directed to methods to acylate an RNA polymer such that it is "cloaked." In many embodiments, a cloaked RNA polymer has at least one acyl group containing photoresponsive blocking groups covalently linked to the 2'-OH of at least one ribose sugar of the polymer such that the photoresponsive-containing adduct is photoreleasable (i.e., uncloakable) upon light stimulation. In numerous embodiments, an acyl group is linked to a RNA molecule via a carbonate linkage.

Figure 1B:
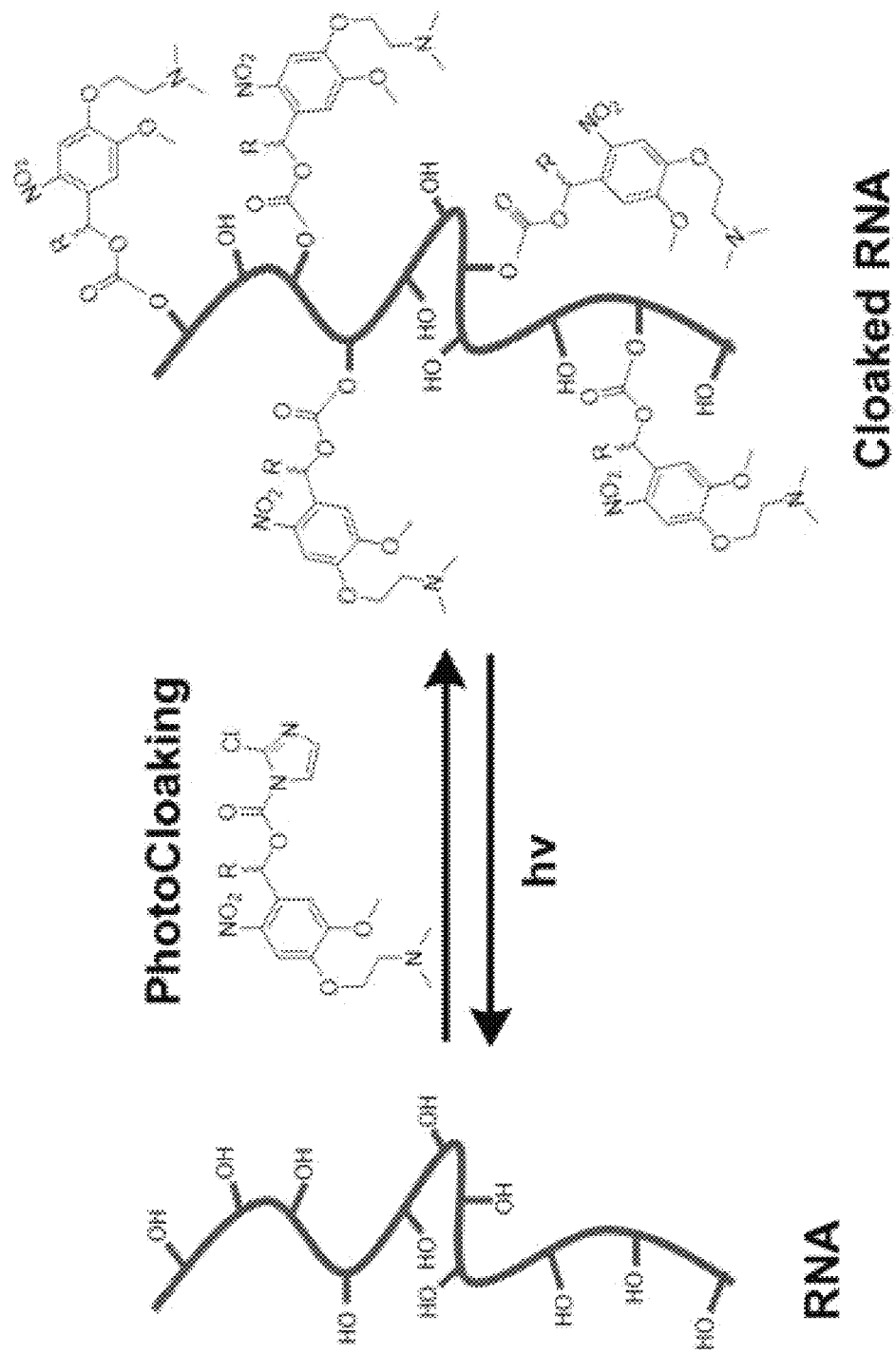

Depicted in FIG. 1A are cloaking and uncloaking reactions in accordance with various embodiments of the invention. As seen in the figure, embodiments are directed to photoresponsive molecules capable of covalently linking to a 2'-OH of RNA polymers via acylation. In many embodiments, a reactive leaving group (e.g., imidazole) facilitates formation of a carbonate linkage between the ribose sugar of the RNA and a linker of the azide-containing molecule. As depicted in FIG. 1B, multiple cloaking reactions occur on an RNA polymer to form a polyacylated RNA polymer in accordance with a number of embodiments. Various embodiments, however, are directed to a single cloaking reaction occurring on an RNA polymer to form a monoacylated RNA polymer.

In several embodiments, acylation of RNA with photocloaking reagents can be carried out conveniently in a single step, yielding high loading of acyl groups on RNA. Photocloaking reagents react with strong selectivity at single-stranded regions of RNA over double-stranded regions due to steric occlusion of the reagent near 2'-OH groups in the A-form helix. This has an important consequence: namely, embodiments of single-stranded RNAs that are cloaked would be hindered from forming duplexes by the sterics of the 2'-O-acyl group. In some embodiments, the cloaking reaction is inefficient on the terminal hydroxyl groups of DNA and other nucleic acids. This inefficiency of cloaking terminal hydroxyl groups of DNA compared to 2'-OH groups of ribose may be attributed to its lower pKa, which is approximately 12-13 as compared with terminal hydroxyl groups in DNA that are likely closer to 15. (See, e.g., I. Velikyan, et al. *J. Am. Chem. Soc.* 2001, 123, 2893-94; S. Accharya, A. Foldesi, and J. Chattopadhyaya *J. Org. Chem.* 2003, 68, 1906-10; the disclosures of which are each incorporated herein by reference.) The lower pKa of the 2'-OH increases the population of its anionic form, greatly enhancing reactivity. Similar pKa-selective effects have been observed for reagents that react selectively with the terminal amine group over lysine sidechain amines in proteins. (See, e.g., J. M. Gilmore, et al. *Angew. Chem. Int. Ed.* 2006, 45, 5307-11, the disclosure of which is incorporated herein by reference.) In many embodiments, the resulting acyl esters are stable over weeks of storage in aqueous buffer at −20° C. in the dark and readily surviving isolation by precipitation.

Many embodiments are directed to cloaking strategies with high degrees of acylation, utilizing photoreactive acylating reagents. Accordingly, various embodiments are directed to photocloaking methods that result in collections of RNA polymers wherein a majority of the polymers have at least one photoreactive acyl adduct covalently linked to the 2'-OH groups. Likewise, embodiments are also directed to collections of RNA polymers wherein a majority of the polymers have at least one photoreactive adduct covalently linked to the 2'-OH groups. In various embodiments, a cloaking reaction can acylate over 10%, 20%, 30%, 40%, 50%, 60%, 70%, 80%, or 90% of the 2'-OH groups in on a single RNA polymer. Embodiments are also directed to the ability of cloaking reagents to acylate every accessible 2'-OH (i.e., 2'-OH of nucleotides unpaired to a complementary base) of an RNA polymer.

In several embodiments, a photocloaking reaction is performed in denaturing conditions (e.g., low ionic strength and/or high temperatures). Denaturing conditions can prevent RNA molecules from hybridization (both self- and nonself-hybridization) and forming secondary structures. Since hybridization and secondary structures can sterically occlude 2'-OH groups, the use of denaturing conditions would open up 2'-OH sites that can be acylated. Accordingly, embodiments are directed to the ability of acylating RNA at 2'-OH sites that would be unavailable in naturally occurring ionic conditions and temperatures (i.e., typical conditions in a biological cell).

In many embodiments, a cloaking reaction results in a RNA polymer acylated with adducts on at least one 2'-OH of the RNA polymer. In numerous embodiments, a cloaking reaction results in a collection of RNA polymers having a majority of the RNA polymers that are acylated with adducts on at least one 2'-OH of the RNA polymers. In many embodiments, an adduct attached at least one 2'-OH of the RNA polymers is a PPG. In some embodiments, a PPG has an aromatic core having various substituents. In some embodiments, a PPG is linked to a 2'OH group of a ribose sugar of RNA via a carbonate linkage. A number of PPGs are known in the art and can be used to protect the ester linkage.

A plurality of embodiments is also directed towards stable acylated RNA polymers having a length greater than achievable by other current methods (e.g., nucleoside phosphoramidite synthesis). Photocloaking methods, as described herein, can cloak any RNA molecule of any length. Accordingly, various embodiments are directed to stable acylated RNA polymers of over: 200 nucleotides (nt), 300 nt, 400 nt, 500 nt, 600 nt, 700 nt, 800 nt, 900 nt, 1000 nt, 2000 nt, 3000 nt, and longer.

In a number of embodiments, an adduct is further substituted with other groups for various effects, such as solubility. In several embodiments, a solubility substituent is included in the adduct. In numerous embodiments, a solubility substituent has a structure (e.g., trialkyl amine) such that it is protected from unwanted reactivity with RNA chains and most other molecules it may encounter. It is noted that either cationic or anionic solubility-enhancing substituents may be used in accordance with multiple embodiments, but in some embodiments, it may be preferred to utilize a cationic substituent that would naturally attract to the anionic phosphate backbone of RNA.

Several various embodiments of PPGs exist. In many embodiments, an acylated RNA has a PPG adduct with the following structure:

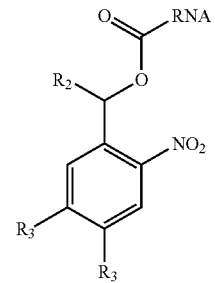

and the adduct is linked to an RNA polymer via a carbonate linkage with the 2'-OH of ribose; R2 is an alkyl or H; and R3 is an alkoxy or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylated RNA has a PPG adduct with the following structure:

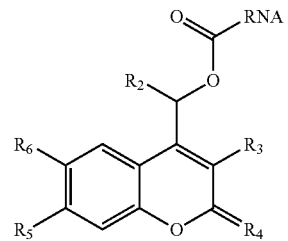

and the adduct is linked to an RNA polymer via a carbonate linkage with the 2'-OH of ribose; R2 is an alkyl, alkoxy, or H; R3 is an alkyl, aryl, nitro, cyano or H; R4 is (C—R₂), O, or S; R5 is an alkoxy, (N—R₂), OH, or H; and R6 is a halogen or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylated RNA has a PPG adduct with the following structure:

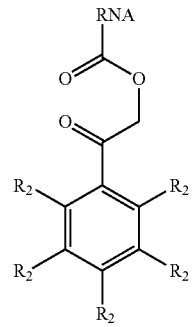

and the adduct is linked to an RNA polymer via a carbonate linkage with the 2'-OH of ribose; and R2 is an alkyl, alkoxy, nitro, OH, or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylated RNA has a PPG adduct with the following structure:

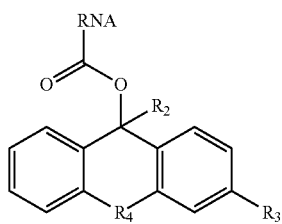

and the adduct is linked to an RNA polymer via a carbonate linkage with the 2'-OH of ribose; R2 is an aryl or H; R3 is an alkoxy or H; and R4 is O or S. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylated RNA has a PPG adduct with the following structure:

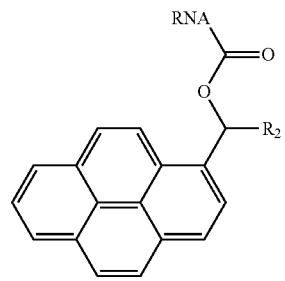

and the adduct is linked to an RNA polymer via a carbonate linkage with the 2'-OH of ribose; and R2 is an alkyl or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylated RNA has a PPG adduct with the following structure:

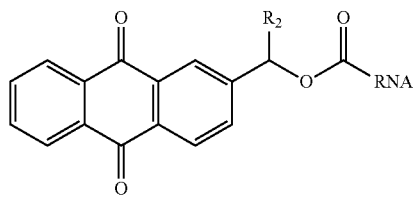

and the adduct is linked to an RNA polymer via a carbonate linkage with the 2'-OH of ribose; and R2 is an alkyl or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylated RNA has a PPG adduct with the following structure:

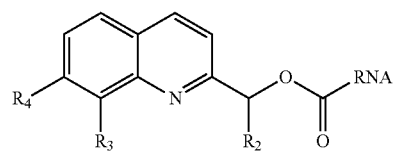

and the adduct is linked to an RNA polymer via a carbonate linkage with the 2'-OH of ribose; R2 is an alkyl, alkoxy, or H; R3 is a halogen or H; and R4 is an alkoxy, OH, or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylated RNA has a PPG adduct with the following structure:

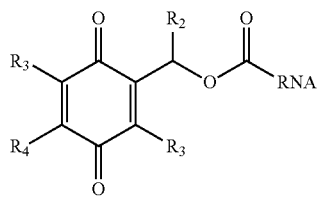

and the adduct is linked to an RNA polymer via a carbonate linkage with the 2'-OH of ribose; R2 is an alkyl, alkoxy, or H; R3 is an alkyl or H; and R4 is an alkyl, N-alkyl, or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylated RNA has a PPG adduct with the following structure:

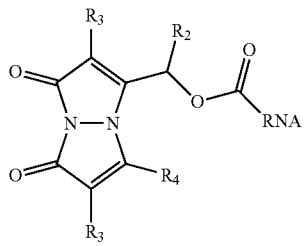

and the adduct is linked to an RNA polymer via a carbonate linkage with the 2'-OH of ribose; R2 is an alkyl, alkoxy, or H; R3 is an alkyl or H; and R4 is an alkyl, alkoxy, or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylated RNA has a PPG adduct with the following structure:

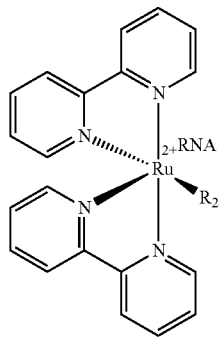

and the adduct is linked to an RNA polymer via a carbonate linkage with the 2'-OH of ribose; and R2 is an appropriate ligand, such as, for example, 4-aminopyridine, butylamine, serotonin, tryptamine, and tyramine. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylated RNA has a PPG adduct with the following structure:

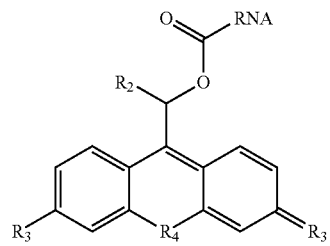

and the adduct is linked to an RNA polymer via a carbonate linkage with the 2'-OH of ribose; R2 is an alkyl, alkoxy, or H; R3 is an alkoxy, N-alkyl, O, N, or H; and R4 is Si, S, or O. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylated RNA has a PPG adduct with the following structure:

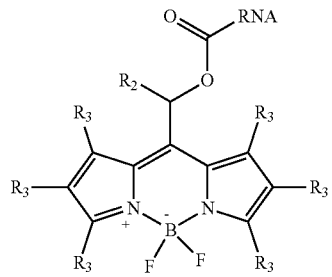

and the adduct is linked to an RNA polymer via a carbonate linkage with the 2'-OH of ribose; R2 is an alkyl, alkoxy, or H; and R3 is an alkyl, aryl, alkoxy, halogen or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In a multitude of embodiments, a collection of RNA is at least two RNA polymers, which may be cloaked or uncloaked. Collections of RNA can be sourced from any appropriate points of supply, comprised of an unlimited combination of RNA molecules, and exist in a number of conditions. In several embodiments, a collection of RNA is extracted from an in vivo source, such as biological cell or animal tissue. In many embodiments, collections can be derived by in vitro methods, such as an RNA polymerase or oligomeric synthesis (e.g., phosphoramidite synthesis).

In a number of embodiments, a collection of RNA includes RNA polymers all having the same sequence. In many embodiments, a collection comprises RNA polymers of multiple sequences. In several embodiments, a collection comprises RNA polymers that make up a full or partial transcriptome.

Various embodiments of RNA collections exist in an aqueous solution, however any appropriate solution for RNA storage may be used. In a multitude of embodiments, a collection of RNA is lyophilized and stored as a solid substance.

Embodiments are also directed to removal of acylated adducts when radiant energy is exposed upon the RNA molecule, resulting in cleavage of the ester linkage in to revert the linkage to a 2'-OH on the RNA ribose (i.e., uncloaking) (FIGS. 1A and 1B). In a number of embodiments, the radiant energy used to cleave the adduct with light having a wavelength around 365 nanometers. It should be understood, that the optimal radiant energy reaction can be optimized dependent on the adduct utilized and the application. Accordingly, it should be understood that the light wavelength, intensity, and time of exposure can be altered and still fall within various embodiments of the invention. The ability to remove RNA adducts in a photo-induced uncloaking reaction gives rise to various embodiments of controlled, reversible cloaking of RNA polymers. Accordingly, embodiments are directed to "switching on" RNA function via a photo-induced uncloaking reaction.

Applications of RNA Acylation and Deacylation

The currently described chemical cloaking strategy for RNA can be used in multiple applications. In several embodiments, the cloaking strategy results in acylated RNA polymers having an ability to block hybridization, folding, protein translation or intermolecular interactions.

Inhibition of RNA hybridization has several applications. Hybridized RNA polymers are known to be involved in a number of biological processes, including, but not limited to, RNA interference, stimulation of the immune system, and RNA degradation by RNase H. Accordingly, various embodiments are directed to cloaked RNA to inhibiting various phenomena utilizing its ability to inhibit RNA hybridization. In many embodiments, cloaked RNAs can be siRNAs, miRNAs, shRNAs, circRNAs, antisense RNAs, ribozymes, or riboswitches, depending on the appropriate application.

Numerous classes of RNA polymers fold into secondary structures to perform a specific function. Examples of RNA polymers that rely on secondary structures to perform their function include, but are not limited to, tRNAs, rRNAs, snRNAs, snoRNA, aptamers, and guide RNAs used in CRISPR/Cas9 applications. Accordingly, a multitude of embodiments are directed to cloaking an RNA polymer to inhibit its function by inhibiting formation of RNA secondary structure.

Messenger RNA (mRNA) polymers constitute a major class of RNA polymers that relay the genetic information from a cell's DNA to the ribosomes to construct proteins. Cloaking mRNA polymers can inhibit ribosomes' ability to translate the cloaked mRNA sequence into proteins. Accordingly, several embodiments are directed to inhibiting protein production of cloaked RNAs.

As described in the preceding section, application of radiant energy to cloaked RNA polymers results in removal of photoreleasable adducts, restoring RNA to its native form. This ability to photochemically uncloak the cloaked RNA polymers can be employed to temporally control various abilities of the polymers. Accordingly, a number of embodiments are directed to temporal control of RNA structure, interaction, and/or function.

Cloaking of RNA polymers can inhibit hybridization, secondary structure formation, mRNA translation, and protein interaction. Therefore, these functions can be temporally controlled using a cloaking/uncloaking technique as described within. It should be understood that the above-described functions are not exhaustive and this cloaking/uncloaking strategy could be used in a number of applications in accordance of various embodiments that can take advantage of this technique.

Medicament Formulations and Treatments Thereof

In embodiments, cloaked RNA molecules are formulated into therapeutic medicaments for treatments. Many embodiments are directed to methods of treatment with medicaments containing the cloaked RNA molecules. In some embodiments, the medicament targets disorders that are treatable by controlled activation of RNA molecules. Various embodiments will have medicaments that are capable of activating RNA expression and respective protein production via radiant energy exposure. Some embodiments will have medicaments that activate various enzymes or ribozymes via radiant energy exposure. In a number of embodiments, cloaking of RNA molecules protects and stabilizes RNA, increasing the shelf life of RNA medicaments.

A number of embodiments are directed to methods of medical treatment utilizing RNA acylation and deacylation strategies. In many embodiments, medical conditions are treated via controlled regulation of RNA utilizing photocloaked RNA molecules. In several embodiments, photocloaked RNA is activated by radiant energy in a medical intervention. In some embodiments, the photocloaked RNA is applied to human biological tissue that is subsequently exposed to radiant energy to initiate treatment.

In many such embodiments, modes of administration for various therapeutics include, but are not limited to, oral, transdermal, transmucosal (e.g., sublingual, nasal, vaginal or rectal), or parenteral (e.g., subcutaneous, intramuscular, intravenous, bolus or continuous infusion). The actual amount of drug needed will depend on factors such as the size, age and severity of disease in the afflicted individual. The actual amount of drug needed will also depend on the effective local RNA concentration ranges of various cloaked RNA compounds.

In some embodiments, cloaked RNA compounds are administered in a therapeutically effective amount as part of a course of treatment. As used in this context, to "treat" means to ameliorate at least one symptom of a disorder to be treated or to provide a beneficial physiological effect. For example, one such amelioration of a symptom could result from activation of a cloaked RNA molecule. Assessment of symptom amelioration can be performed in many ways, and would be dependent on the disorder to be treated, as it would be understood to those skilled in the art.

A therapeutically effective amount can be an amount sufficient to prevent reduce, ameliorate or eliminate the symptoms of diseases or pathological conditions susceptible to such treatment. In some embodiments, a therapeutically effective amount is an amount sufficient to induce protein production above a threshold via RNA expression of uncloaked RNA.

Dosage, toxicity and therapeutic efficacy of the compounds can be determined, e.g., by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to healthy tissue and, thereby, reduce side effects.

Data obtained from cell culture assays or animal studies can be used in formulating a range of dosage for use in humans. If a medicament is provided systemically, the dosage of such compounds lies preferably within a range of circulating and/or local concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration or within the local environment to be treated in a range that includes the $IC_{50}$ (i.e., the concentration of the test compound that achieves a half-maximal inhibition) as determined in cell culture. Such information can be used to more accurately determine useful doses in humans. Levels in plasma may be measured, for example, by liquid chromatography coupled to mass spectrometry.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. A skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments. For example, several divided doses may be administered daily, one dose, or cyclic administration of the compounds to achieve the desired therapeutic result. Collections of cloaked RNA having a single sequence may be administered, or collections having combinations of various sequences may also be administered.

It is also possible to add agents that improve the solubility of these compounds. For example, the claimed compounds can be formulated with one or more adjuvants and/or pharmaceutically acceptable carriers according to the selected route of administration. For oral applications, gelatin, flavoring agents, or coating material can be added. In general, for solutions or emulsions, carriers may include aqueous or alcoholic/aqueous solutions, emulsions or suspensions, including saline and buffered media. Parenteral vehicles can include sodium chloride and potassium chloride, among others. In addition, intravenous vehicles can include fluid and nutrient replenishers, electrolyte replenishers and the like.

Preservatives and other additives, like antimicrobial, antioxidant, chelating agents, and inert gases, can also be present. (See generally, Remington's Pharmaceutical Sciences, 16th Edition, Mack, (1980), the disclosure of which is herein incorporated by reference.)

Reagents to Cloak RNA

Numerous embodiments are directed to reagents capable of photoreversible cloaking of RNA polymers via acylation. In several embodiments, a photoreversible cloaking reagent acylates accessible 2'-OH groups (i.e., 2'-OH of nucleotides unpaired to a complementary base) of ribose sugars within RNA polymers. Various embodiments of cloaking reagents preferentially cloak RNA over DNA, which does not have 2'-OH groups. In various embodiments, cloaking reagents have a reactive leaving group (e.g., imidazole) and a PPG such that a cloaking reaction labels RNA with a PPG-containing molecule. In some embodiments, a PPG of the cloaking reagent is connected to the leaving group by a linker. In many embodiments, a PPG provides beneficial chemical properties for the RNA labeling activity. In some of these embodiments, a PPG is bulky to provide steric interference when RNA is labeled.

In several embodiments, acylating reagents are designed such that they can acylate RNA polymer to inhibit RNA function and structure and then subsequently be removed from the RNA to restore its original structure and function. The reagents, in accordance with many embodiments, utilize a radiant energy chemical mechanism for reversal, and thus a PPG reagent must have an appropriate linker so that the radiant energy can precisely remove the PPG adduct. Accordingly, a number of embodiments are also directed to PPG-containing acylation reagents capable of forming a carbonate linkage with an RNA polymer such that it can be removed from the polymer upon exposure to light.

Numerous embodiments are directed to reagents that are soluble in water. Accordingly, various embodiments of photoreversible acylation reagents have solubility enhancing substituents. In many embodiments, a solubility substituent has a structure (e.g., trialkyl amine) such that it is protected from unwanted reactivity with RNA and/or other molecules (especially biomolecules) it may encounter. It is noted that either cationic or anionic solubility-enhancing substituents may be used in accordance with multiple embodiments, but in some embodiments, it may be preferred to utilize a cationic substituent that would naturally attract to the anionic phosphate backbone of RNA.

Many embodiments are directed to PPG molecules having the basic structure:

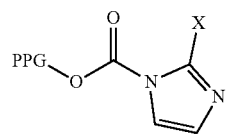

wherein PPG is a photoreleasable protecting group.

In many embodiments, a PPG has an aromatic core having various substituents. A PPG, in accordance with several embodiments, is linked to an imidazole-leaving group via an ester linkage. A number of PPGs are known in the art and can be used in various acylation reagent.

In numerous embodiments, an acylation reagent has a good leaving group. In some embodiments, the leaving group is an imidazole, triazol, tetrazole, azide, nitryl, N-hydroxysuccinimide ester, or a substituted version thereof. In a number of embodiments, the leaving group is an imidazole and has the basic structure:

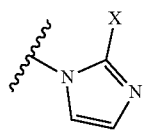

wherein the position 1'-N of the imidazole functionality forms a is covalent bond with the linker group and the position 2'-C of the imidazole functionality is bonded to an atom X, wherein X is a halogen, $NO_2$, CN, methyl or H. In a number of embodiments, X is Cl.

In a number of embodiments, the linker group of an acylation reagent is an ester that covalently connects a leaving group to a PPG. In some embodiments, the linker has the basic structure:

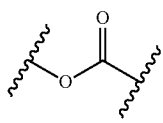 [SMILES: *OC(*)=O]

wherein the carbonyl group is covalently linked to a leaving group and O is covalently linked to a PPG.

In a number of embodiments, a PPG is an organic group having at least an aromatic core. In several embodiments, a PPG is positioned such that it can protect a linkage when formed with an RNA molecule, but release upon radiant energy.

Several various embodiments of PPGs exist. In many embodiments, an acylating reagent has the following structure:

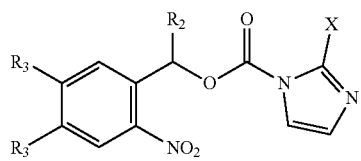

an X is a halogen, $NO_2$, CN, methyl or H; $R_2$ is an alkyl or H; and $R_3$ is an alkoxy or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylating reagent has the following structure:

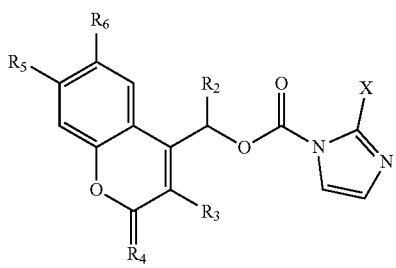

and X is a halogen, $NO_2$, CN, methyl or H; $R_2$ is an alkyl, alkoxy, or H; $R_3$ is an alkyl, aryl, nitro, cyano or H; $R_4$ is $(C-R_2)$, O, or S; $R_5$ is an alkoxy, $(N-R_2)$, OH, or H; and $R_6$ is a halogen or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylating reagent has the following structure:

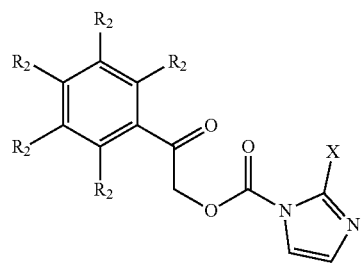

and X is a halogen, $NO_2$, CN, methyl or H; and $R_2$ is an alkyl, alkoxy, nitro, OH, or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylating reagent has the following structure:

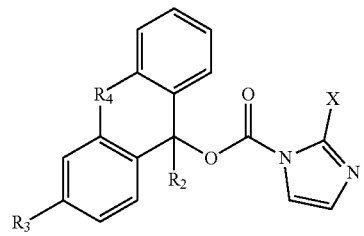

and X is a halogen, $NO_2$, CN, methyl or H; $R_2$ is an aryl or H; $R_3$ is an alkoxy or H; and $R_4$ is O or S. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylating reagent has the following structure:

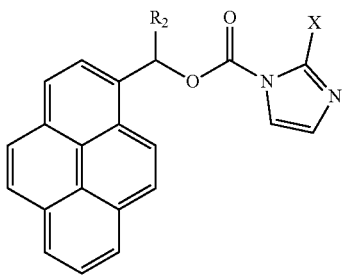

and X is a halogen, NO$_2$, CN, methyl or H; and R2 is an alkyl or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylating reagent has the following structure:

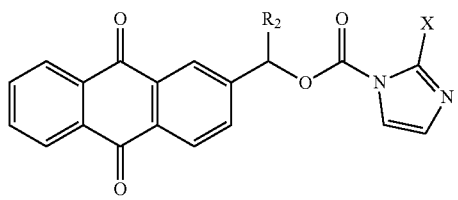

and X is a halogen, NO$_2$, CN, methyl or H; and R2 is an alkyl or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylating reagent has the following structure:

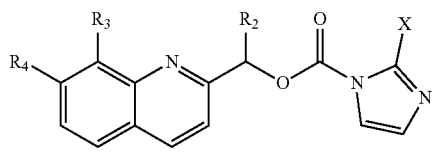

and X is a halogen, NO$_2$, CN, methyl or H; R2 is an alkyl, alkoxy, or H; R3 is a halogen or H; and R4 is an alkoxy, OH, or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylating reagent has the following structure:

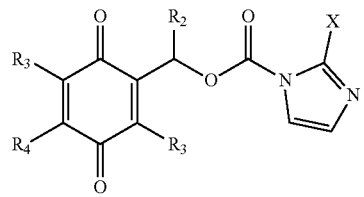

and X is a halogen, NO$_2$, CN, methyl or H; R2 is an alkyl, alkoxy, or H; R3 is an alkyl or H; and R4 is an alkyl, N-alkyl, or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylating reagent has the following structure:

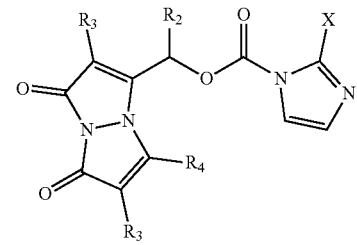

and X is a halogen, NO$_2$, CN, methyl or H; R2 is an alkyl, alkoxy, or H; R3 is an alkyl or H; and R4 is an alkyl, alkoxy, or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylating reagent has the following structure:

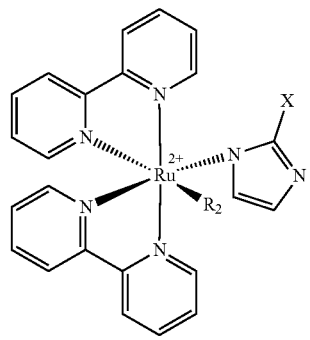

and X is a halogen, NO$_2$, CN, methyl or H; and R2 is an appropriate ligand, such as, for example, 4-aminopyridine, butylamine, serotonin, tryptamine, and tyramine. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylating reagent has the following structure:

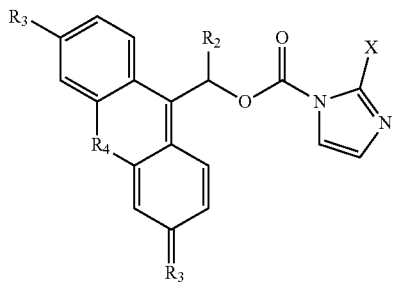

and X is a halogen, $NO_2$, CN, methyl or H; R2 is an alkyl, alkoxy, or H; R3 is an alkoxy, N-alkyl, O, N, or H; and R4 is Si, S, or O. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In many embodiments, an acylating reagent has the following structure:

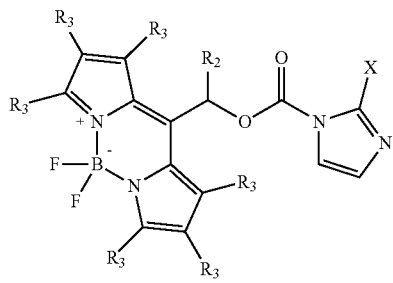

and X is a halogen, $NO_2$, CN, methyl or H; R2 is an alkyl, alkoxy, or H; and R3 is an alkyl, aryl, alkoxy, halogen or H. It should be noted that further substitutions could also be added to the structure, without significantly affecting the PPG activity of the adduct, and still fall within various embodiments of the invention as understood by those skilled in the art. In some embodiments, the adduct is further substituted with a solubility enhancing group.

In several embodiments, a PPG provides beneficial properties to achieve a result desired when covalently linked to a RNA polymer. In many embodiments, a PPG is capable of providing steric interference such that it prevents a RNA polymer from complementary annealing with self or another nucleic acid polymer. In a number of embodiments, a PPG is capable of inhibiting an enzyme from performing enzymatic activity upon a RNA polymer linked to the PPG. In some embodiments, a PPG is capable of inhibiting enzymatic cleavage of a RNA polymer linked to the PPG. Several embodiments are also directed to a PPG capable of inhibiting mRNA translation of a RNA polymer linked to the PPG.

Uncloaking of RNA

A number of embodiments are directed to uncloaking a cloaked RNA polymer via exposure to radiant energy. In several embodiments, exposure to radiant energy at an appropriate wavelength and time course results in cleavage of a carbonate bond, releasing PPG adducts and restoring the RNA polymer to its native form (FIGS. 1A and 1B).

In several embodiments, light of around 365 nm is exposed upon a cloaked RNA to release PPG adducts. In numerous embodiments, a light source to uncloak RNA is provided from a microscope, light emitting diodes (LEDs), broadband light, filtered white light, or similar. It should be understood that the precise wavelength(s), exposure time, light source, and light intensity will depend on the application and the amount of uncloaking to be performed. Accordingly, uncloaking reactions may vary, but still fall within a multitude of embodiments of the invention, as understood by those skilled in the art.

In many embodiments, radiant energy is capable of removing PPG-containing adducts at physiological pH and temperature, where RNA polymers remain stable. In several more embodiments, radiant energy used for deacylation is bioorthogonal and cell-permeable such that it can be used in a cellular environment.

Exemplary Embodiments

The embodiments of the invention will be better understood with the several examples provided within. Many exemplary reagents are provided that are capable of cloaking or uncloaking RNA polymers. Also provided are various exemplary methods that may be utilized to practice the various embodiments. Exemplary experiments using the reagents and methods and the resultant data are also described, further clarifying and enabling one to practice the numerous embodiments. Examples can also be found within the publication entitled "RNA Control by Photoreversible Acylation" of W. A. Velema, A. M. Kierys & E. T. Kool (*J. Am. Chem. Soc.* 2018, 140, 3491-95, the disclosure of which is herein incorporated by reference).

Cloaking Reagents

Numerous cloaking reagents are covered in the various embodiments as described within. The following exemplary embodiments, however, focus on a cloaking reagent having an ortho-nitroveratryl core that serves as the photoprotecting group (See FIG. 2).

Figure 2:
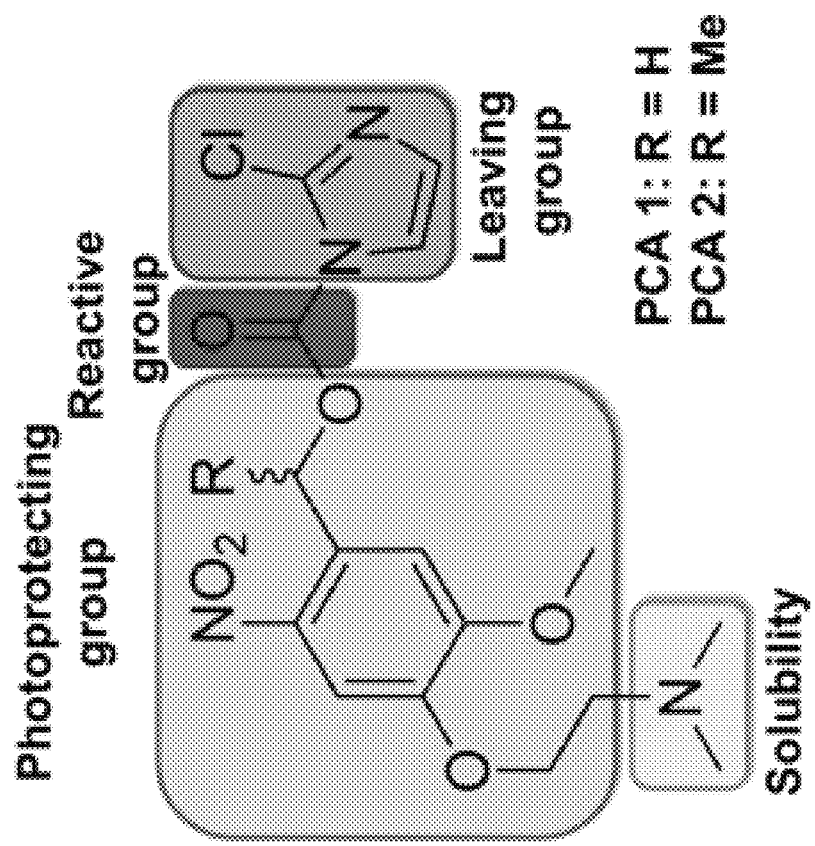
FIG. 2 provides a structure diagram of photocloaking reagents in accordance with various embodiments of the invention.

Design of acylating agents (also referred to as photocloaking agents (PCAs)) began with the knowledge that the 2'-OH groups of RNA exhibit relatively high nucleophilicity due to their low pKa (R. C. Spitale, et al. *Nature* 2015, 519, 486-90; R. C. Spitale, et al. *Nat. Chem. Biol.* 2013, 9, 18-20; E. J. Merino, et al. *J. Am. Chem. Soc.* 2005, 127, 4223-31; and J. T. Low and K. M. Weeks *Methods* 2010, 52, (2), 150-58; the disclosures of which are herein incorporated by reference). For reaction with these nucleophilic groups, it was envisioned the combination of an active acyl group with an ortho-nitroveratryl core that serves as the photoprotecting group, leading to an activated carbonyl ester scaffold (FIG. 2). Although not employed previously on RNA, activated esters of this general type can react with alcohols to form carbonate adducts, which upon photoirradiation, photocleave to restore the alcohol (K. Matsuo, et al. *Chem. Sci.* 2013, 4, 2573-80; and N. . Knežević, B. G. Trewyn, and V. S. Y. Lin *Chem.—A Eur. J.* 2011, 17, 3338-42; the disclosures of which are herein incorporated by reference). Methylated and unmethylated veratryl groups were used for further tests, which are denoted PCA 1 and PCA 2, respectively (FIG. 2); the unmethylated variant (1) is less sterically hindered, while the methylated analogue may have higher efficiency in photocleavage (P. Klan, et al. Chem. Rev. 2013, 11, 119-91. Early experiments revealed that such reagents have limited aqueous solubility; thus a dimethylaminoethyl group was substituted onto the PCAs to enhance solubility. Finally, testing a range of leaving groups (imidazoles and triazoles; (described in detail below), led to the choice of 2-chloroimidazole as having the ideal level of reactivity in water. The net result of this modular design is that these water-soluble reagents have the potential to react with RNA hydroxyl groups, blocking RNA structure and function, and then subsequent potential to be removed by light.

Synthesis of Cloaking Reagents

Figure 3:
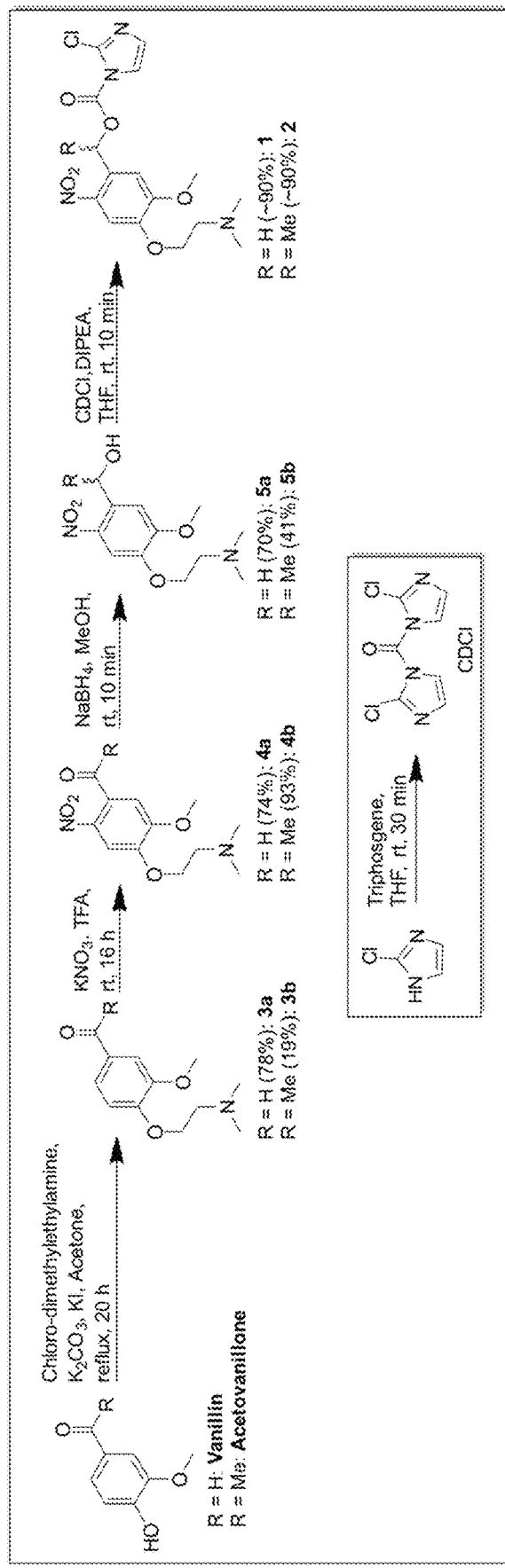
FIG. 3 provides a synthesis diagram for the synthesis of photocloaking reagents in accordance with various embodiments of the invention.

Provided in FIG. 3 is step-by-step synthesis of PCA 1 and PCA 2. To make intermediate 3a 4-(2-(dimethylamino) ethoxy)-3-methoxybenzaldehyde, vanillin (1.52 g, 10 mmol), 2-chloro-dimethylethylamine HCl (2.16 g, 15 mmol), potassium iodide (332 mg, 2 mmol) and potassium carbonate (4.14 g, 30 mmol) were suspended in acetone and heated at reflux for 16 h. Next, volatiles were removed in vacuo and the resulting residue is redissolved in water and ethyl acetate. The organic layer was separated and washed with brine and dried with magnesium sulfate. Concentrating in vacuo resulted in 1.75 g (78%) of a yellow oil.

Figure 4A:
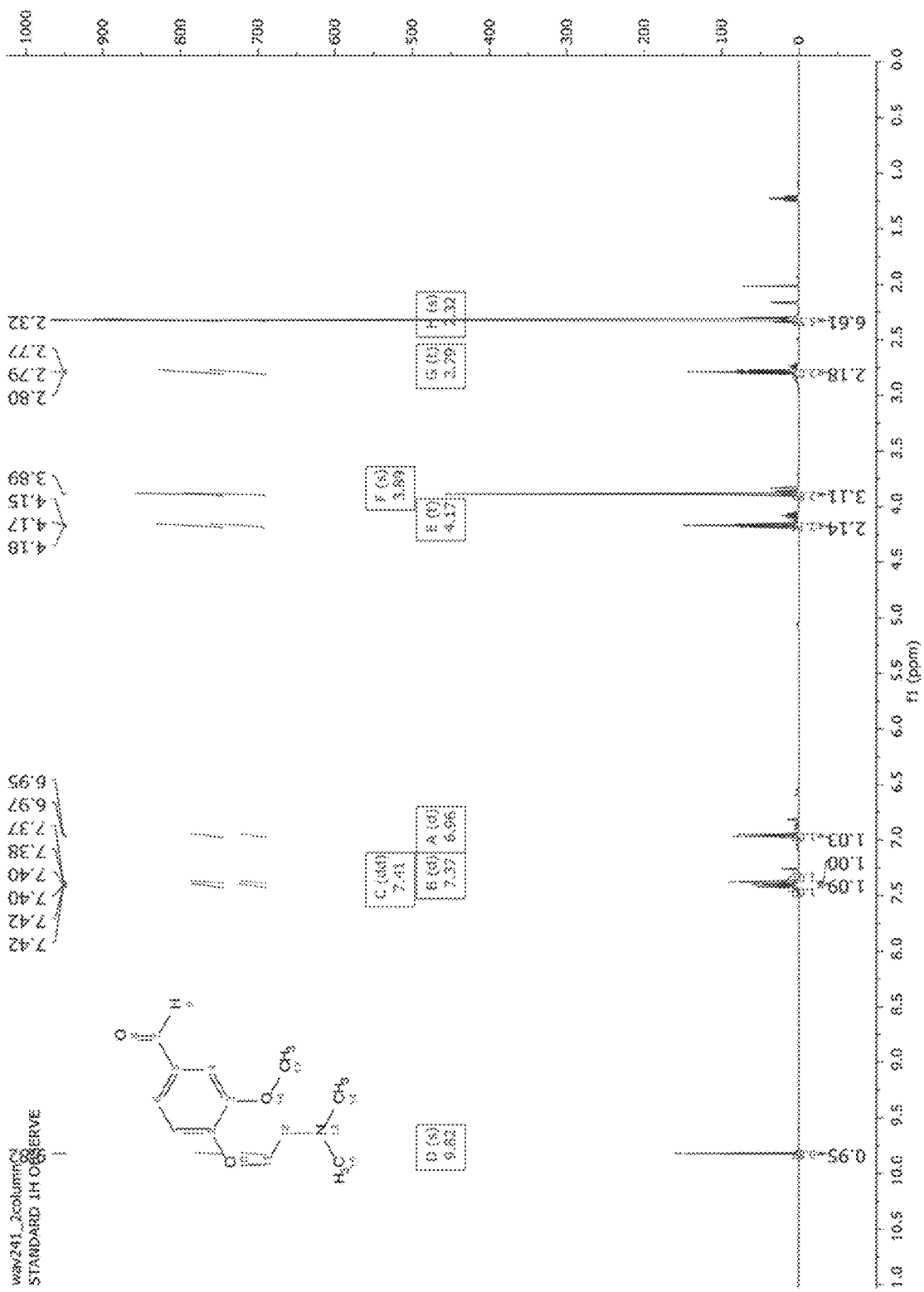
FIGS. 4A-4C provide nuclear magnetic resonance and mass spectrometry data of intermediate 3a, generated in accordance with various embodiments of the invention.
Figure 4B:
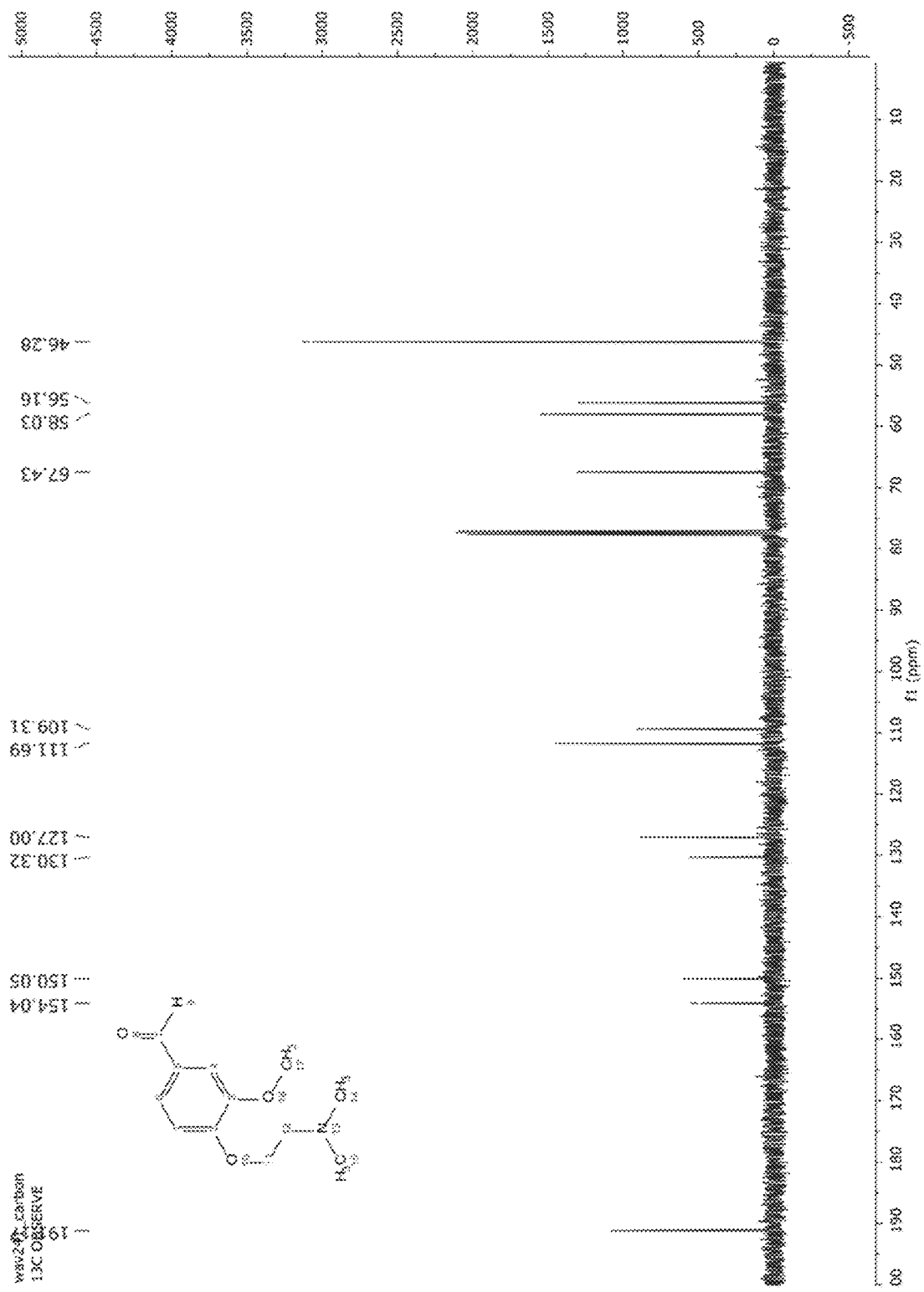
Figure 4C:
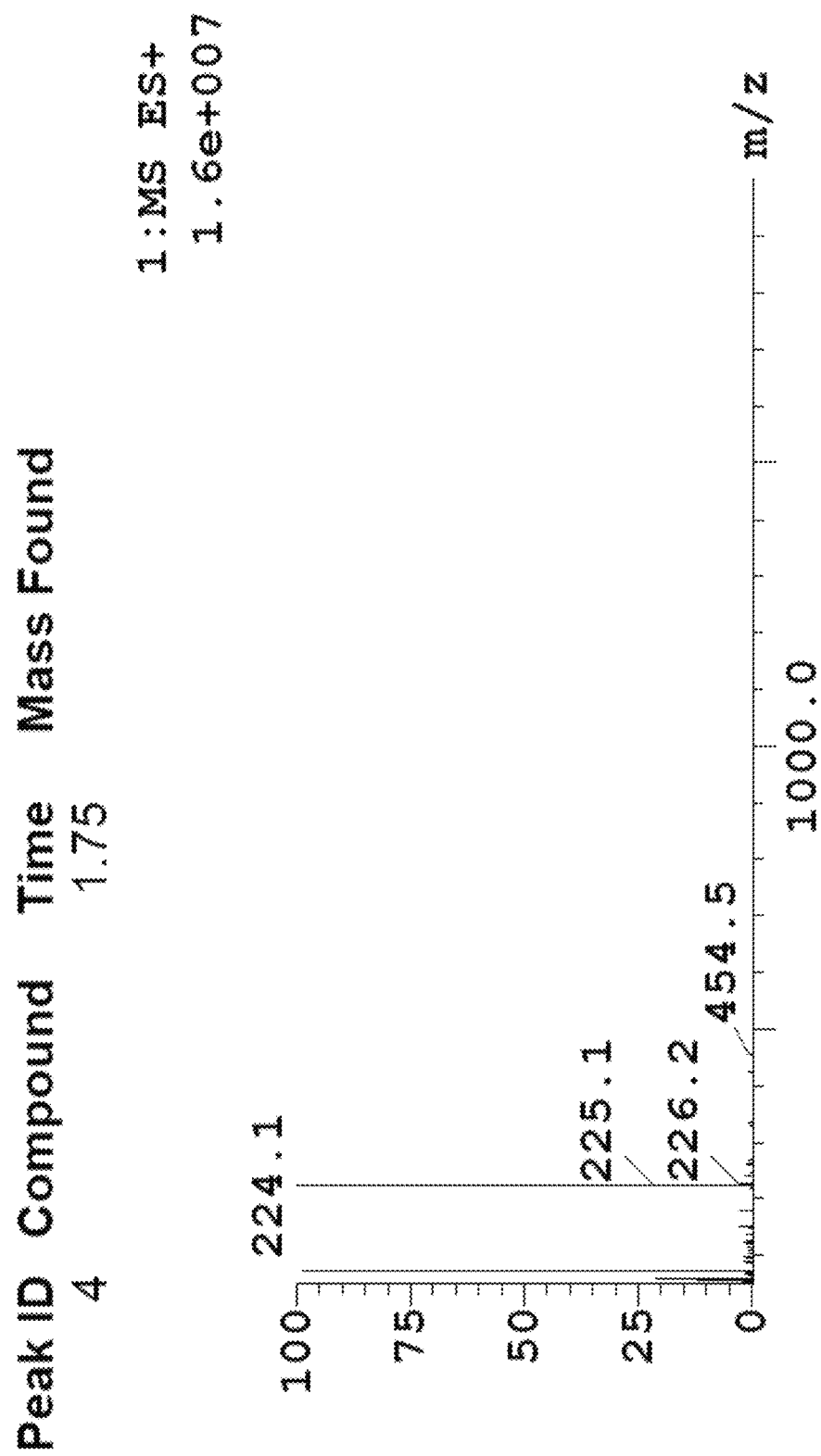

NMR and mass spectrometry analysis of intermediate 3a 4-(2-(dimethylamino)ethoxy)-3-methoxybenzaldehyde is provided in FIGS. 4A to 4C:

$^1$H NMR (400 MHz, Chloroform-d) δ9.82 (s, 1H), 7.41 (dd, J=8.2, 1.9 Hz, 1H), 7.37 (d, J=1.9 Hz, 1H), 6.96 (d, J=8.2 Hz, 1H), 4.17 (t, J=6.1 Hz, 2H), 3.89 (s, 3H), 2.79 (t, J=6.1 Hz, 2H), 2.32 (s, 6H). (FIG. 4A)

$^{13}$C NMR (101 MHz, CDCl$_3$) δ191.2, 154.0, 150.0, 130.3, 127.0, 111.7, 109.3, 67.4, 58.0, 56.2, 46.3. (FIG. 4B) ESI-MS [M+H]: Calculated: 224.1; Observed: 224.1 (FIG. 4C)

To make intermediate 3b 1-(4-(2-(dimethylamino) ethoxy)-3-methoxyphenyl)ethan-1-one, Acetovanillone (1.66 g, 10 mmol), 2-chloro-dimethylethylamine HCl (2.16 g, 15 mmol), potassium iodide (332 mg, 2 mmol) and potassium carbonate (4.14 g, 30 mmol) were suspended in DMF and heated at 70° C. for 16 h. Next, the reaction was diluted with water and ethyl acetate. The organic layer was separated and washed with brine and dried with magnesium sulfate. Concentrating in vacuo resulted in 450 g (19%) of a yellow oil.

Figure 5A:
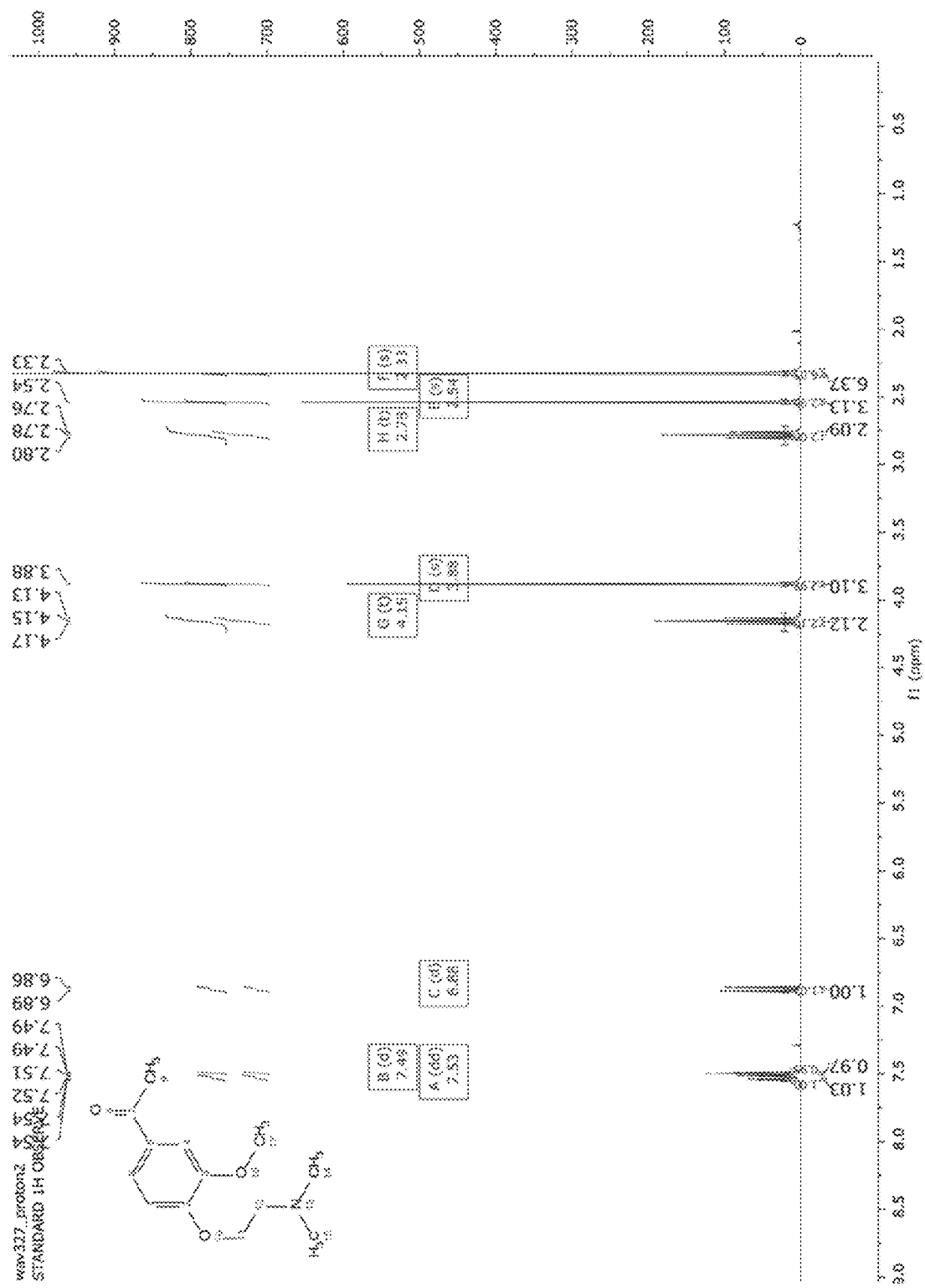
Figure 5B:
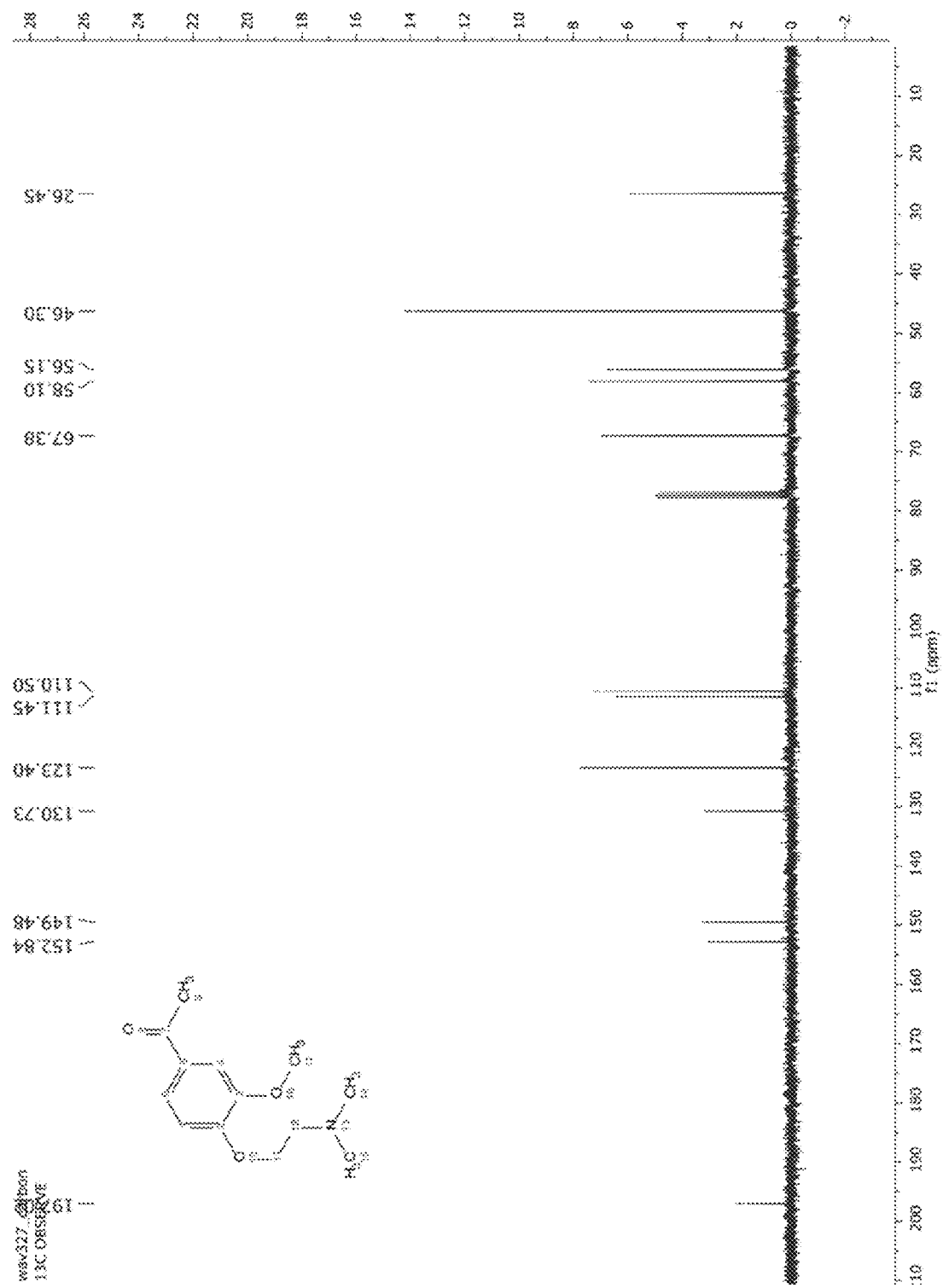

NMR and mass spectrometry analysis of intermediate 3b 1-(4-(2-(dimethylamino)ethoxy)-3-methoxyphenyl)ethan-1-one is provided in FIGS. 5A to 5C:

$^1$H NMR (300 MHz, Chloroform-d) δ7.53 (dd, J=8.3, 2.0 Hz, 1H), 7.49 (d, J=2.0 Hz, 1H), 6.88 (d, J=8.3 Hz, 1H), 4.15 (t, J=6.2 Hz, 2H), 3.88 (s, 3H), 2.78 (t, J=6.2 Hz, 2H), 2.54 (s, 3H), 2.33 (s, 6H). (FIG. 5A)

$^{13}$C NMR (75 MHz, CDCl$_3$) δ197.0, 152.8, 149.5, 130.7, 123.4, 111. 5, 110.5, 67.4, 58.1, 56.2, 46.3, 26.5. (FIG. 5B)

ESI-MS [M+H]: Calculated: 238.1; Observed: 238.2 (FIG. 5C)

To make intermediate 4a 4-(2-(dimethylamino)ethoxy)-5-methoxy-2-nitrobenzaldehyde, compound 3a (1.3 g, 5.8 mmol) was dissolved in TFA (10 mL) and added dropwise to a solution of potassium nitrate (707 mg, 7.0 mmol) in TFA (10 mL) that was cooled on ice. The resulting solution was stirred for 16 h and then concentrated in vacuo. The crude was diluted with water and basified with sat. aq. sodium bicarbonate. The aqueous solution was extracted twice with ethyl acetate and the combined organic fractions were washed with brine and dried with magnesium sulfate. Concentrating in vacuo resulted in 1.1 g (74%) of a yellow solid.

Figure 6A:
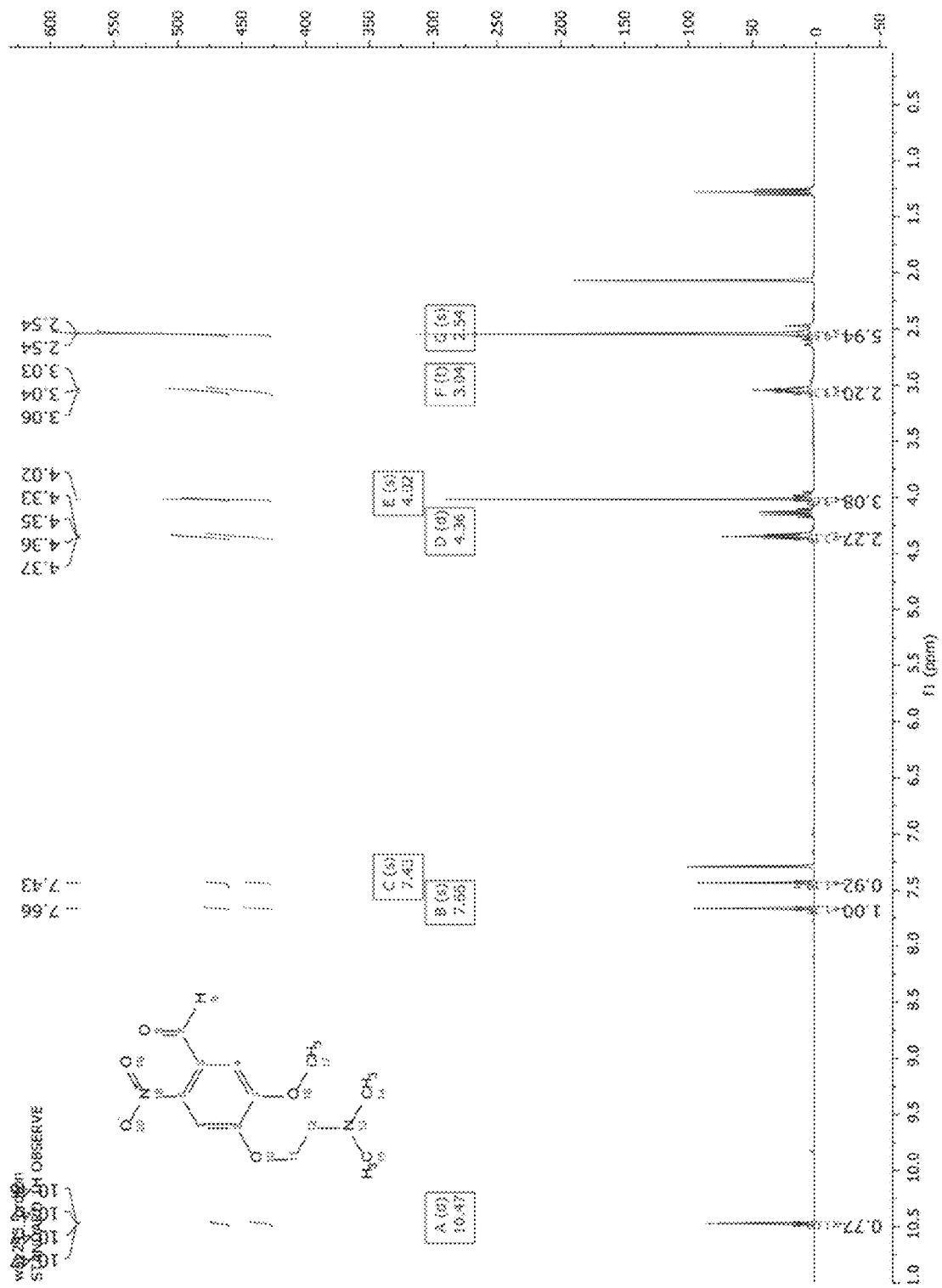
FIGS. 6A-6C provide nuclear magnetic resonance and mass spectrometry data of intermediate 4a, generated in accordance with various embodiments of the invention.
Figure 6B:
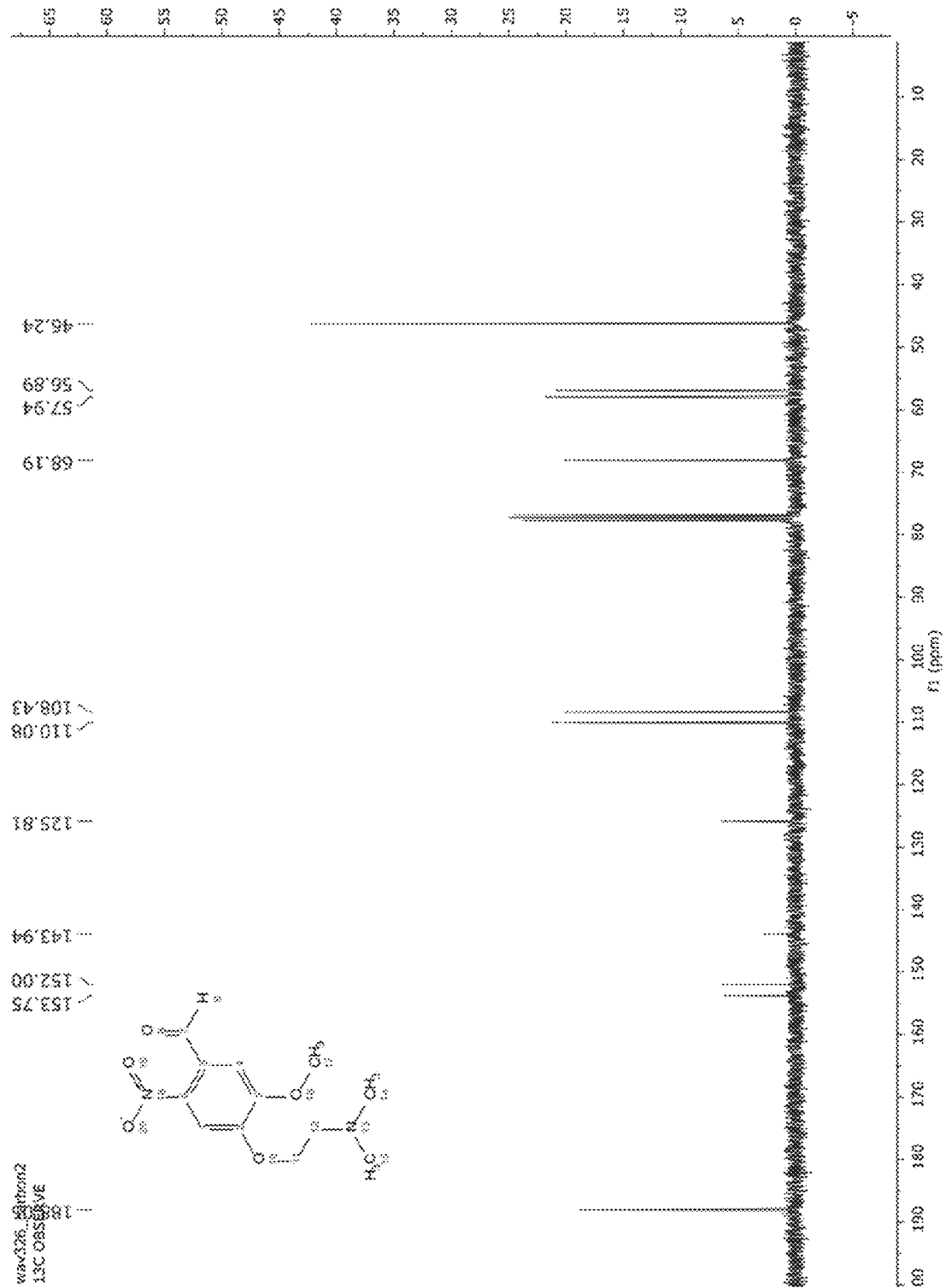
Figure 6C:
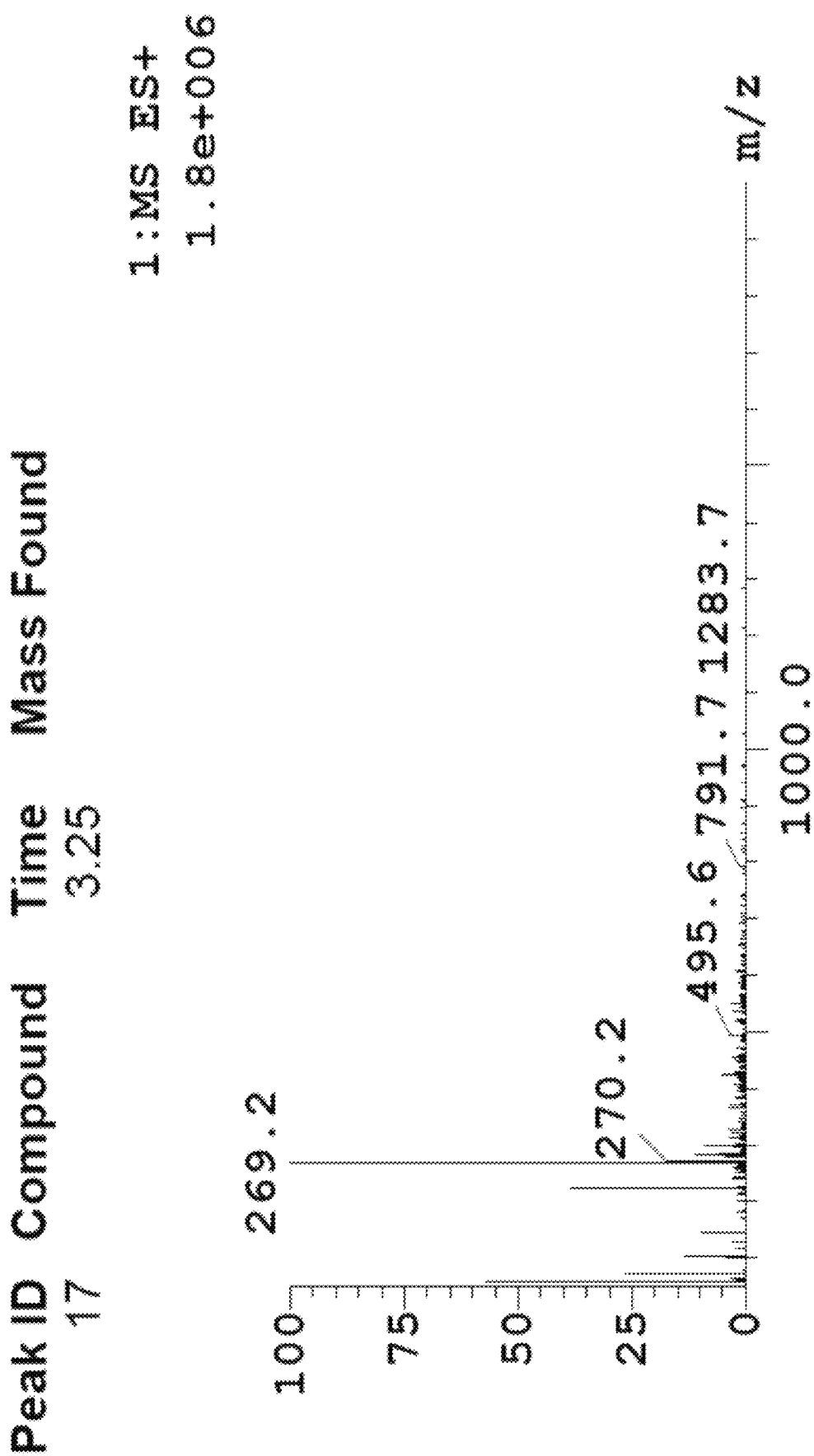

NMR and mass spectrometry analysis of intermediate 4a 4-(2-(dimethylamino)ethoxy)-5-methoxy-2-nitrobenzaldehyde is provided in FIGS. 6A to 6C:

$^1$H NMR (300 MHz, Chloroform-d) δ10.47 (s, 1H), 7.66 (s, 1H), 7.43 (s, 1H), 4.36 (d, J=5.5 Hz, 3H), 4.02 (s, 3H), 3.04 (t, J=5.5 Hz, 3H), 2.54 (s, 6H). (FIG. 6A)

$^{13}$C NMR (75 MHz, CDCl$_3$) δ188.1, 153.8, 152.0, 143.9, 125.8, 110.1, 108.4, 68.2, 57.9, 56.9, 46.2. (FIG. 6B)

ESI-MS [M+H]: Calculated: 269.1; Observed: 269.2 (FIG. 6C)

To make intermediate 4b 1-(4-(2-(dimethylamino) ethoxy)-5-methoxy-2-nitrophenyl)ethan-1-one, compound 3b (270 mg, 1.1 mmol) was dissolved in TFA (1 mL) and added dropwise to a solution of potassium nitrate (139 mg, 1.4 mmol) in TFA (4 mL) that was cooled on ice. The resulting solution was stirred for 16 h and then concentrated in vacuo. The crude was diluted with water and basified with sat. aq. sodium bicarbonate. The aqueous solution was extracted twice with ethyl acetate and the combined organic fractions were washed with brine and dried with magnesium sulfate. Concentrating in vacuo resulted in 300 mg (93%) of a beige solid.

Figure 7A:
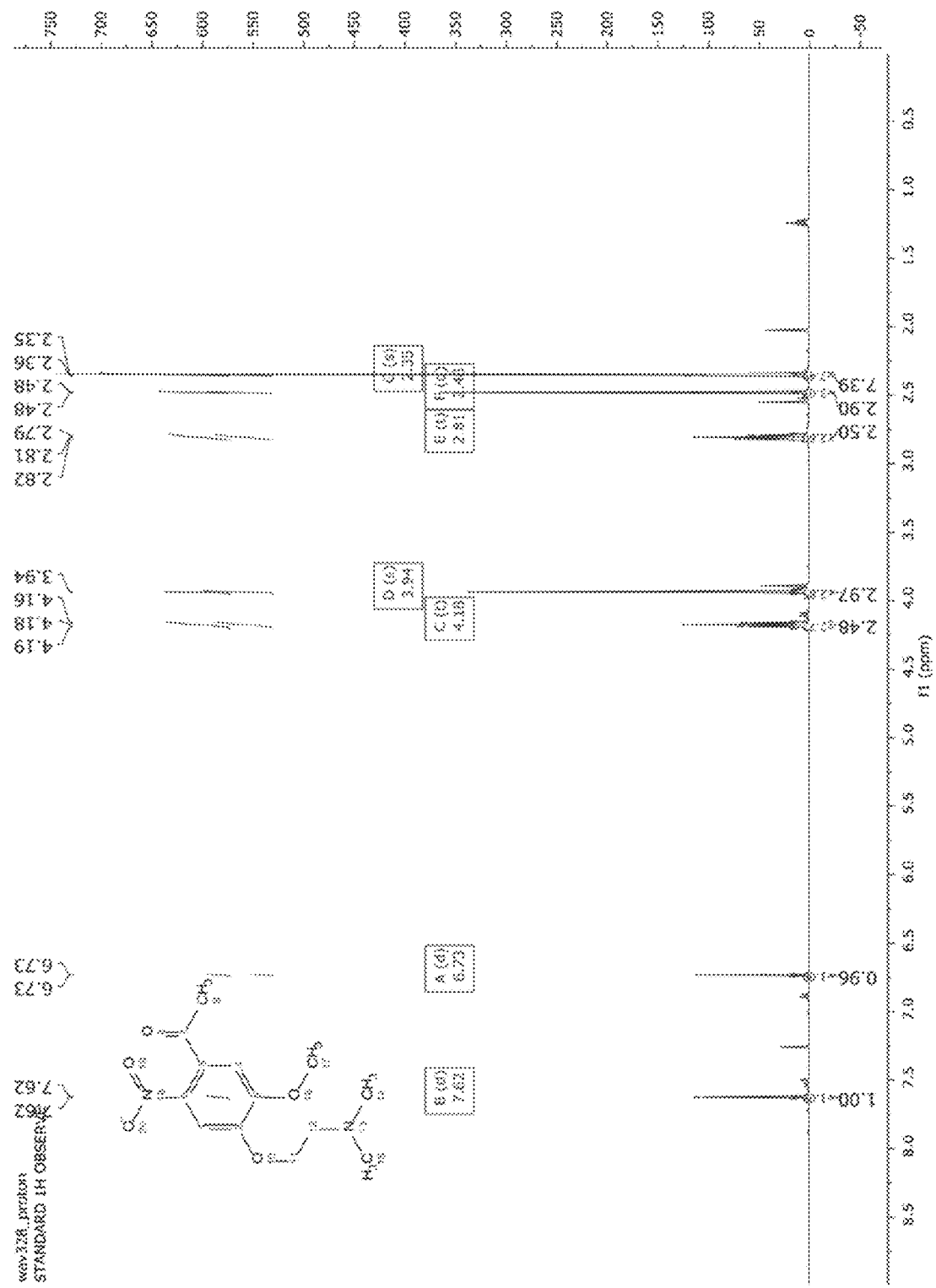
Figure 7C:
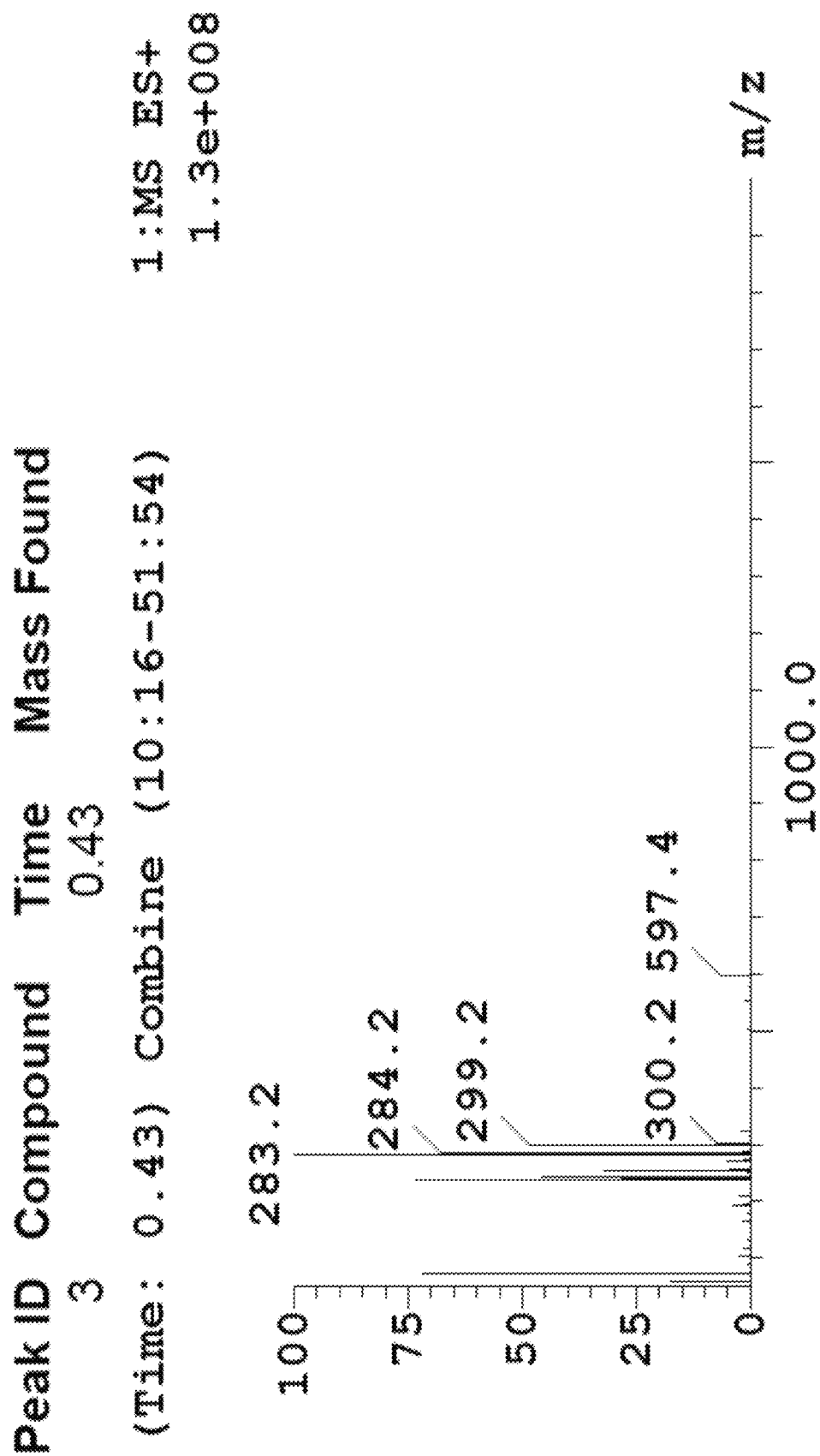

NMR and mass spectrometry analysis of intermediate 4b 1-(4-(2-(dimethylamino)ethoxy)-5-methoxy-2-nitrophenyl) ethan-1-one is provided in FIGS. 7A to 7C:

$^1$H NMR (300 MHz, Chloroform-d) δ10.47 (s, 1H), 7.66 (s, 1H), 7.43 (s, 1H), 4.36 (d, J=5.5 Hz, 3H), 4.02 (s, 3H), 3.04 (t, J=5.5 Hz, 3H), 2.54 (s, 6H). (FIG. 7A)

$^{13}$C NMR (101 MHz, CDCl$_3$) δ200.4, 154.6, 149.1, 138.5, 133.2, 108.9, 108.3, 67.9, 58.0, 56.8, 46.28, 30.6. (FIG. 7B)

ESI-MS [M+H]: Calculated: 283.1; Observed: 283.2 (FIG. 7C)

To make intermediate 5a (4-(2-(dimethylamino)ethoxy)-5-methoxy-2-nitrophenyl)methanol, compound 4a (1.0 g, 3.7 mmol) was dissolved in methanol (10 mL). Sodium borohydride (284 mg, 7.5 mmol) was added in portions and the resulting solution is stirred for 10 min, when full conversion was observed by TLC. The reaction is concentrated in vacuo and the crude purified with flash chromatography (EtOAc:TEA 95:5) and recrystallized from EtoAc, resulting in 700 mg (70%) of yellow crystals.

Figure 8A:
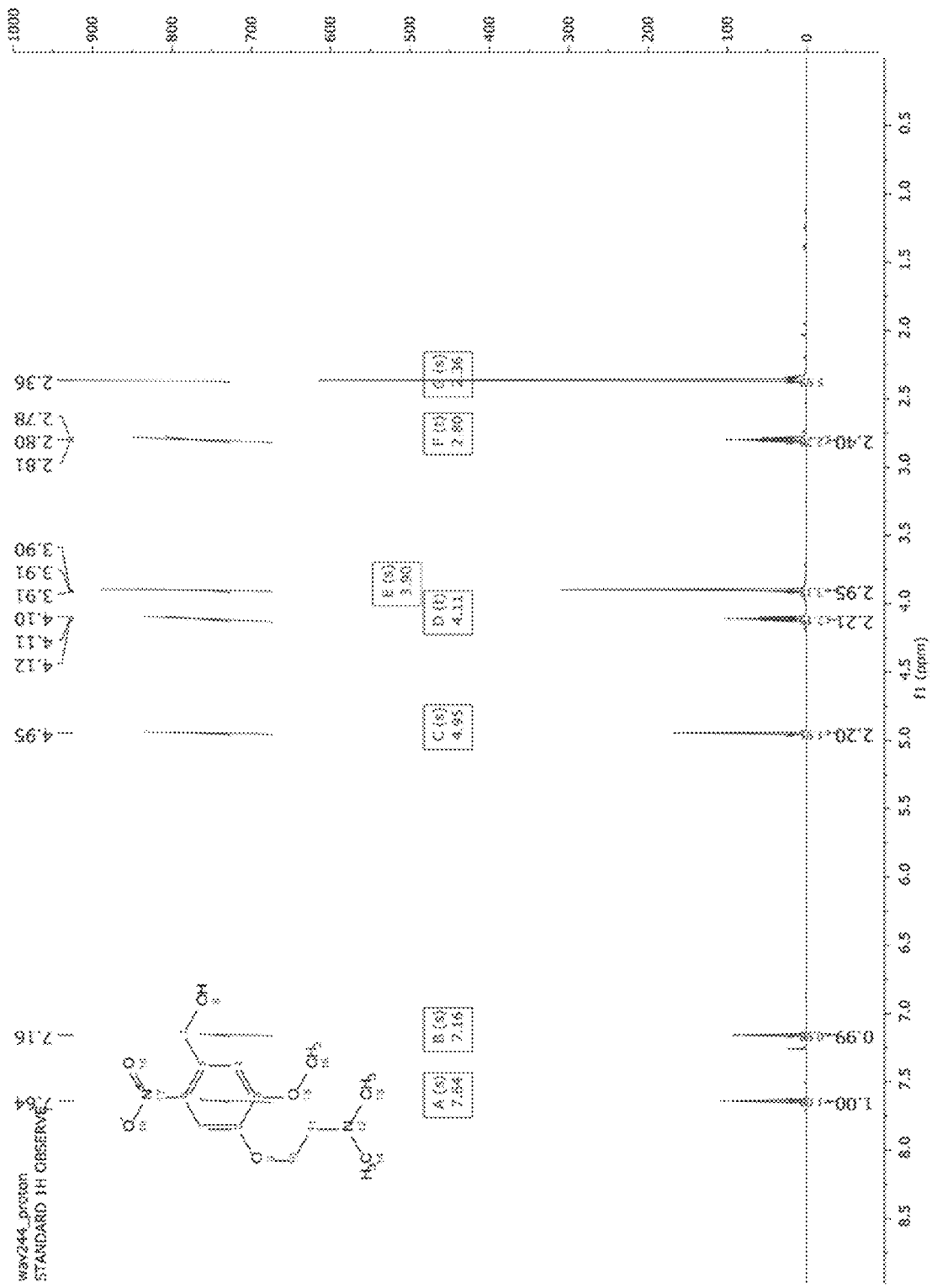
Figure 8B:
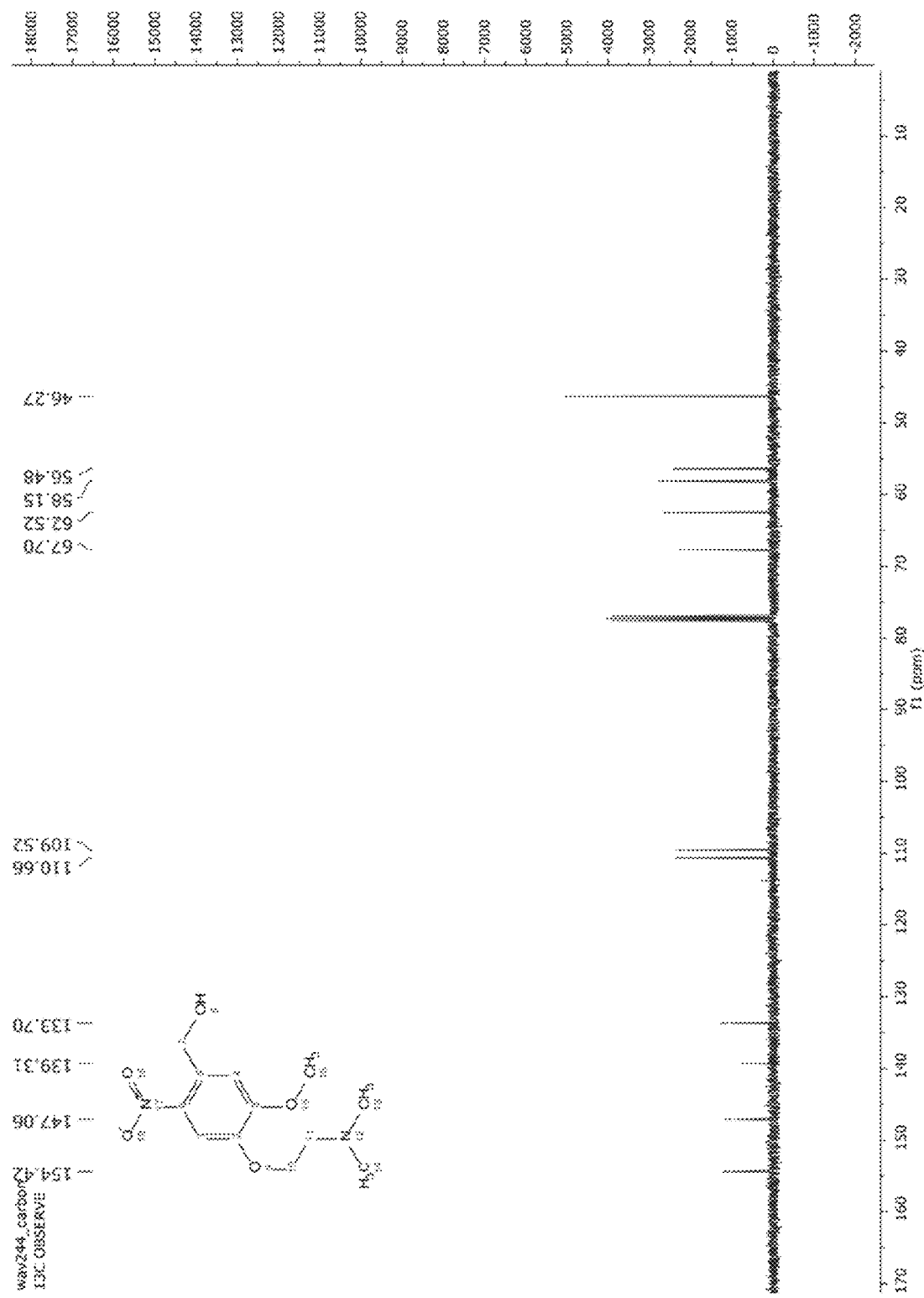

NMR and mass spectrometry analysis of intermediate 5a (4-(2-(dimethylamino)ethoxy)-5-methoxy-2-nitrophenyl) methanol is provided in FIGS. 8A to 8C:

$^1$H NMR (400 MHz, Chloroform-d) δ7.64 (s, 1H), 7.16 (s, 1H), 4.95 (s, 2H), 4.11 (t, J=5.6 Hz, 2H), 3.90 (s, 3H), 2.80 (t, J=5.6 Hz, 2H), 2.36 (s, 6H). (FIG. 8A)

$^{13}$C NMR (101 MHz, CDCl$_3$) δ154.4, 147.1, 139.3, 133.7, 110.7, 109.5, 67.7, 62.5, 58.1, 56.5, 46.3. (FIG. 8B)

ESI-MS [M+H]: Calculated: 271.1; Observed: 271.1 (FIG. 8C)

To make intermediate 5b 1-(4-(2-(dimethylamino) ethoxy)-5-methoxy-2-nitrophenyl)ethan-1-ol, compound 4b (300 mg, 1.1 mmol) was dissolved in methanol (5 mL). Sodium borohydride (81 mg, 2.1 mmol) was added in portions and the resulting solution is stirred for 1 h, when full conversion was observed by TLC. The reaction was concentrated in vacuo and the crude purified with flash chromatography (EtOAc:TEA 95:5) and recrystallized from EtOAc resulting in 130 mg (41%) of yellow crystals.

Figure 9A:
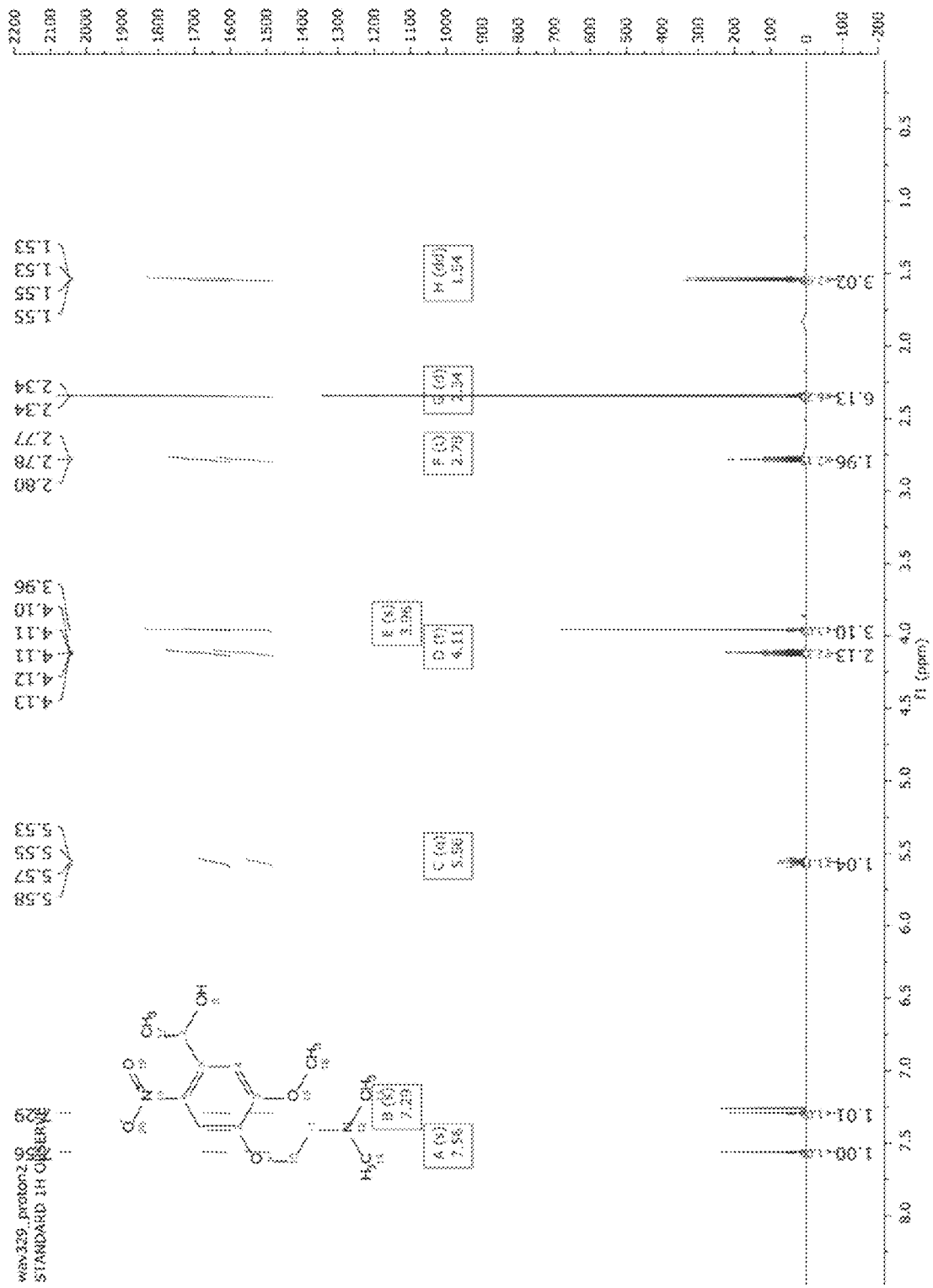
Figure 9B:
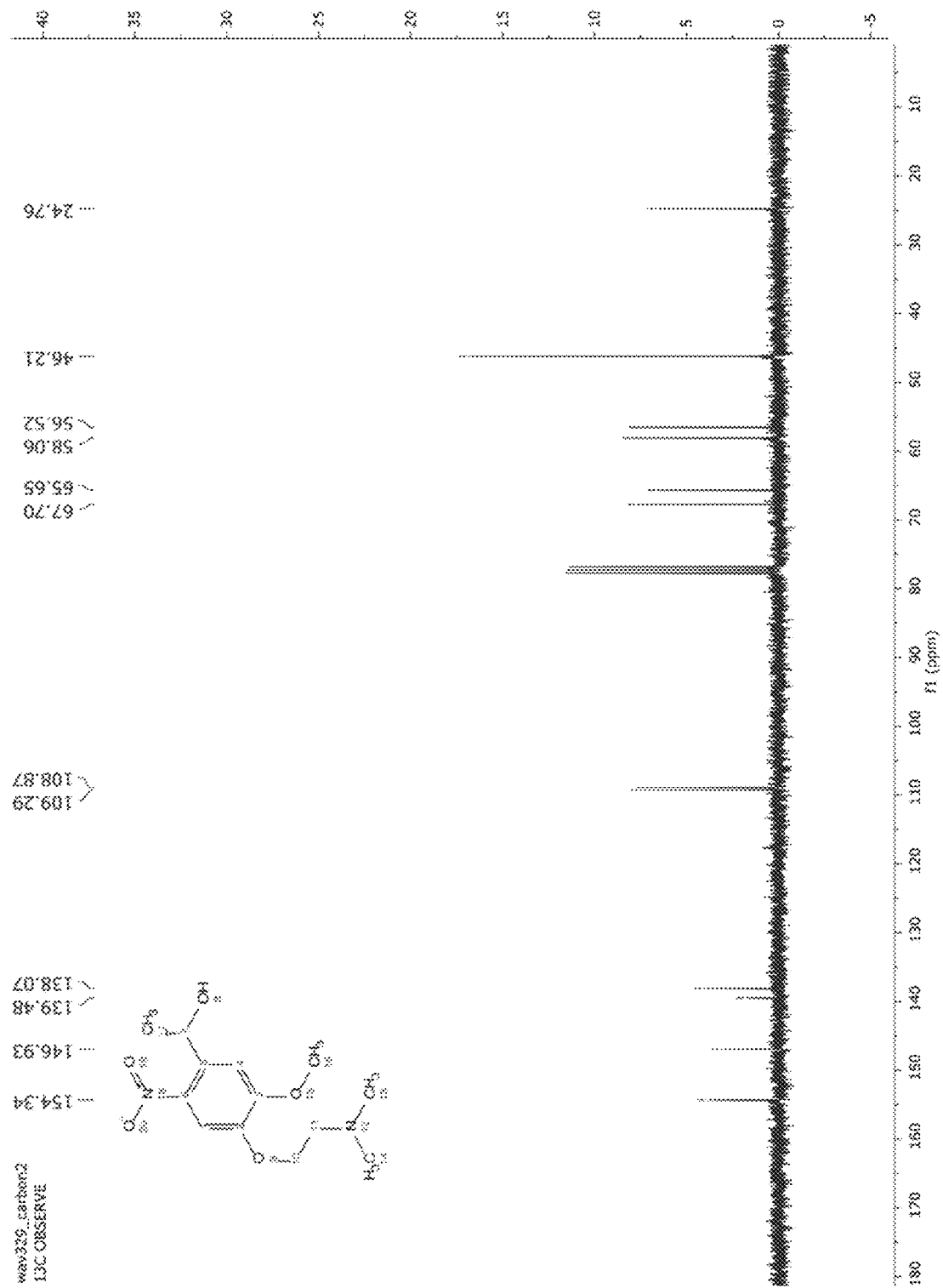

NMR and mass spectrometry analysis of intermediate 5b 1-(4-(2-(dimethylamino)ethoxy)-5-methoxy-2-nitrophenyl) ethan-1-ol is provided in FIGS. 9A to 9C:

$^1$H NMR (400 MHz, Chloroform-d) δ7.56 (s, 1H), 7.29 (s, 1H), 5.56 (q, J=6.3 Hz, 1H), 4.11 (t, J=5.9 Hz, 2H), 3.96 (s, 3H), 2.78 (t, J=5.8 Hz, 2H), 2.34 (s, 6H), 1.54 (d, J=6.3, 3H). (FIG. 9A)

¹³C NMR (75 MHz, CDCl₃) δ154.3, 146.9, 139.5, 138.17, 109.3, 108.9, 67.7, 65.7, 58.1, 56.5, 46.2, 24.8. (FIG. 9B)

ESI-MS [M+H]: Calculated: 285.2; Observed: 285.2 (FIG. 9C)

To make PCA 1 4-(2-(dimethylamino)ethoxy)-5-methoxy-2-nitrobenzyl 2-chloro-1H-imidazole-1-carboxylate, carbonyldichloroimidazole (CDCl) was freshly prepared by dissolving 2-chloroimidazole (102 mg, 1.0 mmol) in THF (1.5 mL) and triphosgene (25 mg, 0.08 mmol) dissolved in THF (1.0 mL) was added to this. The resulting mixture was stirred for 30 min at room temperature and then filtered. The filtrate was concentrated in vacuo and dried under high vacuum for 5 min resulting in a white powder (¹H NMR (300 MHz, DMSO-d₆) δ7.70 (d, J=1.9 Hz, 2H), 7.14 (d, J=1.9 Hz, 2H)), which was immediately used without any further purification. The white powder was dissolved in THF (1.0 mL) and to this was added a solution of compound 4a (8 mg, 0.03 mmol) dissolved in THF (1.0 mL) and the resulting mixture was stirred for 5 min at room temperature. Next, DIPEA (35 µL, 0.20 mmol) was added and the reaction was stirred for an additional 5 min before concentrating in vacuo. The obtained yellow solid was immediately dissolved in DMSO (30 µL) resulting in a ~1 M solution and stored at −80° C.

Figure 10A:
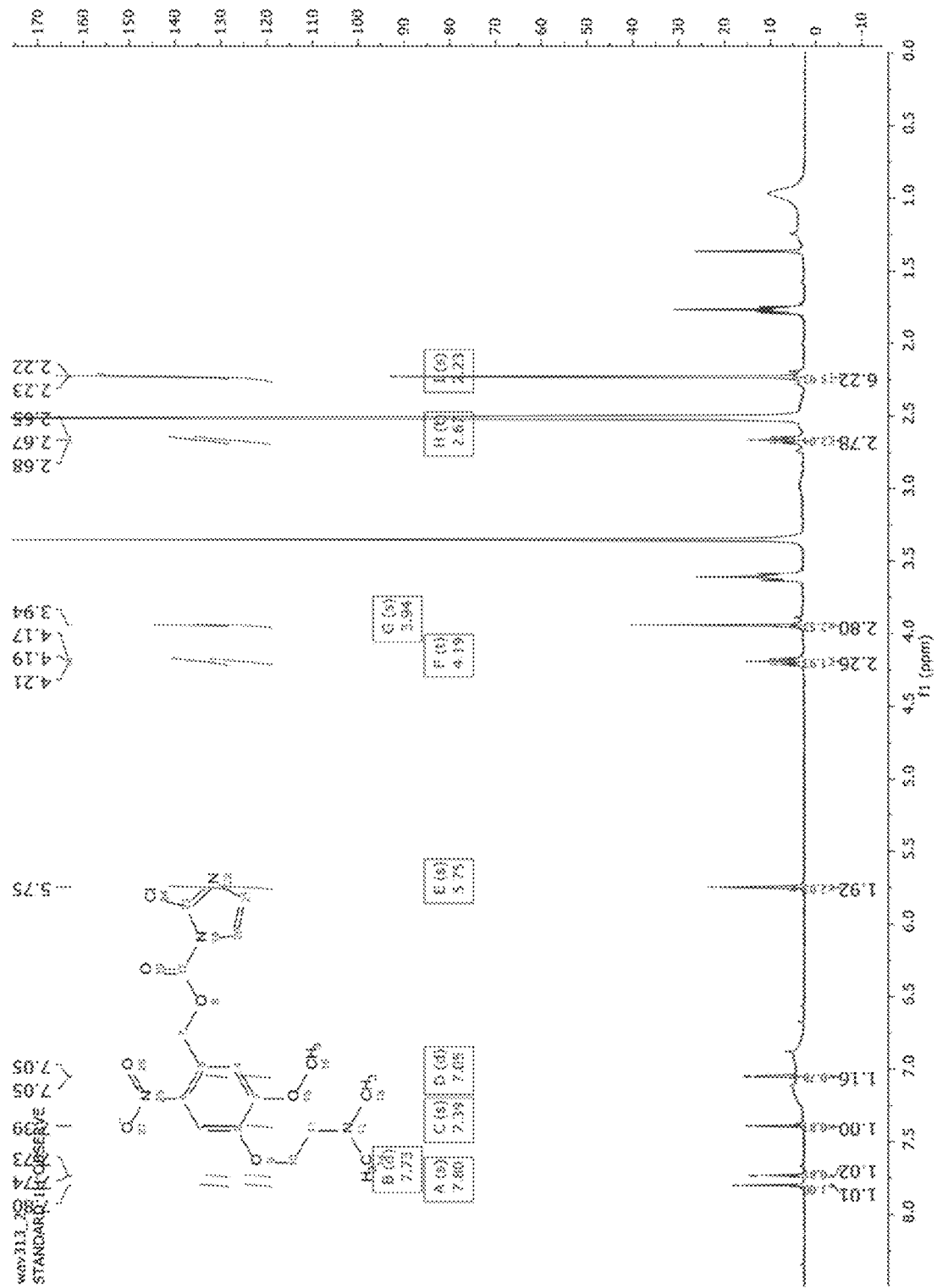
FIGS. 10A & 10B provide nuclear magnetic resonance and mass spectrometry data of photocloaking agent 1, generated in accordance with various embodiments of the invention.
Figure 10B:
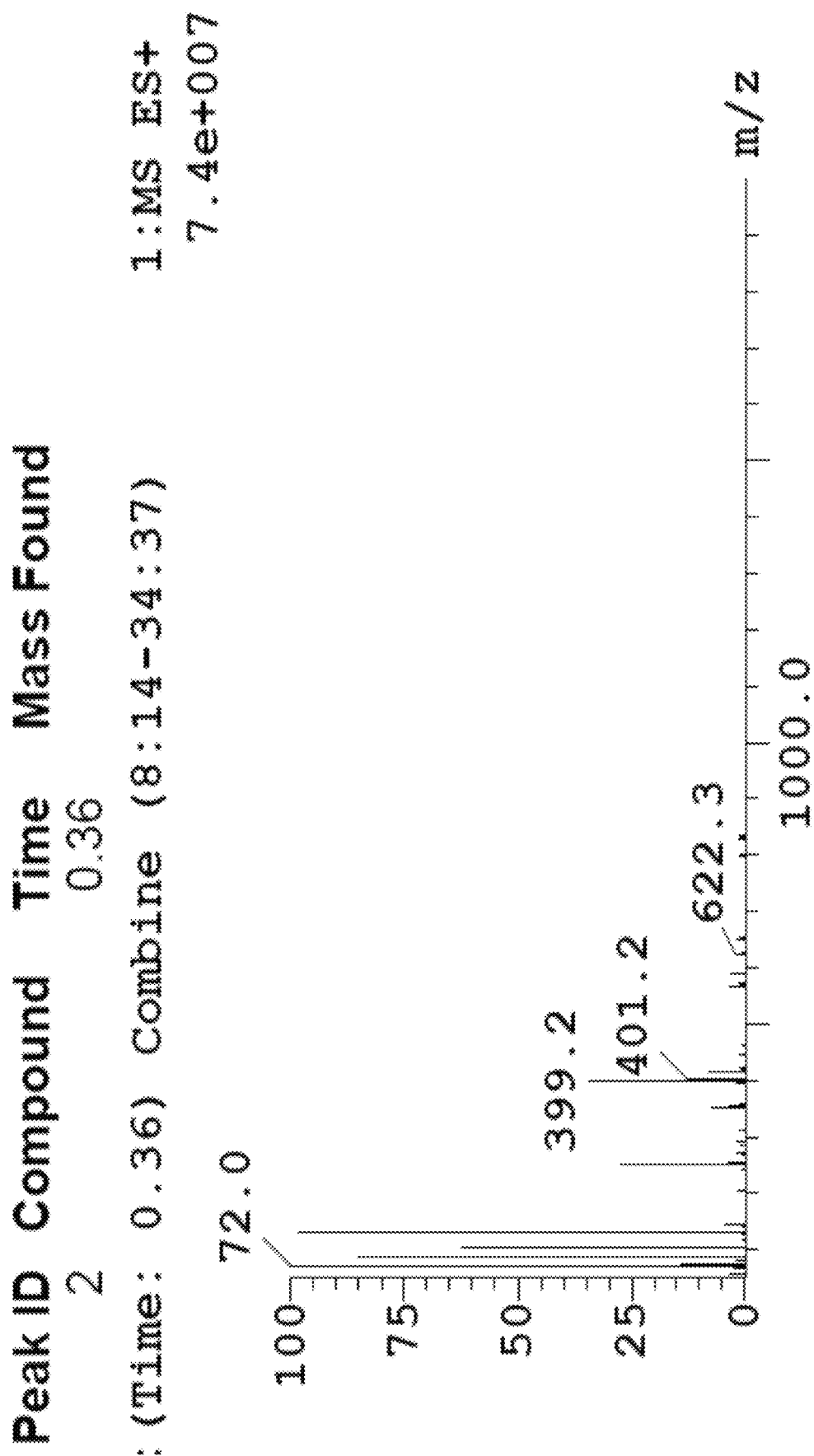

NMR and mass spectrometry analysis of PCA 1 4-(2-(dimethylamino)ethoxy)-5-methoxy-2-nitrobenzyl 2-chloro-1H-imidazole-1-carboxylate is provided in FIGS. 10A and 10B:

¹H NMR (300 MHz, DMSO-d₆) δ7.80 (s, 1H), 7.73 (d, J=1.9 Hz, 1H), 7.39 (s, 1H), 7.05 (d, J=1.9 Hz, 1H), 5.75 (s, 2H), 4.19 (t, J=5.7 Hz, 2H), 3.94 (s, 3H), 2.67 (t, J=5.6 Hz, 2H), 2.23 (s, 6H). (FIG. 10A)

ESI-MS [M+H]: Calculated: 399.1; Observed: 399.2 (FIG. 10B)

To make PCA 2 1-(4-(2-(dimethylamino)ethoxy)-5-methoxy-2-nitrophenyl)ethyl 2-chloro-1H-imidazole-1-carboxylate, carbonyldichloroimidazole (CDCl) was freshly prepared by dissolving 2-chloroimidazole (102 mg, 1.0 mmol) in THF (1.5 mL) and triphosgene (25 mg, 0.08 mmol) dissolved in THF (1.0 mL) was added to this. The resulting mixture is stirred for 30 min at room temperature and then filtered. The filtrate was concentrated in vacuo and dried under high vacuum for 5 min resulting in a white powder (¹H NMR (300 MHz, DMSO-d₆) δ7.70 (d, J=1.9 Hz, 2H), 7.14 (d, J=1.9 Hz, 2H)), which was immediately used without any further purification. The white powder was dissolved in THF (1.0 mL) and to this was added a solution of compound 4b (8 mg, 0.03 mmol) dissolved in THF (1.0 mL) and the resulting mixture was stirred for 5 min at room temperature. Next, DIPEA (35 µL, 0.20 mmol) was added and the reaction was stirred for an additional 5 min before concentrating in vacuo. The obtained yellow solid was immediately dissolved in DMSO (30 µL) resulting in a ~1 M solution and stored at −80° C.

Figure 11A:
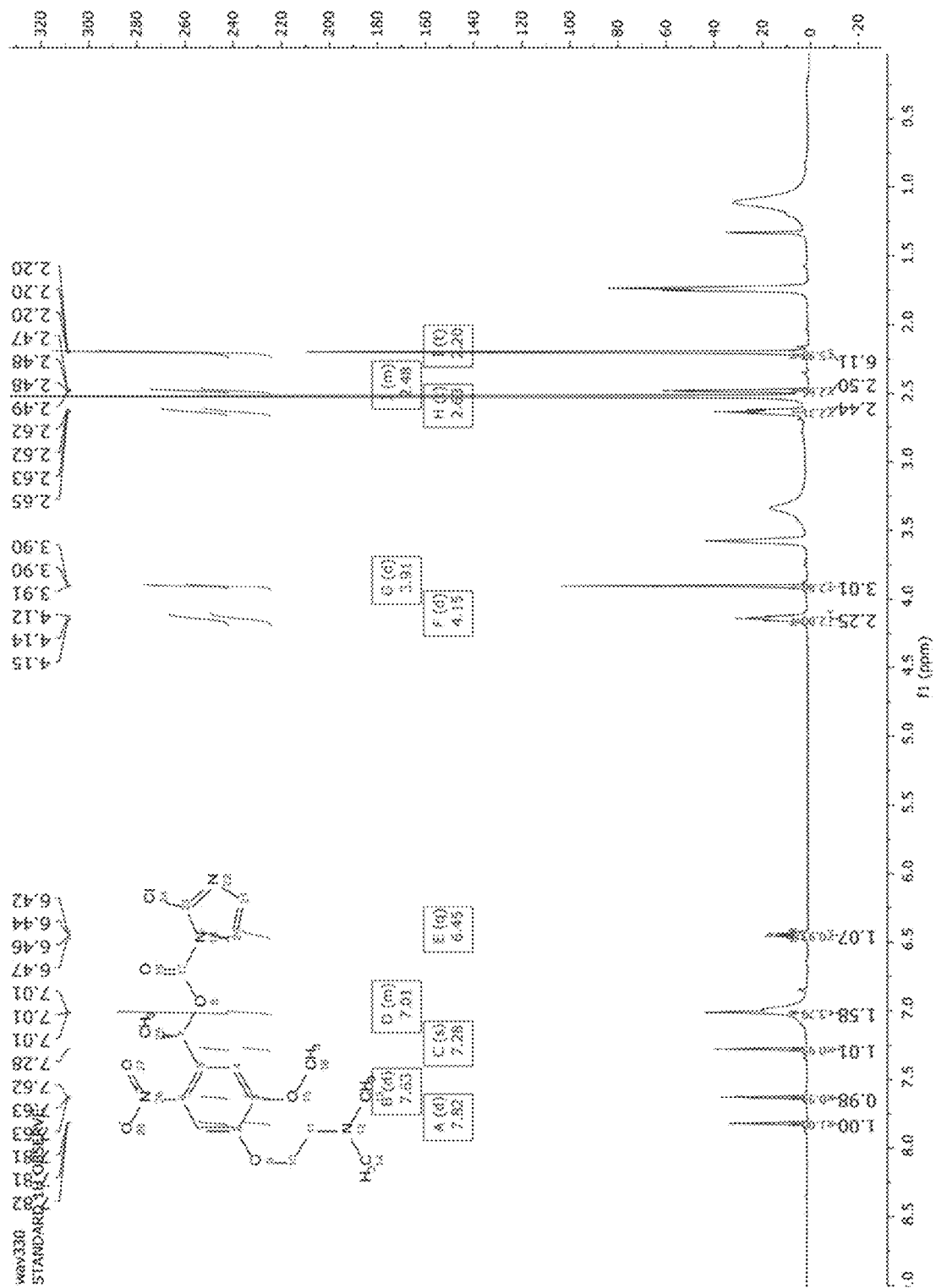

NMR and mass spectrometry analysis of PCA 2 1-(4-(2-(dimethylamino)ethoxy)-5-methoxy-2-nitrophenyl)ethyl 2-chloro-1H-imidazole-1-carboxylate is provided in FIGS. 11A and 11B:

¹H NMR ((400 MHz, DMSO-d₆) δ7.82 (d, J=1.7 Hz, 1H), 7.63 (d, J=2.0 Hz, 1H), 7.28 (s, 1H), 7.02 (s, 1H), 6.45 (q, J=6.4 Hz, 1H), 4.15 (t, J=6.3 Hz, 2H), 3.91 (s, 3H), 2.63 (t, J=5.7 Hz, 2H), 2.49 (s, 3H), 2.20 s, 6H). (FIG. 11A)

ESI-MS [M+H]: Calculated: 413.1; Observed: 413.3 (FIG. 11B)

Leaving Group Optimization

Figure 12:
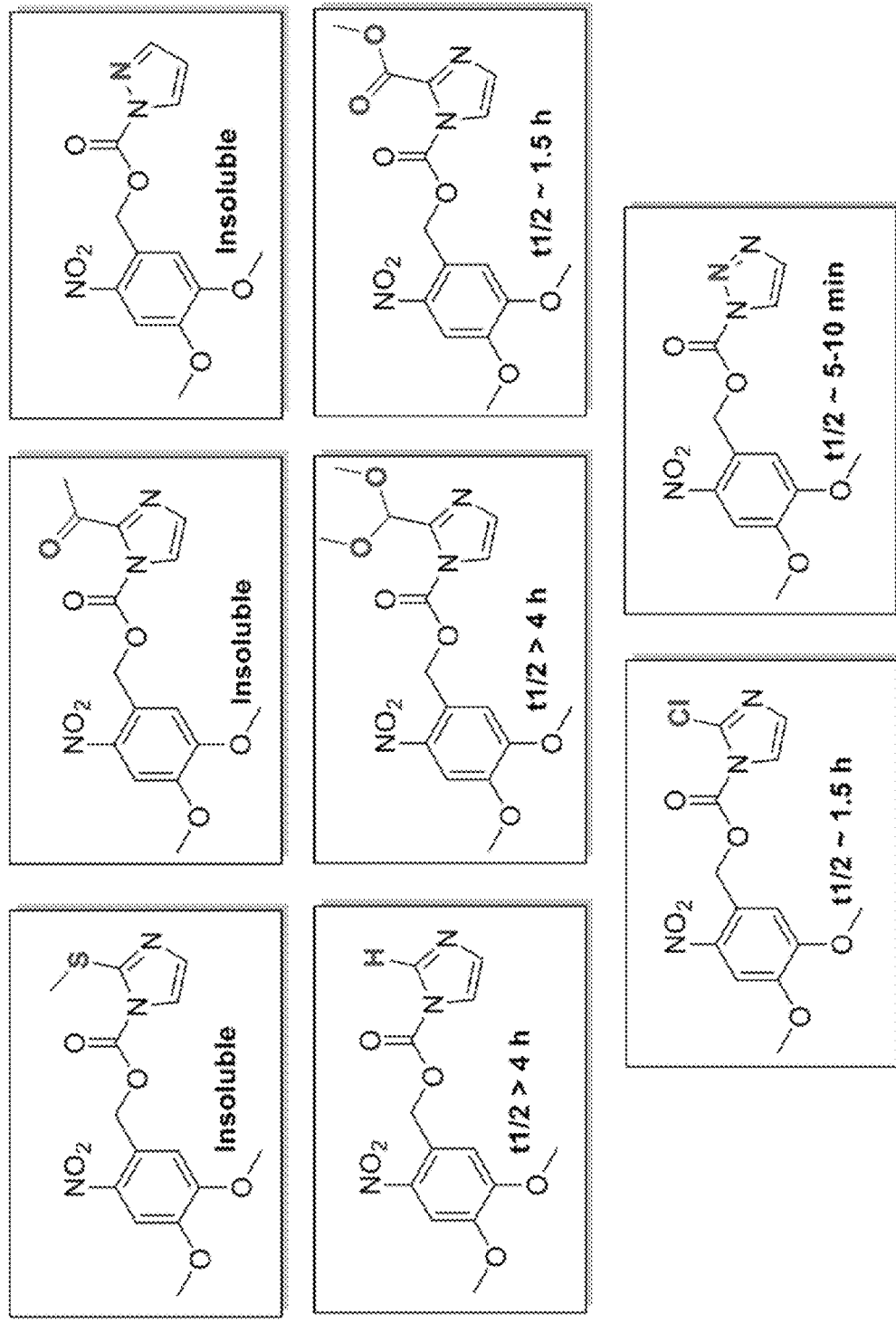

Various leaving groups were tested for their ability to react with RNA in solution. The leaving groups tested are depicted in FIG. 12. Half-lives of compounds with various leaving groups were determined by NMR spectroscopy by dissolving the compounds in a 1:1 mixture of DMSO$_{d6}$ and 50 mM phosphate buffer prepared with deuterium oxide. Compound hydrolysis was observed overtime.

To create compounds having various leaving groups, 4,5-dimethoxy-2-nitrobenzyl chloroformate (0.36 mmol, 100 mg) is provided as an example, which was dissolved in DCM (2 mL) and to this was added a solution of 5-membered heterocycle (0.36 mmol or 0.72 mmol, depending on pKa) in DCM (2 mL). The resulting reaction was stirred at room temperature until full conversion. If the desired product precipitated from the reaction it was obtained by filtration. If not, the reaction was filtered and the filtrate concentrated to yield the desired product.

NMR results are as follows:

4, 5-dimethoxy-2-nitrobenzyl 2-(methylthio)-1H-imidazole-1-carboxylate ¹H NMR (400 MHz, DMSO-d₆) δ7.73 (s, 1H), 7.59 (s, 1H), 7.37 (s, 1H), 7.02 (s, 1H), 5.69 (s, 2H), 3.91 (s, 3H), 3.87 (s, 3H).

4, 5-dimethoxy-2-nitrobenzyl 2-acetyl-1H-imidazole-1-carboxylate ¹H NMR (300 MHz, DMSO-d₆) δ7.87 (d, J=1.4 Hz, 1H), 7.76 (s, 1H), 7.33 (s, 1H), 7.23 (d, J=1.5 Hz, 1H), 5.75 (s, 2H), 3.95 (s, 3H), 3.91 (s, 3H), 2.59 (s, 3H).

4, 5-dimethoxy-2-nitrobenzyl 1H-pyrazole-1-carboxylate ¹H NMR (400 MHz, DMSO-d₆) δ8.37 (dd, J=2.8, 0.7 Hz, 1H), 7.87 (dd, J=1.6, 0.7 Hz, 1H), 7.74 (s, 1H), 7.38 (s, 1H), 6.58 (dd, J=2.8, 1.6 Hz, 1H), 5.72 (s, 2H), 3.90 (s, 3H), 3.88 (s, 3H).

4,5-dimethoxy-2-nitrobenzyl 1H-imidazole-1-carboxylate ¹H NMR (300 MHz, DMSO-d₆) δ8.83 (s, 1H), 7.83 (s, 1H), 7.77 (s, 1H), 7.38 (s, 1H), 7.34 (s, 1H), 5.78 (s, 2H), 3.95 (s, 3H), 3.91 (s, 3H).

4, 5-dimethoxy-2-nitrobenzyl 2-(dimethoxymethyl)-1H-imidazole-1-carboxylate ¹H NMR (400 MHz, DMSO-d₆) δ7.74 (s, 1H), 7.60 (dd, J=1.7, 0.5 Hz, 1H), 7.35 (s, 1H), 6.99 (dd, J=1.7, 0.4 Hz, 1H), 5.76 (s, 1H), 5.69 (s, 2H), 3.91 (s, 3H), 3.88 (s, 3H), 3.29 (d, J=0.5 Hz, 6H).

1-(4,5-dimethoxy-2-nitrobenzyl) 2-methyl 1H-imidazole-1,2-dicarboxylate ¹H NMR (300 MHz, DMSO-d₆) δ7.80 (d, J=1.1 Hz, 1H), 7.78 (s, 1H), 7.35 (s, 1H), 7.19 (d, J=1.1 Hz, 1H), 5.75 (s, 2H), 3.95 (s, 3H), 3.91 (s, 4H), 3.75 (s, 3H).

4, 5-dimethoxy-2-nitrobenzyl 2-chloro-1H-imidazole-1-carboxylate ¹H NMR (400 MHz, DMSO-d₆) δ7.73 (s, 1H), 7.71 (d, J=1.9 Hz, 1H), 7.37 (s, 1H), 7.02 (dd, J=1.9, 1.1 Hz, 0H), 5.72 (s, 2H), 3.91 (s, 3H), 3.88 (s, 3H).

4, 5-dimethoxy-2-nitrobenzyl 1 H-1, 2, 3-triazole-1-carboxylate ¹H NMR (400 MHz, DMSO-d₆) δ8.76 (dd, J=1.5, 1H), 7.97 (dd, J=1.4, 1H), 7.75 (s, 1H), 7.41 (s, 1H), 5.83 (s, 2H), 3.91 (s, 3H), 3.88 (s, 3H).

RNA Cloaking Example: Cloaking with PCA 1 and Uncloaking via 365 nm Light

To test if prototypical PCA reagent 1 is effective in reacting with RNA, it was incubated for 4 h at 100 mM at room temperature with a 12 nucleotide (nt) RNA strand (10 µM) in water. One µL RNA stock solution in water (1 mM or 100 µM) was dissolved in 8 µL RNAse free biological grade water and heated to 95° C. for 2 min and then cooled to room temperature. To this was added 1 µL 1M PCA stock in dry DMSO and the mixture incubated for 4 h at room temperature unless stated otherwise. The solution becomes slightly cloudy initially and then clears after ~30 min. After reaction, the RNA was precipitated by adding 1 µL of 3 M NaOAc buffer pH=5.2, 1 µL glycogen (10 mg/mL) and 36 µL EtOH and storing at −80° C. for 16 h. The resulting suspension was centrifuged at 14,800 rpm for 60 min and the supernatant was removed. The solids were washed with 10 µL 70% EtOH and centrifuged at 14,800 rpm for 5 min. The supernatant was removed and the RNA was dried in air for 10 min and redissolved in RNAse free biological grade water at the desired concentration. RNA concentration was determined with a Nanodrop One microvolume UV-VIS spectrophotometer. RNA samples were stored at −20° C.

Uncloaking of RNA by photoremoval of the PCA labels was also investigated. To photo-uncloak RNA, samples were diluted in RNAse free biological grade water to the desired concentration and kept in a 500 µL glass vial placed on top of a 365 nm VWR Scientific Transilluminator LM-20E for up to 60 min, depending on the experiment.

Figure 13:
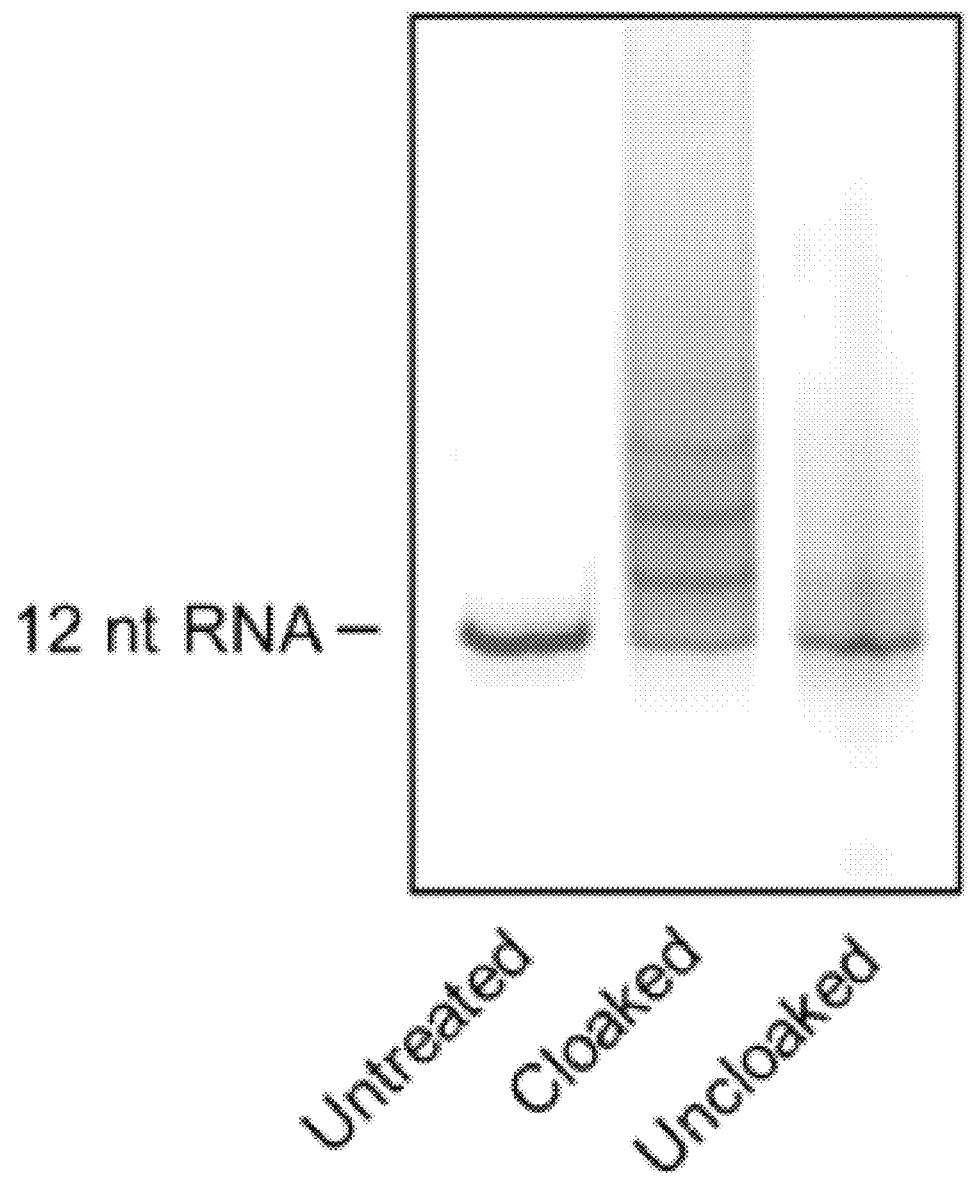
FIG. 13 provides a PAGE electrophoresis image of untreated, cloaked, and uncloaked 12 mer RNA, generated in accordance with various embodiments of the invention.
Figure 14A:
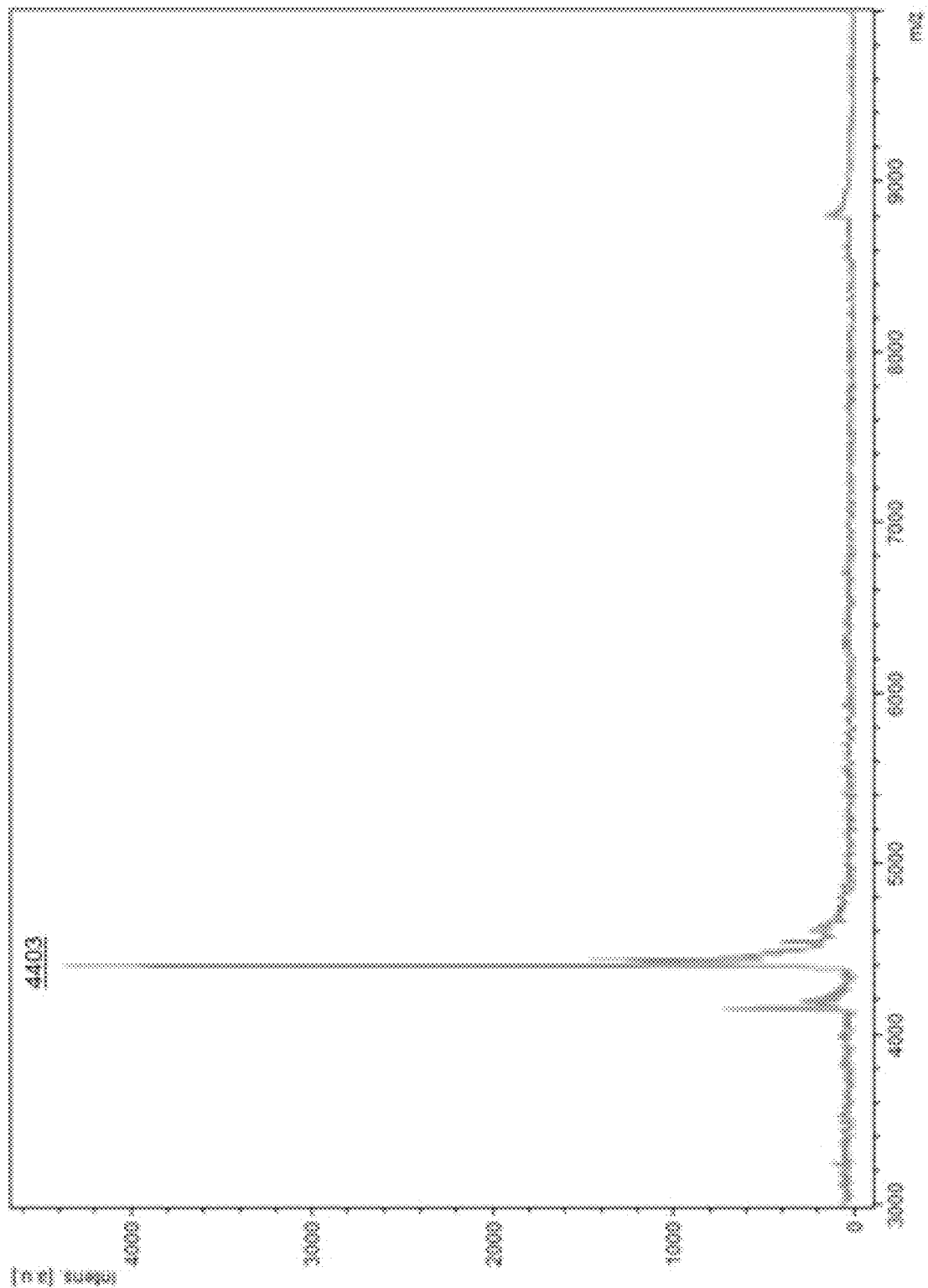
FIG. 14A provides MALDI-TOF spectrum data of untreated 12 mer RNA, generated in accordance with various embodiments of the invention.
Figure 14B:
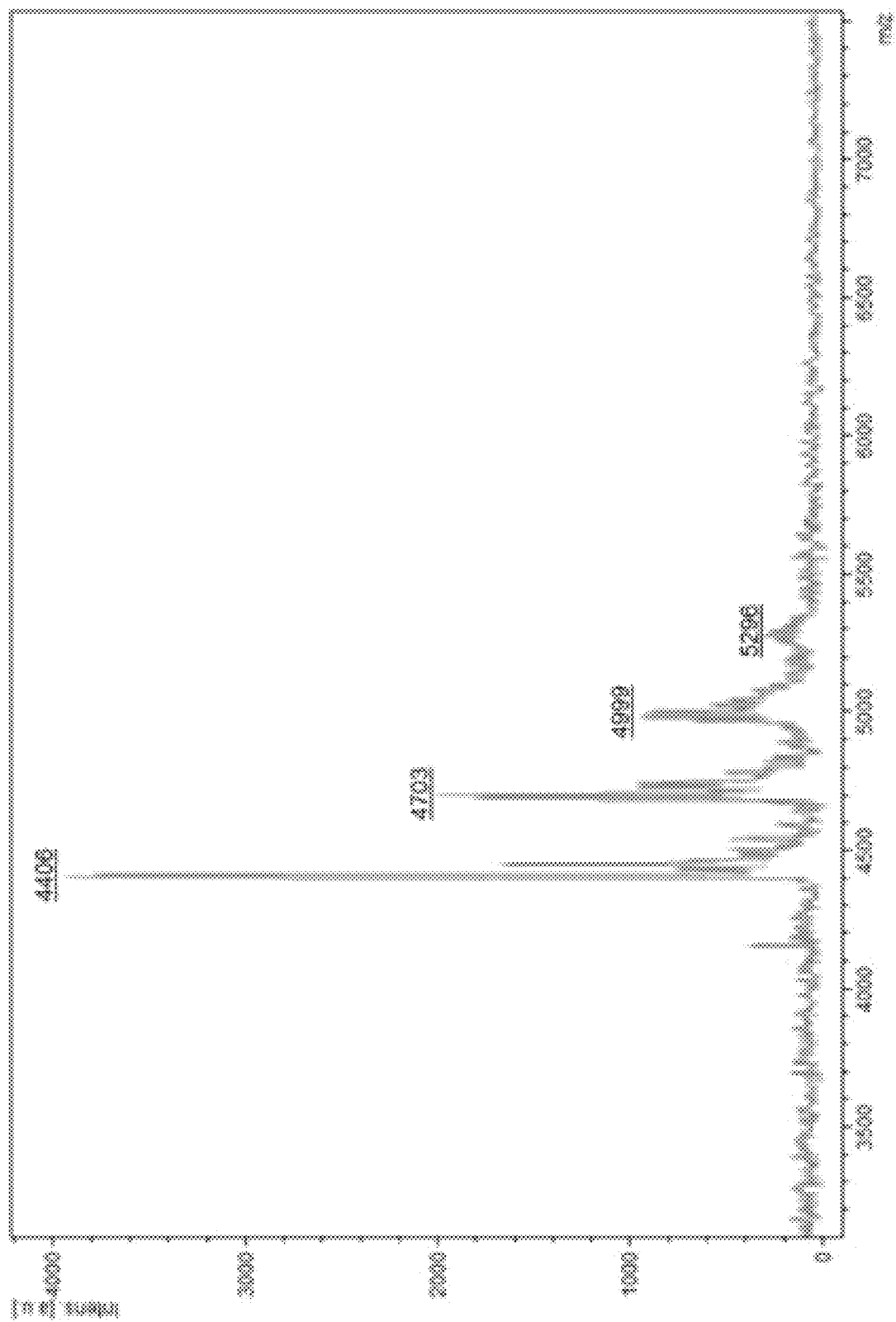
FIG. 14B provides MALDI-TOF spectrum data of cloaked 12 mer RNA, generated in accordance with various embodiments of the invention.
Figure 14C:
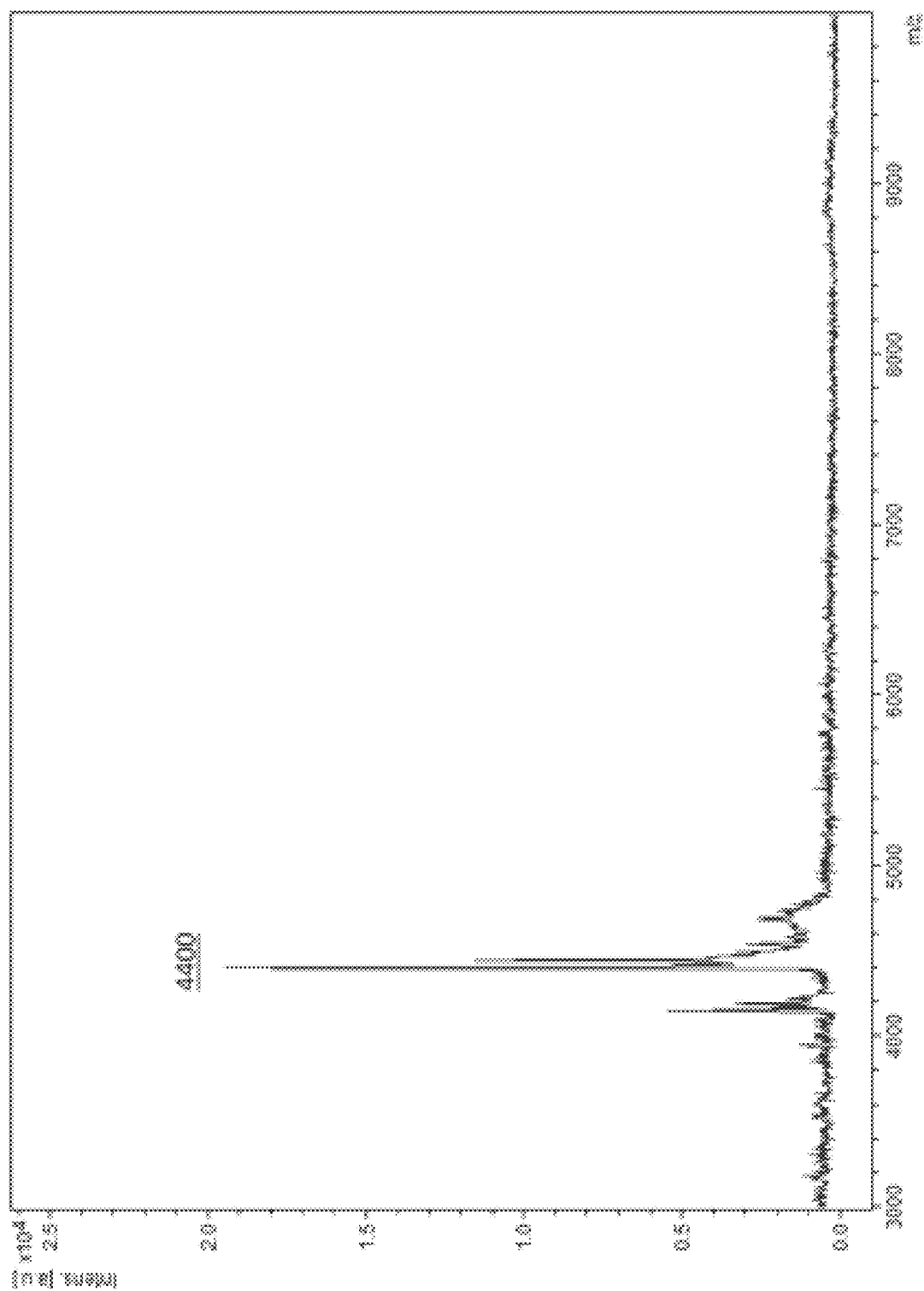
FIGS. 14C provides MALDI-TOF spectrum data of uncloaked 12 mer RNA, generated in accordance with various embodiments of the invention.
Figure 15:
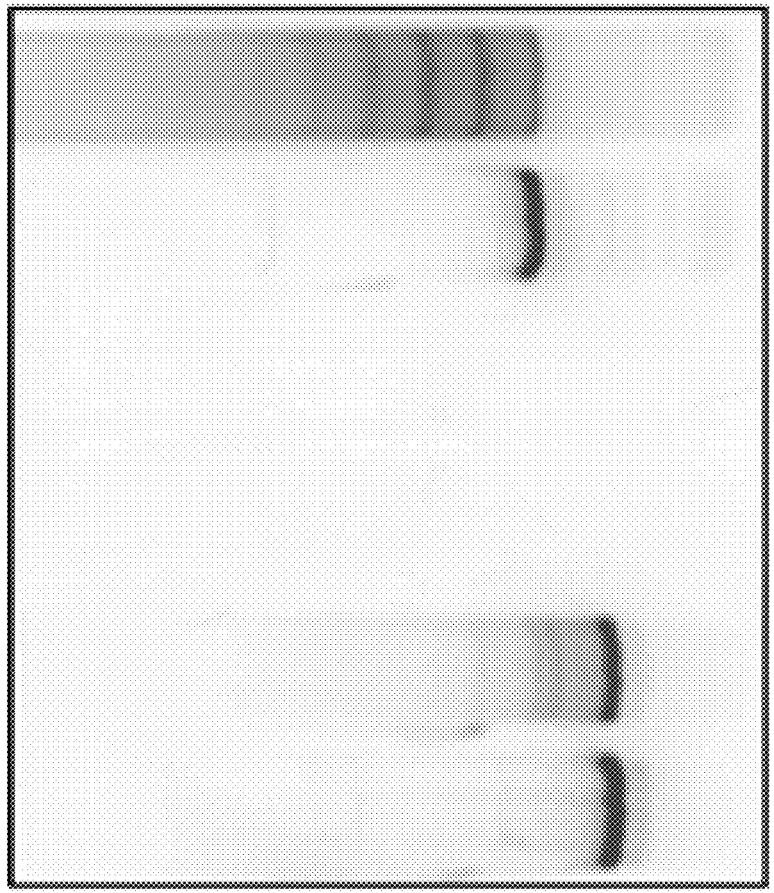
FIG. 15 provides a PAGE electrophoresis image of untreated and treated RNA and DNA, generated in accordance with various embodiments of the invention.

Cloaked RNA products were analyzed by denaturing polyacrylamide gel electrophoresis (PAGE), and up to five new mobility-shifted bands were observed, suggestive of the presence of several adducts per strand, with only a small amount of the unreacted RNA remaining (FIG. 13). In addition, native, cloaked and uncloaked Cy-5 labeled 12-mer RNA (Seq. ID No. 1) were evaluated using 30% denaturing PAGE and MALDI-TOF. The acylation and deacylation was further confirmed by MALDI-TOF spectrometry (FIGS. 14A-14C). In the cloaked RNA sample, several labels were observed but than expected based on the PAGE results (FIG. 14B). The less labels in this analysis is likely due to photodeprotection caused by the UV laser during the mass spectrometric analysis. The results of uncloaked RNA showed that the majority of shifted bands disappeared (FIG. 13), resolving back to a band having the mobility of untreated RNA, which was further confirmed by MALDI-TOF (Untreated in FIG. 14A; Uncloaked in FIG. 14C). As a control, analogous 12 nt DNA was incubated with PCA 1, and little (<5%) reaction was observed (FIG. 15), which supports the hypothesis that PCA 1 reacts with the 2'-OH groups of RNA rather than other nucleophiles such as the exocyclic amines on nucleobases.

CLOAKING APPLICATION EXAMPLE 1

Inhibition of RNA Hybridization

Figure 16:
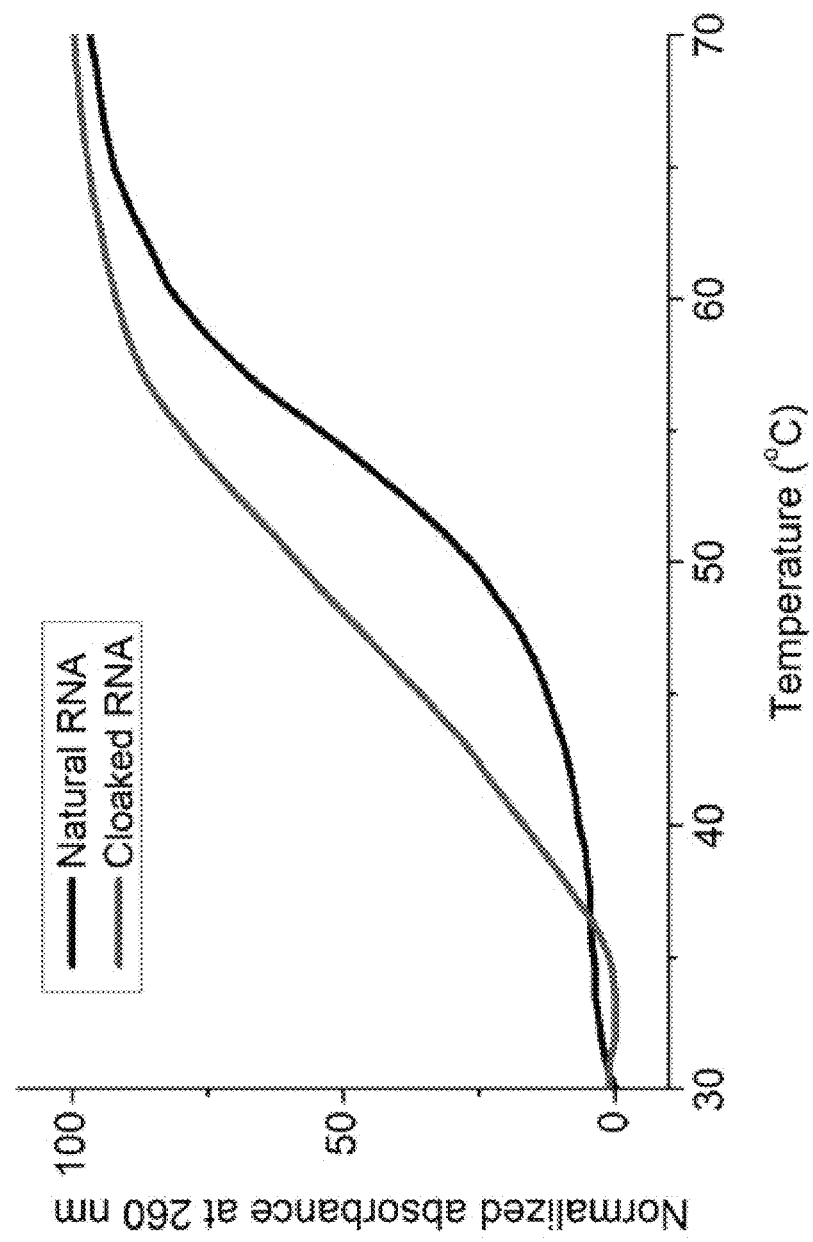
FIG. 16 provides thermal denaturation curves of unmodified RNA oligomer and cloaked RNA with a complementary DNA strand, generated in accordance with various embodiments of the invention.

Hybridization of untreated, cloaked, and uncloaked RNA was examined. Initial experiments measured the effect of photocloaking on thermal stability of a duplex. Untreated and cloaked RNA template 1 (Seq. ID No. 2) were annealed to its complementary DNA strand in phosphate buffer pH=7.2, 100 mM NaCl at 300 nM by heating the sample to 95° C. for 2 min and then cooling to room temperature. Melting curves were obtained by monitoring the absorbance at 260 nm of the nucleic acid solution while increasing the temperature at a rate of 1° C./min. Curves were smoothed by adjacent averaging. A 10° C. difference in melting temperature was observed between the untreated RNA strand as compared with cloaked RNA (FIG. 16), indicating that hybridization is significantly hindered by the presence of the photocloaking groups.

Figure 17A:
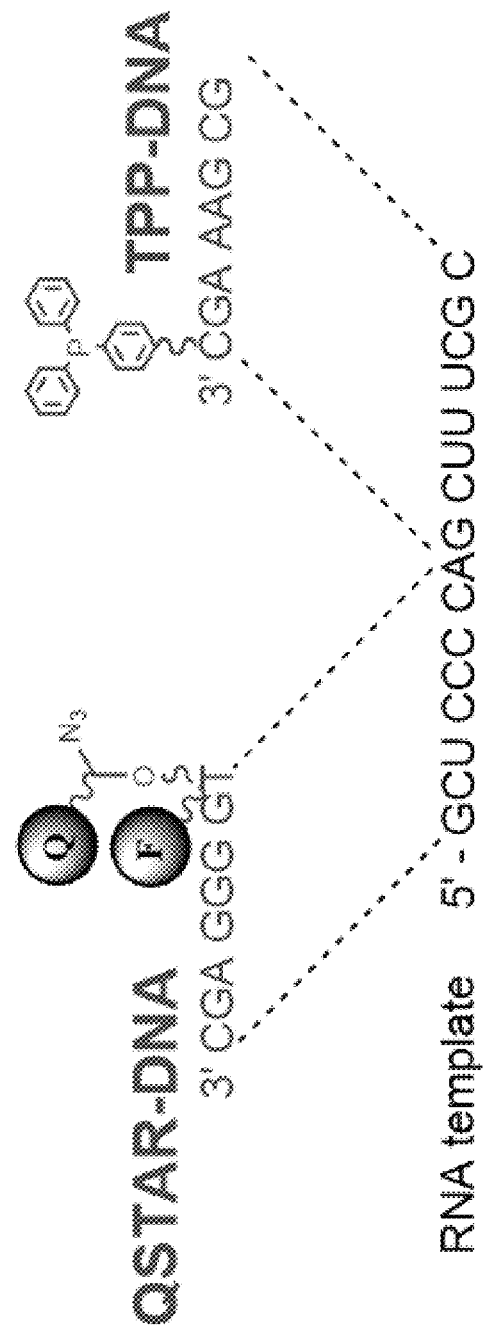
FIG. 17A provides a schematic representation of the fluorogenic nucleic-acid templated QSTAR reaction in accordance with various embodiments of the invention.
Figure 17B:
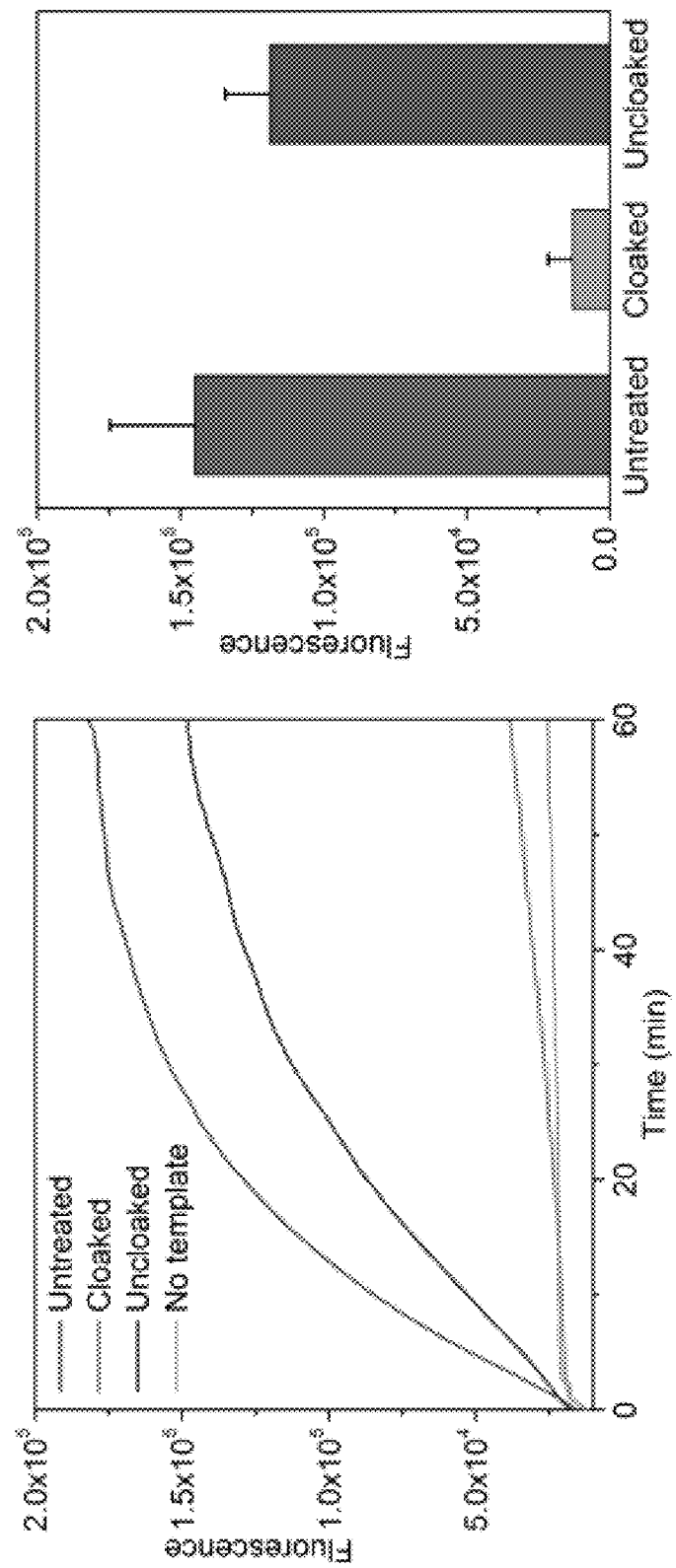
FIG. 17B and 17C provide a graphs detailing fluorescence as a result of hybridization of untreated, cloaked, and uncloaked RNA, generated in accordance with various embodiments of the invention.
Figure 17C:
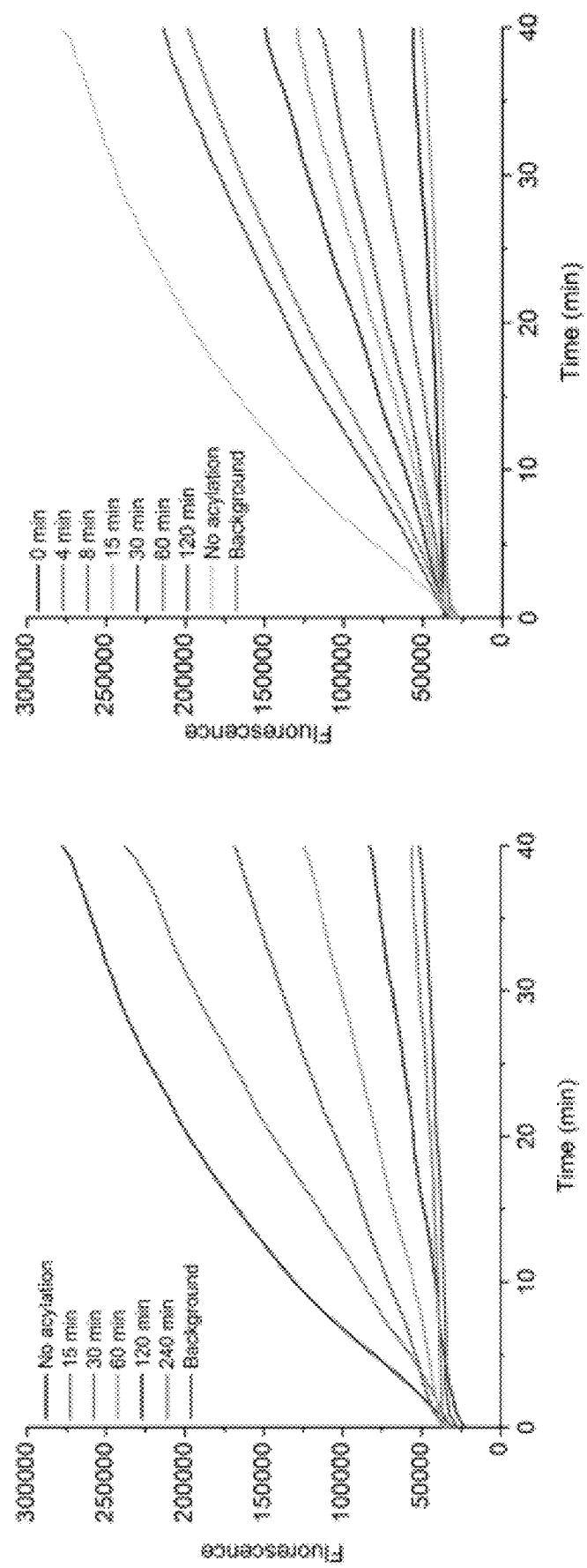

To further test the effect of cloaking on hybridization, a nucleic acid-templated reaction was employed with complementary fluorogenic DNA (Q-STAR) probes (R. M. Franzini and E. T. Kool *J. Am. Chem. Soc.* 2009, 131, 16021-23; and W. A. Velema and E. T. Kool *J. Am. Chem. Soc.* 2017, 139, 5405-11; the disclosures of which are herein incorporated by reference). Probe design and hybrization reaction is provided in FIG. 17A. RNA template (untreated, cloaked or photo-uncloaked) was dissolved in 70 mM Tris-Borate buffer pH=7.0, 10 mM $MgCl_2$ to a concentration of 200 nM. To this was added QSTAR probe (200 nM; Seq. ID No. 3) and TPP probe (400 nM; Seq. ID No. 4) and the fluorescence was monitored overtime at 25° C. on a Fluorolog 3-11 instrument (Jobin Yvon-SPEX). $\lambda_{ex}$=497 nm and $\lambda_{em}$=519 nm. Plots were smoothed by adjacent averaging. FIG. 17B shows that the cloaked RNA was very inefficient in templating the fluorogenic reaction, suppressing signal to 9% of untreated RNA. After the cloaked RNA was exposed to light for up to an hour and subjected to the Q-STAR hybridization probes, a strong restoration of signal (82% of original) was observed (FIG. 17B), consistent with uncloaking at relatively high efficiency. Further investigation revealed that varying incubation time and light exposure allowed the levels of cloaking and uncloaking to be fine-tuned (FIG. 17C).

CLOAKING APPLICATION EXAMPLE 2

Inhibiting Ribozyme Activity

Figure 18A:
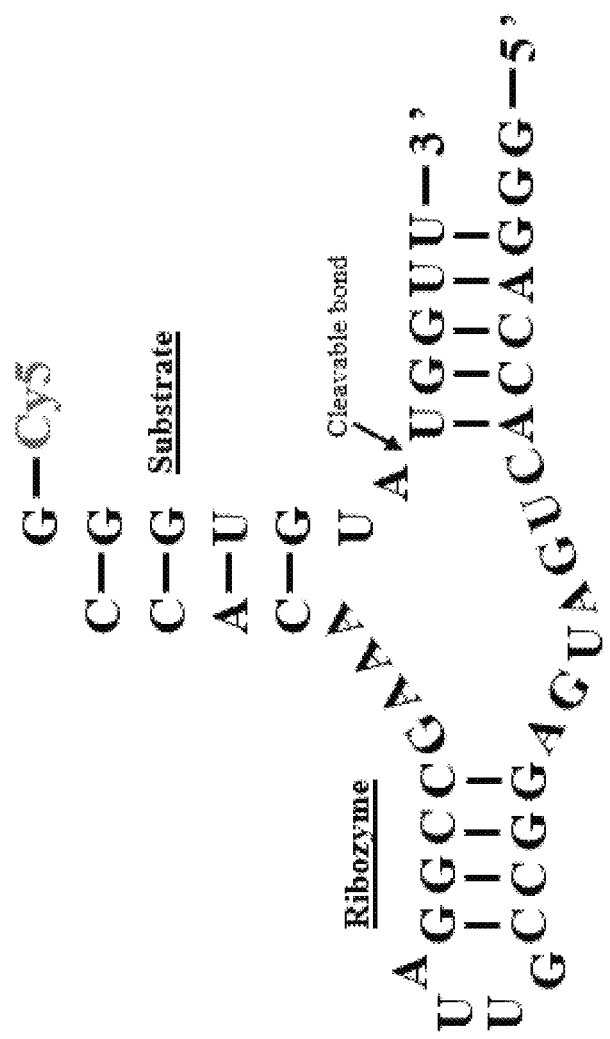
FIG. 18A provides a schematic of the ribozyme hammerhead and a cleavable substrate, generated in accordance with various embodiments of the invention.
Figure 18B:
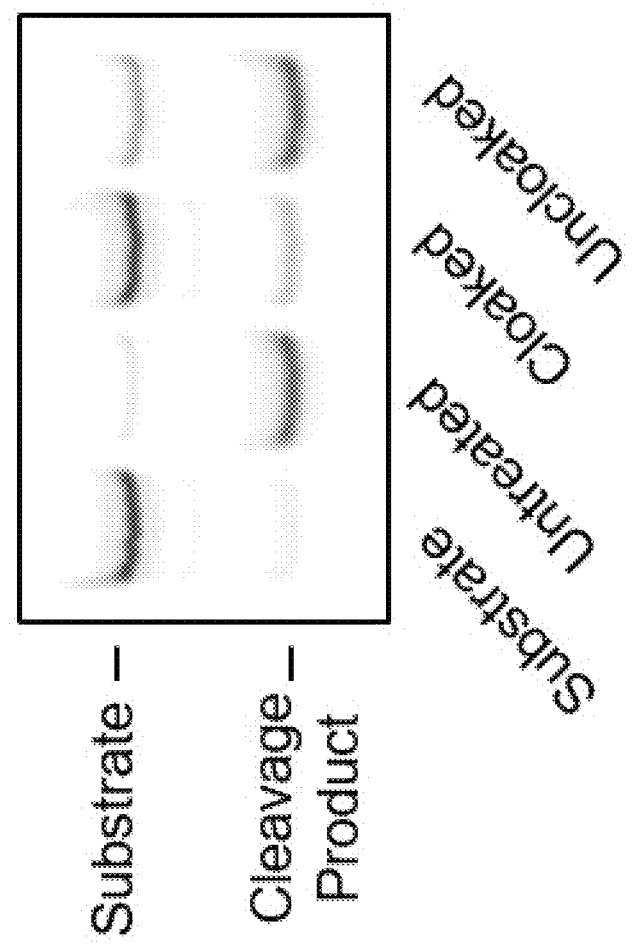
FIG. 18B provides a PAGE electrophoresis image of substrate RNA incubated with untreated, cloaked, and uncloaked hammerhead ribozyme RNA, generated in accordance with various embodiments of the invention.
Figure 18C:
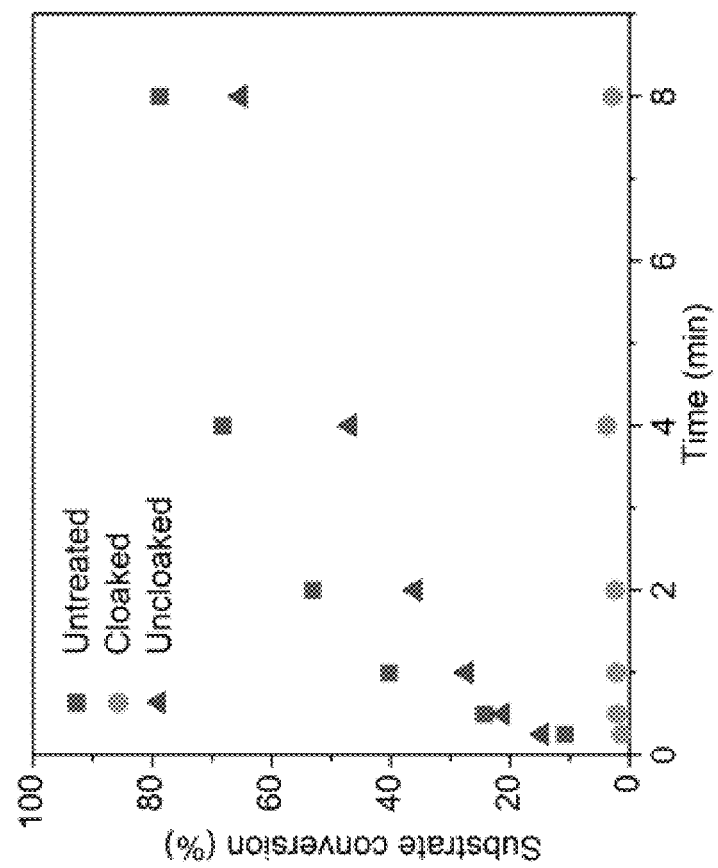
FIG. 18C provides a data graph detailing of converted substrate RNA incubated with untreated, cloaked, and uncloaked hammerhead ribozyme RNA, generated in accordance with various embodiments of the invention.
Figure 18D:
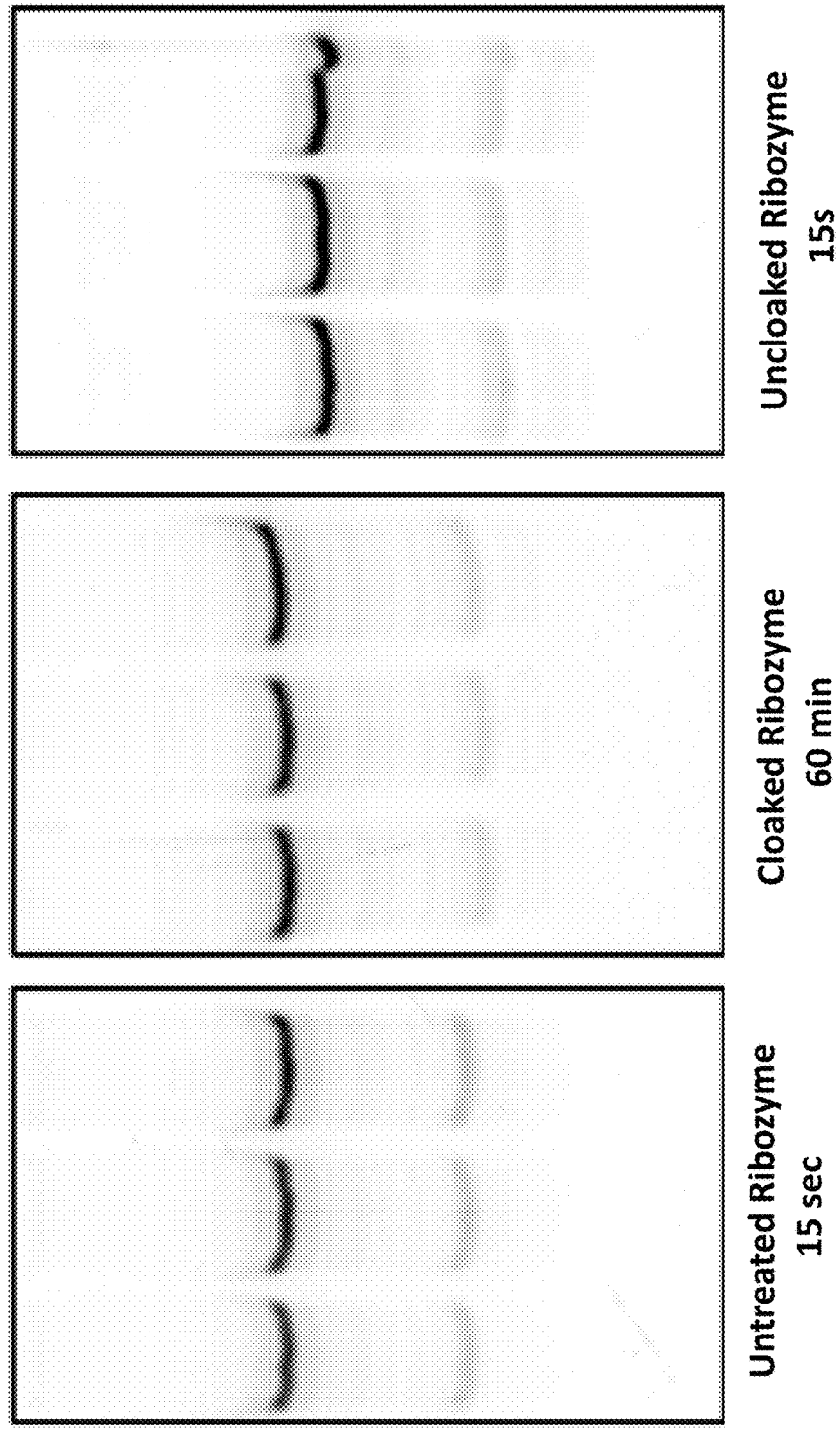
FIG. 18D provides a PAGE electrophoresis images of substrate RNA incubated with untreated, cloaked, and uncloaked hammerhead ribozyme RNA, generated in accordance with various embodiments of the invention.
Figure 18E:
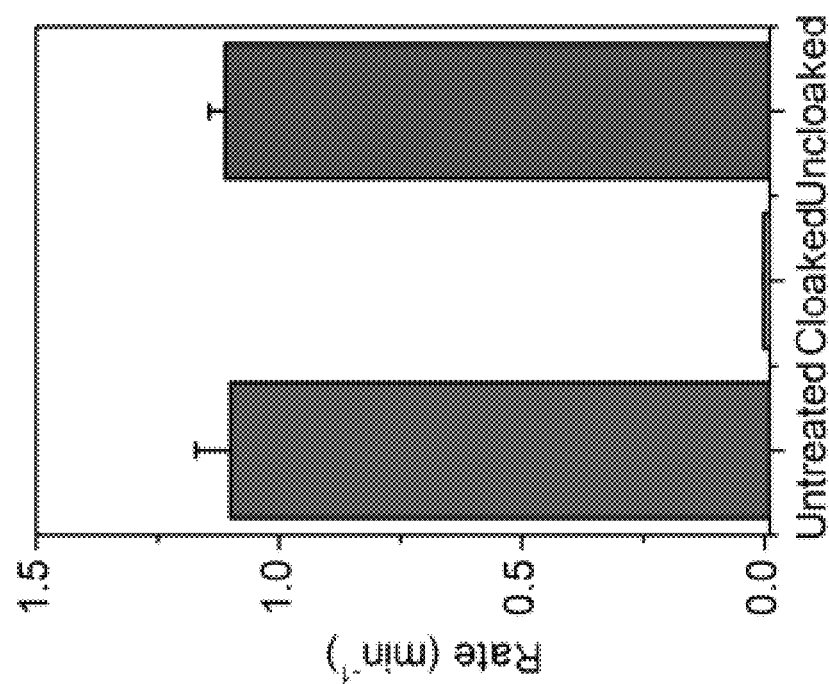
FIG. 18E provides a data graph detailing converted substrate RNA rate when incubated with untreated, cloaked, and uncloaked hammerhead ribozyme RNA, generated in accordance with various embodiments of the invention.

In this example, the ability of photocloaking to control the more complex function of a ribozyme RNA was examined. To form proper tertiary structure and initiate activity, RNA-cleaving ribozymes hybridize and bind metals (See Y Liu, T. J. Wilson, and D. M. J. Lilley *Nat. Chem. Biol.* 2017, 13, 508-13, the disclosure of which is herein incorporated by reference. Several examples of photocontrolled ribozymes have been reported previously (See S. G. Chaulk and A. M. MacMillan *Nucleic Acids Res.* 1998, 26, 3173-78; A. Nierth, M. Singer and A Jaschke Chem. Commun. (Camb). 2010, 46, 7975-77; D. D. Young and A. Dieters *Bioorganic Med. Chem. Lett.* 2006, 16, 2658-61; and S. G. Chaulk and A. M. MacMillan, 2007 cited supra; the disclosures of which are herein incorporated by reference), with the goal of studying ribozyme structure and folding. All prior studies, however, have been performed with modifications incorporated into RNAs during solid-phase synthesis. Thus, PCA 1 was tested whether it could be used to block a ribozyme in a single post-synthetic step, and subsequently phototrigger its activity. A 34 nt hammerhead ribozyme RNA (FIG. 18A; Seq. ID No. 5) was cloaked under standard conditions at room temperature and isolated from excess reagent and DMSO by precipitation. The cloaked ribozyme (200 nM) was then incubated with Cy5-labeled substrate (500 nM) in 50 mM Tris pH=6.0, 10 mM $MgCl_2$ for 1 hour. The reaction was stopped by the addition of 8 M urea, 100 mM EDTA solution and then analyzed by urea PAGE (FIGS. 18B and 18C). Mock-treated ribozyme showed almost full cleavage of the substrate under these conditions and the cloaked ribozyme exhibited almost complete abrogation of activity, establishing that cloaking with PCA 1 strongly interferes with ribozyme function. Importantly, after 365 nm light exposure, ribozyme function was almost completely restored. The initial rates of substrate conversion were determined before and after cloaking (FIGS. 18D and 18E). Mock-treated ribozyme exhibited a rate of 1.1 $min^{-1}$, which is in accordance with literature (W. G. Scott, L. H. Horan and M. Martrick *Prog. Mol. Biol. Transl. Sci.* 2013, 120, 1-23, the disclosure of which is herein incorporated by reference). After cloaking, the rate dropped 370-fold to $3.010^{-3}$ $min^{-1}$, showing strong blocking of ribozyme function. This was readily restored in RNA exposed to light, which exhibited a rate of 1.1 $min^{-1}$, the same as that of the untreated ribozyme.

Thus, ribozyme function can be robustly controlled by a direct photocloaking strategy.

CLOAKING APPLICATION EXAMPLE 3

Inhibiting RNA Secondary Structure Formation

In this example, the ability of PCAs to control longer RNAs produced by transcription was tested. Photocontrolled aptamers have recently gained interest due to their potential for therapeutic and imaging applications, as exemplified by recent work by Langer and Kohane in which a 26nt nucleolin-binding aptamer for cancer targeting was reported (L. Li et al. *Proc. Natl. Acad. Sci.* 2014, 111, 17099-103, the disclosure of which is herein incorporated by reference; See also, M. C. Buff et al *Nucleic Acids Res.* 2009, 38, 2111-18; L. Qiu et al. *J. Am. Chem. Soc.* 2013, 135, 12952-55; A Heckel and G. Mayer *J. Am. Chem. Soc.* 2005, 12, 822-23; and A. Pinto et al. *ACS Chem. Biol.* 2012, 7, 360-66; the disclosure of which are herein incorporated by reference). It was hypothesized that the current post-synthetic acylation strategy described herein would offer a convenient and simpler method for preparing photocontrolled aptamers of arbitrary length. To test this, the transcribed 105 nt F30 Broccoli aptamer (Seq. ID No. 6; G. S. Filonoy et al. *J. Am. Chem. Soc.* 2014, 136, 16299-308, the disclosure of which is herein incorporated by reference), was chosen as an initial substrate RNA. Broccoli RNA folds into a compact tertiary structure, forming a binding site for the DFHBI dye, which results in a strong increase in fluorescence.

F-30 Broccoli DNA template (3 ng) (Table S1) was amplified by PCR (98° C. for 30 s; 30 times: 98° C. for 10 s, 61° C. for 30 s, 72° C. for 30 s; 72° C. for 5 min, 4° C. forever) using Phusion High-Fidelity PCR master Mix (NEB), and primers mix in 50 µL reaction, according to the NEB protocol. Mini Elute columns, and PNI Buffer (Qiagen) were used to clean up double stranded DNA samples as described in the manufacturer's instructions. DNA was eluted using RNase-free water (Corning), and its purity was verified using electrophoresis in a 2% agarose gel (Sigma Aldrich) in 1× TBE Buffer (Life Technologies), 1 h, 80 mA. 250 ng of DNA template was transcribed using MEGA-ShortScript Kit (Life Technologies) according to the manufacturer's protocol. RNA was purified using Zymo RNA Clean&Concentrator-5 according to the manufacturer's instructions. RNA was eluted in RNase-free water, and stored at −78° C. RNA purity and quality was verified by electrophoresis in 2% agarose gels. Broccoli aptamer RNA was cloaked for 4 h with PCA 1 or PCA 2 (100 mM) in water. DMSO treated (untreated), cloaked and uncloaked RNA samples (500 nM) were incubated in folding buffer (40 mM HEPES, pH=7.4, 100 mM KCl, 5 mM MgCl2) with DHBI (1 µM) and heated up to 95° C. for 2 min and then allowed to cool to room temperature for 1 h. Fluorescent emission spectra were recorded on a Fluorolog 3-11 instrument (Jobin Yvon-SPEX), $\lambda_{ex}$=450 nm at 25° C.

Figure 19:
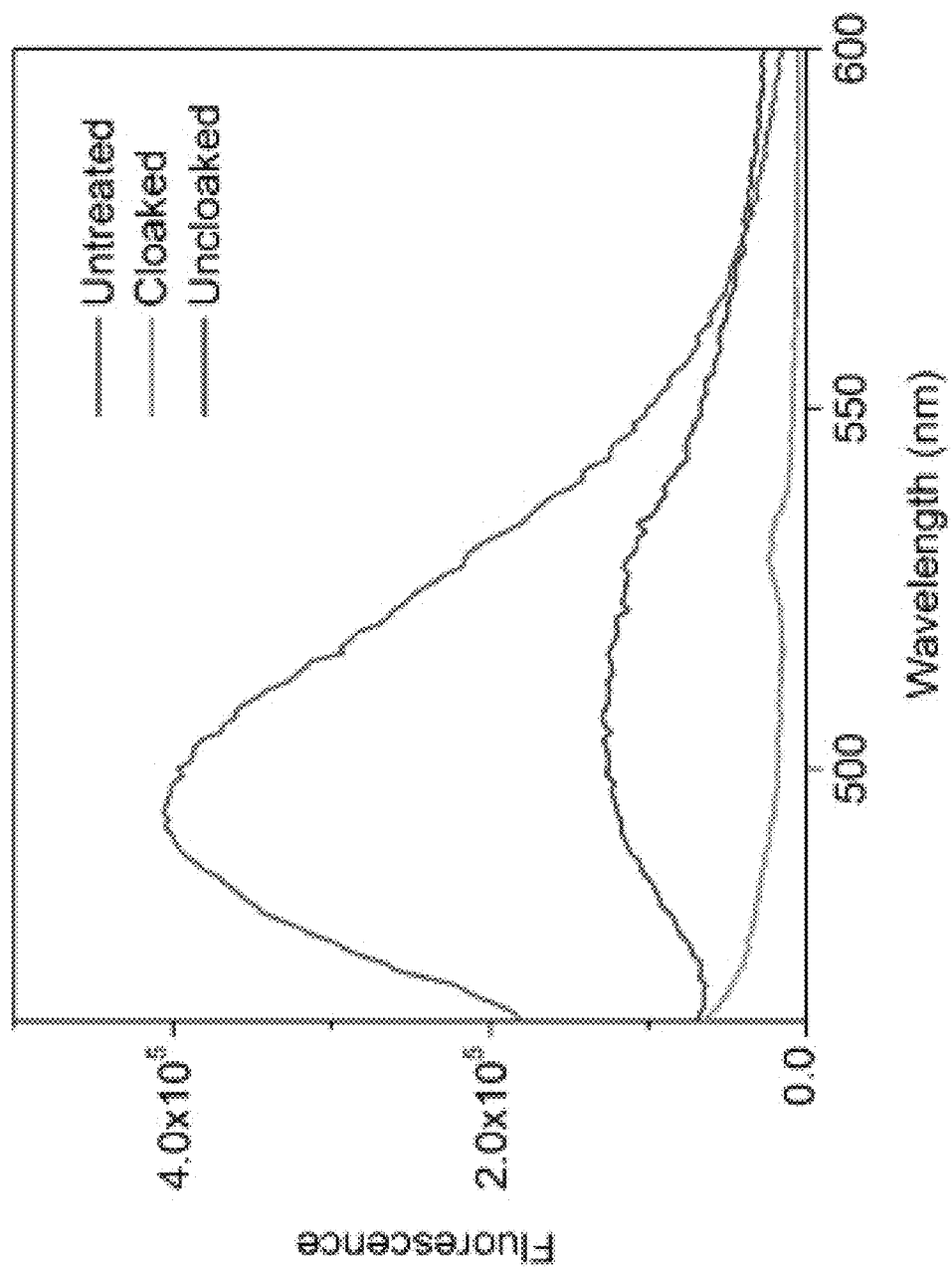
FIG. 19 provides fluorescence emission spectra of untreated, PCA 1 cloaked and uncloaked Broccoli incubated with DFHBI, generated in accordance with various embodiments of the invention.
Figure 20:
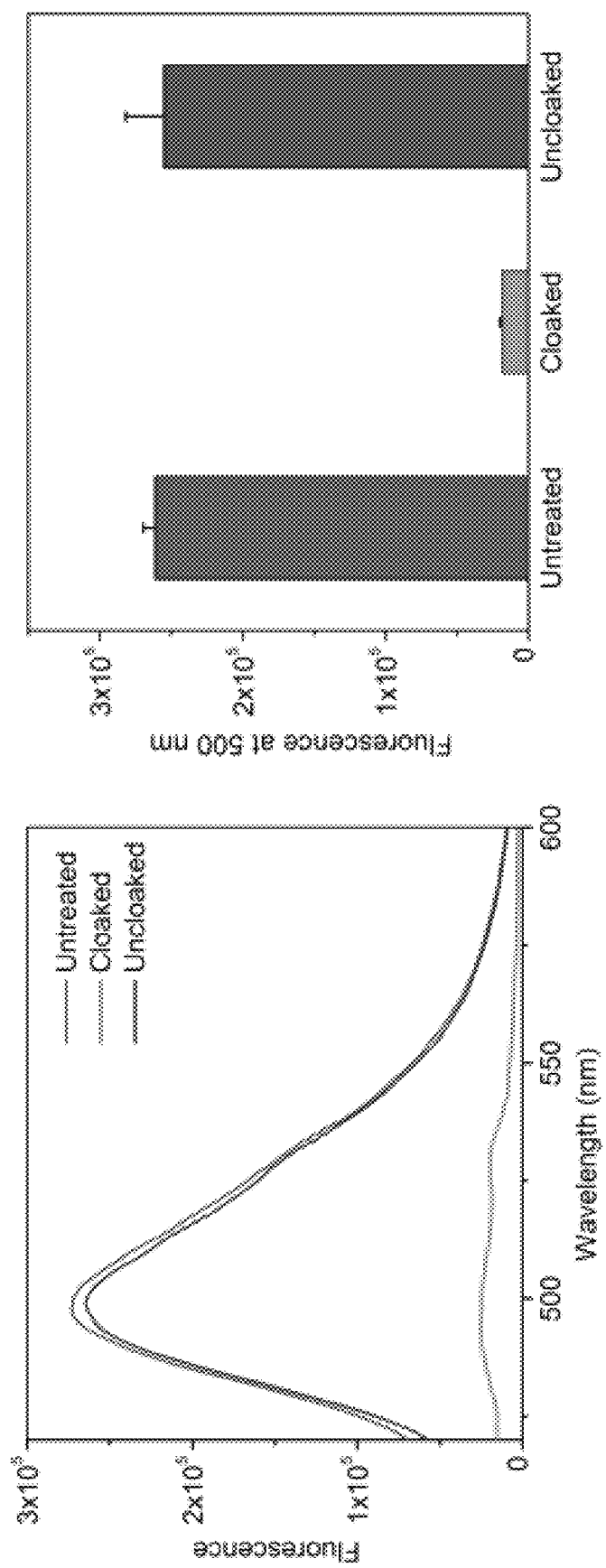
FIG. 20 provides fluorescence emission spectra and a resultant data graph of untreated, PCA 2 cloaked and uncloaked Broccoli incubated with DFHBI, generated in accordance with various embodiments of the invention.

After standard cloaking with PCA 1, initial studies revealed strong suppression of fluorescence in Broccoli RNA (FIG. 19), but a relatively poor recovery after light exposure. It was hypothesized that this poor recovery was due to low quantum yields for uncaging of nitrobenzyl carbonates, which may be problematic on longer RNAs containing greater numbers of acyl groups. To address this, PCA 2, which bears an additional α-methyl group at the benzylic position to improve the photocleavage quantum yield, was utilized in the same experiment. Broccoli aptamer RNA cloaked with PCA 2 exhibited very dim fluorescence, whereas the untreated sample showed pronounced emission (FIG. 20). When the cloaked aptamer was exposed to light and incubated with DFHBI and refolded, fluorescence was completely restored to the level of the untreated sample. These RNA aptamer experiments emphasized the strength of the photocloaking approach, which is carried out in a single step on RNAs considerably longer than are conveniently synthesized by chemical methods. In principle, the cloaking could also be carried out on biologically derived RNAs as well.

CLOAKING APPLICATION EXAMPLE 4

In Vivo Applications

In this example, the capability to use this photocloaking strategy to switch on RNA function in cells was assessed by transfecting a cloaked Broccoli RNA construct into human cells and then exposing cells to light was explored. For these experiments, a larger 237 nt RNA (Seq. ID No. 7) construct encoding two dimeric Broccoli aptamers was prepared. This construct is known to be stable in the intracellular medium (G. S. Filonoy et al. *Chem. Biol.* 2015, 22 (5), 649-60, the disclosure of which is herein incorporated by reference). Accordingly, F30-2xdB_2 DNA (100 pmol; Seq. ID No. 8) was 5' adenylated using Mth Ligase (100 pmol, NEB) according to NEB's protocol. Mini Elute columns, and PNI Buffer (Qiagen) were used to clean up double stranded DNA samples according to manufacturer's instructions. ssDNAs F30-2xdB_2 (40 pmol) and F30-2xdB_1 (20 pmol) were ligated according to NEB description, using Thermostable 5' App DNA/RNA Ligase (40 pmol, NEB). Ligated DNA was purified on DNA Clean&Concentrator 5 columns (Zymo Research) using Zymo's protocol. F-30 2xd Broccoli ssDNA template (3 ng) was amplified by PCR (98° C. for 30 s; 30 times: 98° C. for 10 s, 60° C. for 30 s, 72° C. for 30 s; 72° C. for 5 min, 4° C. forever) using Phusion High-Fidelity PCR master Mix (NEB), and primers mix in 50 µL reaction, according to the NEB protocol. DNA was purified in 1.8% agarose gel (Sigma Aldrich) in 1× TBE Buffer (Life Technologies), 1 h, 80 mA, next to the length standard Gene Ruler 1 kb Plus DNA Ladder (Thermo Fisher Scientific). The band of interest was cut out and dsDNA was extracted using GeneJET Gel Extraction Kit (Thermo Fisher Scientific). DNA was eluted using RNase-free water (Corning), and its purity was verified using electrophoresis in a 2% agarose gel (Sigma Aldrich) in 1× TBE Buffer (Life Technologies), 1 h, 80 mA, next to the length standard Gene Ruler 1 kb Plus DNA Ladder (Thermo Fisher Scientific). 250 ng of dsDNA template was transcribed using MEGA-ShortScript Kit (Life Technologies) according to the manufacturer's protocol. RNA was purified using Zymo RNA Clean&Concentrator-5 according to the manufacturer's instructions. RNA was eluted in RNase-free water, and stored at −78° C. RNA purity and quality were verified by electrophoresis in 2% agarose gels.

In vitro cloaking of this longer RNA was carried out with PCA 2 under standard conditions, transfected in HeLa cells and after incubating for 5 h, cells were illuminated with 365 nm light under an epifluorescence microscope. Accordingly, F30-2xd Broccoli aptamer RNA was cloaked for 4 h with PCA 2 (100 mM) in water or DMSO treated in the same conditions (untreated). HeLa cells were seeded at a concentration of $1.8 \times 10^4$ cells per well to an 8-well plate in supplemented DMEM culture medium (10% FBS, Gibco, 1× Penicillin/Streptomycin, Thermo Fisher Scientific) and incubated for 16 h at 37° C. and 5% $CO_2$ with 95% humidity.

Figure 21:
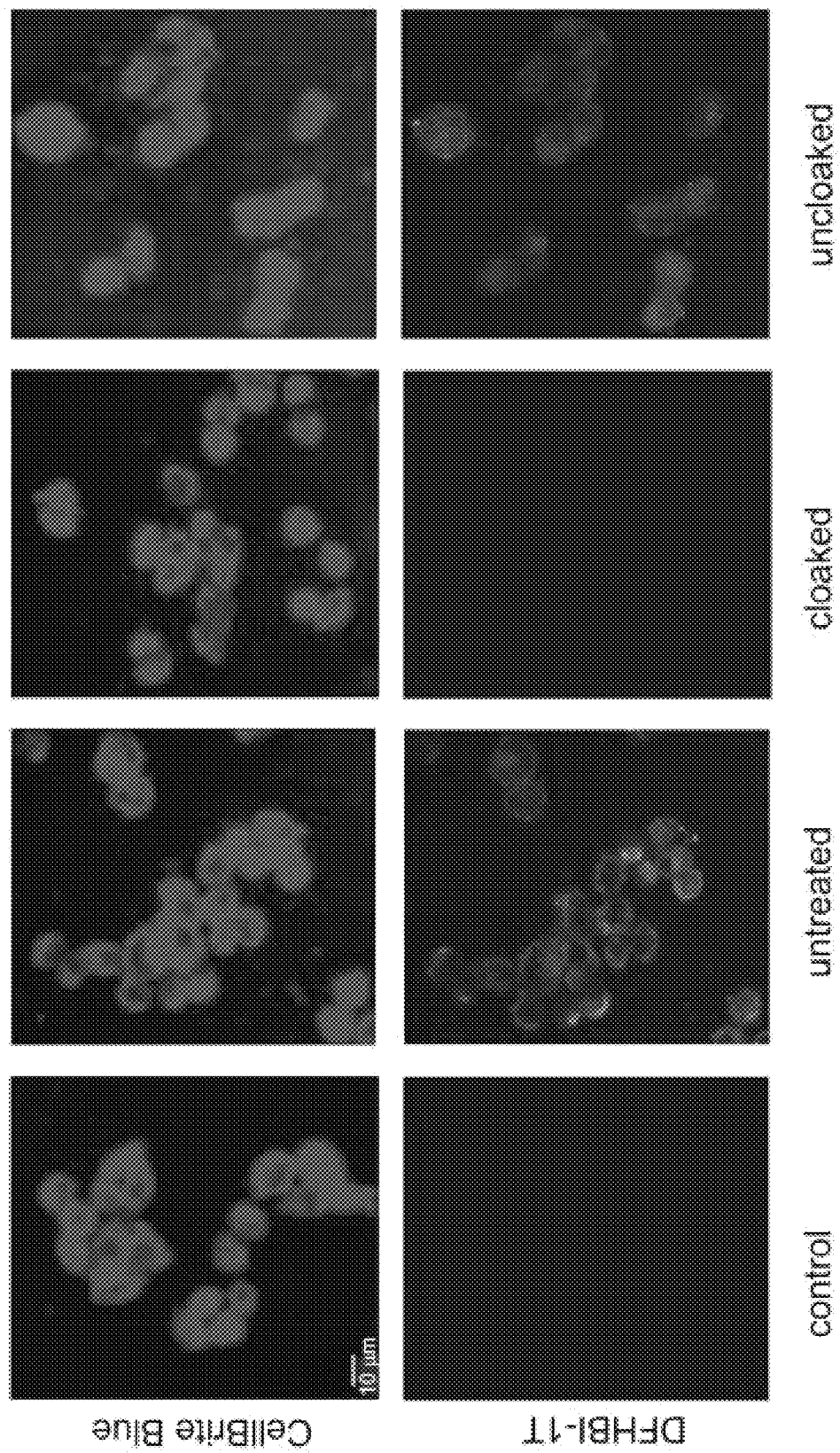
FIG. 21 provides epifluorescence microscopy images of HeLa cells transfected with untreated, cloaked, or uncloaked 237nt Broccoli aptamer, generated in accordance with various embodiments of the invention.

Old medium was removed and replaced with 180 μL of a new supplemented DMEM medium (Gibco). To transfect aptamer RNA to HeLa cells transfection mixture (20 μL of OptiMEM medium (Gibco), 0.6 μL of Lipofectamine MessengerMAX (Thermo Fisher Scientific) and 5 μg of RNA) was prepared. The transfection mixture was added dropwise to each well and incubated for 5 h. The transfection medium was replaced with supplemented DMEM medium and cells exposed to light 375 nm>λ>325 nm for 30 minutes. In all wells medium was replaced with fresh staining mixture containing: 120 mM sucrose, 5 mM Mg SO$_4$, 25 mM HEPES pH 7.4, 40 μM DFHBI-1T (Lucerna Inc.) and 1× CellBrite Blue Cytoplasmatic Membrane Staining Kit (Biotium) in DMEM, and cells were incubated for next 30 minutes. The staining mixture was removed and cells washed with fresh DMEM. Medium was removed and plates prepared to visualization using the epifluorescence microscope Nikon Eclipse i80 at room temperature. Visualization and imaging of cells were carried out using bright field and fluorescence filters: blue (375 nm>$\lambda_{ex}$>325 nm; $\lambda_{em}$>420 nm) and green (500 nm>$\lambda_{ex}$>460 nm; $\lambda_{em}$>520 nm). Images were analyzed and overlapped using Image J software. The same RNA mock-treated with DMSO was used s a control. The experiments revealed that the untreated RNA was able to yield a positive fluorescence signal in cells after transfection and incubation with the DFHBI dye (FIG. 21), consistent with the expected formation of folded Broccoli structure. On the other hand, cloaked RNA showed no measurable signal above background after transfection, confirming that cloaking did indeed strongly inhibit aptamer function in this 237 nt RNA. Finally, experiments with subsequent light exposure revealed the emergence of a visible green fluorescence signal attributable to restored Broccoli RNA (FIG. 21).

CLOAKING APPLICATION EXAMPLE 5

Control of Messenger RNA Function

The photocloaking strategy was validated on messenger RNAs. The first experiments were aimed at optimizing the number of cloaking groups required to abolish mRNA function in order to achieve reasonable uncloaking efficiency. In vitro transcribed eGFP and Luciferase (Luc) mRNAs (5'-m7G capped, m5C modified and polyadenylated) were cloaked by 0.01 M cloaking reagent in water for 1 to 4 hours, immediately purified by precipitation and dissolved in nuclease free water. The cloaked eGFP or Luc transcripts were transfected, using 30 ng of mRNA per 100 μL of DMEM supplemented medium (10% FBS, 1× Pen/Strep) and Lipofectamine MessengerMAX Transfection Reagent, into HeLa cells. After 8 hours' transfection, medium was replaced with fresh medium, cells irradiated for 5-60 minutes ($\lambda_{abs}$~365 nm over a transilluminator) and expression continued for next 12-14 hours. Using fluorescence microscopy and plate readers, the recovery of eGFP and Luciferase (in presence of ViviRen™ Live Cell Substrate) expression was determined. Data showed that usage of the ion free denaturing conditions resulted in an efficient inhibition of mRNA expression in as low concentration as 0.01M cloaking reagent. The highest level of mRNA expression recovery, together with minimal cytotoxicity effect, was achieved after 45 minutes of UV irradiation. In the optimized conditions of uncloaking, mRNA expression was observed at the level of 30% for eGFP and up to 23% for Luciferase relative to untreated mRNA controls. In contrast, non-irradiated cloaked mRNAs produced no measurable signal over background.

CLOAKING APPLICATION EXAMPLE 6

Control of Expression in Zebrafish

To test applicability of cloaking technology in a living organism, cloacking and uncloaking of the fluorescent gene mCherry mRNA was tried in a zebrafish embryo. The cloaking/uncloaking conditions were optimized using the cell culture model, as described above. Global and spatial expression of mRNA was achieved by injecting 1-cell stage zygotes with 150 pg of in vitro transcribed and cloaked mRNAs. The embryo at the developmental stage 3.5 hours post fertilization was irradiated for 30 seconds under the microscope ($\lambda_{abs}$~365 nm). The embryo, visualized at 24 hours stage, showed mCherry expression recovery up to 30% relative to control mRNA, while cloaked RNA showed no visible signal.

In vivo mRNA expression is also capable of being activated and controlled in a spatial manner. Zebrafish zygotes were injected with cloaked mCherry mRNA and then locally irradiated at the developing notochord (mesoderm tissue) to uncloak the mRNA at the spanning gastrulation developmental stage (6 hours post fertilization). The embryos were fixed, and spatial changes in mRNA expression assessed by whole-mount immunostaining. The localized photo-uncloaking approach showed an intense, spatial mCherry expression in notochord. This technique opens a new general approach for spatiotemporal control of RNAs with many applications in biology and medicine.

SEQUENCE LISTING

Table 1 provides a listing of the sequences used in this application.

TABLE 1

Sequence Listing

| Sequence ID No. | Identifier | Type | Sequence |
|---|---|---|---|
| Seq. ID No. 1 | 12-mer | RNA | 5' Cy5-GGG UGU AUG GUU |
| Seq. ID No. 2 | RNA template 1 | RNA | 5' GCU CCC CAG CUU UCG C |
| Seq. ID No. 3 | QSTAR Probe | RNA | 5' Dabsyl-azidoetherlinker-T$^F$GG GGA GC |
| Seq. ID No. 4 | TPP Probe | RNA | 5' GCG AAA GC-TPP |
| Seq. ID No. 5 | Hammerhead Ribozyme | RNA | 5' GGG ACC ACU GAU GAG CCC GUU AGG CCG AAA CAC C |
| Seq. ID No. 6 | F30 Broccoli aptamer | RNA | 5' TAA TAC GAC TCA CTA TAG GGT TGC CAT GTG TAT GTG GGA GAC |

TABLE 1-continued

Sequence Listing

| Sequence ID No. | Identifier | Type | Sequence |
|---|---|---|---|
| | | | GGT CGG GTC CAG ATA TTC GTA |
| | | | TCT GTC GAG TAG AGT GTG GGC |
| | | | TCC CAC ATA CTC TGA TCC TTC |
| | | | GGG ATC ATT CAT GGC |
| Seq. ID No. 7 | F30-2xdB_1 | RNA | 5' TAA TAC GAC TCA CTA TAG GGT TGC CAT GTG TAT GTG GGA GAC GGT CGG GTC CAT CTG AGA CGG TCG GGT CCA GAT ATT CGT ATC TGT CGA GTA GAG TGT GGG CTC AGA TGT CGA GTA GAG TGT GGG CTC CCA CAT A |
| Seq. ID No. 8 | F30-2xdB_2 | DNA | 5'/5Phos/CTC TGA TCC AGA CGG TCG GGT CCA TCT GAG ACG GTC GGG TCC AGA TAT TCG TAT CTG TCG AGT AGA GTG TGG GCT CAG ATG TCG AGT AGA GTG TGG GCT GGA TCA TTC ATG GCA A |

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

---

What is claimed is:

1. A composition comprising:

an RNA polymer, wherein the RNA polymer is acylated with a first adduct linked to a 2'-hydroxyl group of a first ribose; and wherein the first adduct has a structure selected from the following group of structures:

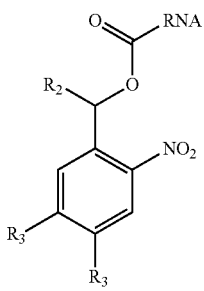

wherein the first adduct is linked to the RNA polymer via a carbonate linkage with the 2'-hydroxyl of ribose; R2 is an alkyl or H; and R3 is an alkoxy or H;

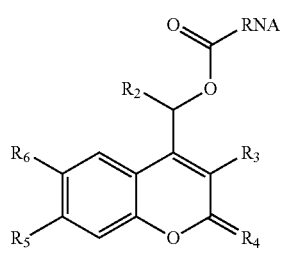

wherein the first adduct is linked to the RNA polymer via a carbonate linkage with the 2'-hydroxyl of ribose; R2 is an alkyl, alkoxy, or H; R3 is an alkyl, aryl, nitro, cyano or H; R4 is (C—R₂), O, or S; R5 is an alkoxy, (N—R₂), OH, or H; and R6 is a halogen or H;

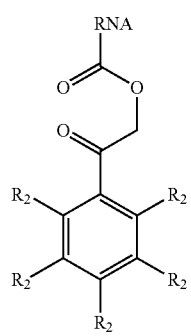

wherein the first adduct is linked to the RNA polymer via a carbonate linkage with the 2'-hydroxyl of ribose; and R2 is an alkyl, alkoxy, nitro, OH, or H;

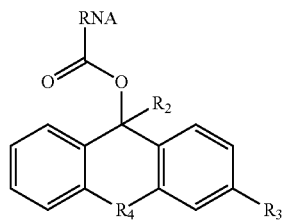

wherein the first adduct is linked to the RNA polymer via a carbonate linkage with the 2'-hydroxyl of ribose; R2 is an aryl or H; R3 is an alkoxy or H; and R4 is O or S;

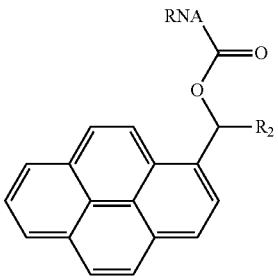

wherein the first adduct is linked to the RNA polymer via a carbonate linkage with the 2'-hydroxyl of ribose; and R2 is an alkyl or H;

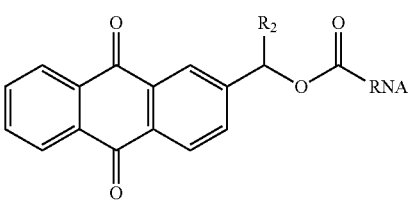

wherein the first adduct is linked to the RNA polymer via a carbonate linkage with the 2'-hydroxyl of ribose; and R2 is an alkyl or H;

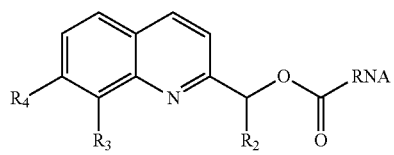

wherein the first adduct is linked to the RNA polymer via a carbonate linkage with the 2'-hydroxyl of ribose; R2 is an alkyl, alkoxy, or H; R3 is a halogen or H; and R4 is an alkoxy, OH, or H;

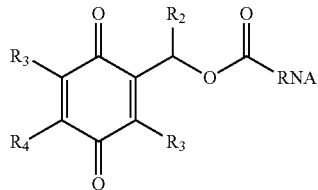

wherein the first adduct is linked to the RNA polymer via a carbonate linkage with the 2'-hydroxyl of ribose; R2 is an alkyl, alkoxy, or H; R3 is an alkyl or H; and R4 is an alkyl, N-alkyl, or H;

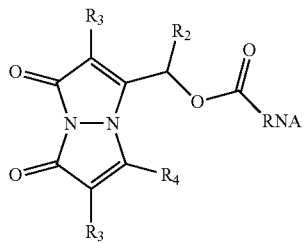

wherein the first adduct is linked to the RNA polymer via a carbonate linkage with the 2'-hydroxyl of ribose; R2 is an alkyl, alkoxy, or H; R3 is an alkyl or H; and R4 is an alkyl, alkoxy, or H;

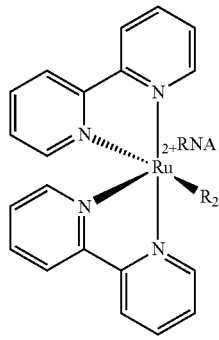

wherein the first adduct is linked to the RNA polymer via a carbonate linkage with the 2'-hydroxyl of ribose; and R2 is an appropriate ligand;

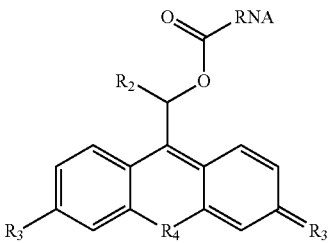

wherein the first adduct is linked to the RNA polymer via a carbonate linkage with the 2'-hydroxyl of ribose; R2 is an alkyl, alkoxy, or H; R3 is an alkoxy, N-alkyl, O, N, or H; and R4 is Si, S, or O; and

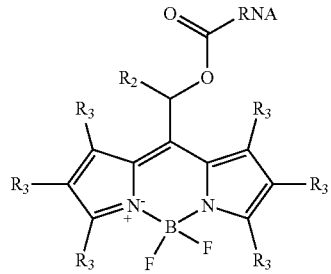

wherein the first adduct is linked to the RNA polymer via a carbonate linkage with the 2'-hydroxyl of ribose; R2 is an alkyl, alkoxy, or H; and R3 is an alkyl, aryl, alkoxy, halogen or H.

2. The composition of claim 1 further comprising a substituent on the first adduct, wherein the substituent is a solubility enhancing group.

3. The composition of claim 2, wherein the solubility enhancing group is a trialkyl amine.

4. The composition of claim 2, wherein the solubility enhancing group is cationic.

5. The composition of claim 2, wherein the solubility enhancing group is anionic.

6. The composition of claim 1, wherein the first adduct is capable of being removed from the RNA polymer by exposure to radiant energy.

7. The composition of claim 1, wherein the RNA polymer is polyacylated with at least a second adduct, wherein the second adduct is linked to a 2'-hydroxyl group of a second ribose.

8. The composition of claim 7, wherein the linkage of each adduct of the polyacylated RNA polymer was formed by a single cloaking reaction.

9. The composition of claim 7, wherein the polyacylated RNA polymer has adducts linked to at least a percentage of the ribosyl 2'-hydroxyl groups, wherein the percentage is selected from a group consisting of: 10%, 20%, 30%, 40%, 50%, 60%, 70%, 80%, and 90%.

10. The composition of claim 7, wherein every accessible ribosyl 2'-hydroxyl group of the RNA polymer is acylated.

11. The composition of claim 1, wherein the RNA polymer is longer than a length selected from a group consisting of: 200 nucleotides (nt), 300 nt, 400 nt, 500 nt, 600 nt, 700 nt, 800 nt, 900 nt, 1000 nt, 2000 nt, and 3000 nt.

12. The composition of claim 1, wherein, prior to acylation of the RNA polymer, the RNA polymer is derived from an in vivo source.

13. The composition of claim 1, wherein, prior to acylation of the RNA polymer, the RNA polymer is derived from an in vitro method.

14. The composition of claim 13, wherein the in vitro method is one of: RNA polymerase extension and oligomeric synthesis.

15. The composition of claim 1, wherein the RNA polymer is one of: mRNA, siRNA, miRNA, shRNA, circRNA, antisense RNA, ribozyme, riboswitch, tRNA, rRNA, snRNA, snoRNA, aptamer, and guide RNA for CRISPR/Cas9.

16. The composition of claim 1, wherein the the first adduct acylated to the RNA polymer mitigates a function of the polymer.

17. The composition of claim 16, wherein the function is one of: hybridization, secondary structure formation, mRNA translation, and protein interaction.

18. The composition of claim 1, wherein the acylated RNA polymer is utilized in a medicament.

* * * * *